(12) United States Patent
Laird et al.

(10) Patent No.: US 7,566,716 B2
(45) Date of Patent: Jul. 28, 2009

(54) IMIDAZOPYRAZINES AS RAF INHIBITOR COMPOUNDS

(75) Inventors: Ellen Laird, Longmont, CO (US); George Topalov, Superior, CO (US); Joseph P. Lyssikatos, Superior, CO (US); Mike Welch, Westminster, CO (US); Jonas Grina, Superior, CO (US); Josh Hansen, Longmont, CO (US); Brad Newhouse, Broomfield, CO (US)

(73) Assignee: Array Biopharma Inc., Boulder, CO (US)

(*) Notice: Subject to any disclaimer, the term of this patent is extended or adjusted under 35 U.S.C. 154(b) by 331 days.

(21) Appl. No.: 11/436,353

(22) Filed: May 18, 2006

(65) Prior Publication Data

US 2006/0281751 A1 Dec. 14, 2006

Related U.S. Application Data

(60) Provisional application No. 60/683,175, filed on May 20, 2005.

(51) Int. Cl.
*A61K 31/497* (2006.01)
(52) U.S. Cl. .................. 514/252.1; 544/106; 544/350; 546/152; 546/184; 546/348; 548/127; 548/146; 548/373.1; 548/490; 549/29
(58) Field of Classification Search ............ 514/252.1; 544/106, 350; 546/152, 184, 348; 548/127, 548/146, 373.1, 490; 549/29
See application file for complete search history.

(56) References Cited

U.S. PATENT DOCUMENTS

| | | | |
|---|---|---|---|
| 6,638,933 B2 | 10/2003 | Gerlach et al. | |
| 7,078,405 B2 | 7/2006 | Hibi et al. | |
| 7,087,607 B2 | 8/2006 | Gerlach et al. | |
| 2003/0119842 A1 | 6/2003 | Gerlach et al. | |
| 2004/0023972 A1 | 2/2004 | Sundermann et al. | |
| 2004/0058938 A1 | 3/2004 | Cullmann et al. | |
| 2004/0220189 A1 | 11/2004 | Sun et al. | |

FOREIGN PATENT DOCUMENTS

| | | |
|---|---|---|
| DE | 101 50 172 | 4/2003 |
| WO | WO 01/27119 | 4/2001 |
| WO | WO 01/81344 | 11/2001 |
| WO | 2004/072080 A1 | 8/2004 |
| WO | WO 2004/072080 | 8/2004 |
| WO | WO 2005/120513 | 12/2005 |
| WO | WO 2006/029980 | 3/2006 |

OTHER PUBLICATIONS

Jordan, V. C. Nature Reviews: Drug Discovery, 2, 2003, p. 205.*

Dörwald, F. Zaragoza. Side Reactions in Organic Synthesis: A Guide to Successful Synthesis Design, Weinheim: Wiley-VCH Verlag GmbH & Co. KGaA, 2005, Preface.*
Vippagunta, et al. Advanced Drug Delivery Reviews, 48, 2001, p. 18.*
Blackburn, "A Three-Component Solid-Phase Synthesis of 3-Aminoimidazo[1,2-a]azines", *Tetrahedron Letters*, 39, pp. 5469-5472, 1998.
Blackburn et al., "Parallel Synthesis of 3-Aminoimidazo[1,2-a]pyridines and pyrazines by a New Three-Component Condensation", *Tetrahedron Letters*, 39, pp. 3635-3638, 1998.
Groebke et al., "Synthesis of Imidazo[1,2-a] annulated Pyridines, Pyrazines and Pyrimidines by a Novel Three-Component Condensation", *Synlett*, pp. 661-663, 1998.
Podergajs et al., "A New Approach for the Synthesis of Fused Imidazoles: The Synthesis of 3-Acyl-Substituted Imidazo[1,2-x]azines", *Synthesis*, 263-265, 1984.
Rimoli et al., "Research on Heterocyclic compounds. XXXVII. Synthesis and anti-inflammatory activity of methyl-substituted imidazo[1,2-a]pyrazine derivatives", *Eur. J. Med. Chem.*, 32, pp. 195-203, 1997.
Sablayrolles et al., "Synthesis of Imidazo[1,2-a]pyrazine Derivatives with Uterine-Relaxing, Antibronchospastic, and Cardiac-Stimulating Properties", *J. Med. Chem.*, 27, pp. 206-212, 1984.
Varma et al., "Microwave-accelerated three-component condensation reaction on clay: solvent-free synthesis of imidazo[1,2-a] annulated pyridines, pyrazines and pyrimidines", *Tetrahedron Letters*, 40, pp. 7665-7669, 1999.
Varma, "Solvent-Free Synthesis of Heterocyclic Compounds Using Microwaves", *J. Heterocyclic Chem.*, 36, pp. 1565-1571, 1999.

* cited by examiner

*Primary Examiner*—James O Wilson
*Assistant Examiner*—Douglas M Willis
(74) *Attorney, Agent, or Firm*—Viksnins Harris & Padys PLLP

(57) ABSTRACT

Compounds of Formula I are useful for inhibiting Raf kinase and for treating disorders mediated thereby. Methods of using compounds of Formula I, and stereoisomers, tautomers, solvates and pharmaceutically acceptable salts thereof, for in vitro, in situ, and in vivo diagnosis, prevention or treatment of such disorders in mammalian cells, or associated pathological conditions are disclosed.

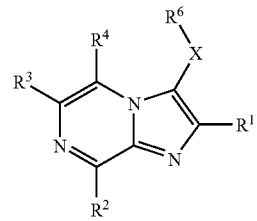

21 Claims, No Drawings

IMIDAZOPYRAZINES AS RAF INHIBITOR COMPOUNDS

CROSS-REFERENCE TO RELATED APPLICATION

This application is related to and claims priority under 35 U.S.C. §119(e) to U.S. Provisional Application No. 60/683,175 filed on May 20, 2005, which is incorporated by reference-herein.

BACKGROUND OF THE INVENTION

1. Field of the Invention

In one aspect, the invention relates to compounds that are inhibitors of Raf kinase, as well as compositions containing these compounds and methods of use. The compounds are useful for inhibiting Raf kinase and for treating disorders mediated thereby. The invention also relates to methods of using the compounds of the present invention for in vitro, in situ, and in vivo diagnosis or treatment of mammalian cells, or associated pathological conditions.

2. Description of the State of the Art

The Raf/MEK/ERK (extracellular signal-regulated kinase) kinase cascade is pivotal in transmitting signals from membrane receptors to transcription factors that control gene expression culminating in the regulation of cell cycle progression (Robinson, M J and Cobb, M H (1997) *Curr. Opin. Cell Biol.* 9:180-186). This cascade can prevent cell death through ERK2 and p90(Rsk) activation and phosphorylation of apoptotic and cell cycle regulatory proteins (Shelton, J G et al. (2003) *Oncogene* 22(16):2478-92). The PI3K/Akt kinase cascade also controls apoptosis and can phosphorylate many apoptotic and cell cycle regulatory proteins. These pathways are interwoven as Akt can phosphorylate Raf and result in its inactivation, and Raf can be required for the anti-apoptotic effects of Akt. Raf is a key serine-threonine protein kinase which participates in the transmission of growth, anti-apoptotic and differentiation messages. These signals can be initiated after receptor ligation and are transmitted to members of the MAP kinase cascade that subsequently activate transcription factors controlling gene expression. Raf is a multigene family which expresses oncoprotein kinases: Raf-1, A-Raf and B-Raf (McCubrey, J A., et al. (1998) *Leukemia* 12(12):1903-1929; Ikawa, et al. (1988) *Mol. and Cell. Biol.* 8(6):2651-2654; Sithanandam, et al. (1990) *Oncogene* 5:1775-1780; Konishi, et al. (1995) *Biochem. and Biophys. Res. Comm.* 216(2):526-534). All three Raf kinases are functionally present in certain human hematopoietic cells, and their aberrant expression can result in abrogation of cytokine dependency. Their regulatory mechanisms differ because C-Raf and A-Raf require additional serine and tyrosine phosphorylation within the N region of the kinase domain for full activity (Mason et al. (1999) *EMBO J.* 18:2137-2148), and B-Raf has a much higher basal kinase activity than either A-Raf or C-Raf. The three Raf oncoproteins play critical roles in the transmission of mitogenic and anti-apoptotic signals. Recently, it has been shown that B-Raf is frequently mutated in various human cancers (Wan, et al. (2004) *Cell* 116:855-867). Development of specific Raf inhibitors may prove efficacious in cancer therapy. The cytoplasmic serine/threonine kinase B-Raf and receptor tyrosine kinases of the platelet-derived growth factor receptor (PDGFR) family are frequently activated in cancer by mutations of an equivalent amino acid. Structural studies have provided important insights into why these very different kinases share similar oncogenic hot spots and why the PDGFR juxtamembrane region is also a frequent oncogenic target (Dibb, NJ (2004) *Nature Reviews Cancer* 4(9):718-27).

Transformation of normal melanocytes into melanoma cells is accomplished by the activation of growth stimulatory pathways, typically leading to cellular proliferation, and the inactivation of apoptotic and tumor suppressor pathways. Small molecule inhibitors of proteins in the growth stimulatory pathways are under active investigation, and their application to melanoma patients would represent a new treatment strategy to inhibit cell proliferation or induce cell death (Polsky, D., (2003) *Oncogene* 22(20):3087-3091; Konopleva, M., et al. (2003) *Blood* 102(11):625a).

B-Raf encodes a RAS-regulated kinase that mediates cell growth and malignant transformation kinase pathway activation. Activating B-Raf mutations have been identified in 66% of melanomas and a smaller percentage of many other human cancers. B-Raf mutations also account for the MAP kinase pathway activation common in non-small cell lung carcinomas (NSCLCs), including V600E and other mutations identified as novel, altering residues important in AKT-mediated B-Raf phosphorylation, which suggest that disruption of AKT-induced B-Raf inhibition can play a role in malignant transformation. Although >90% of B-Raf mutations in melanoma involve codon 600 (57 of 60), 8 of 9 B-Raf mutations reported to date in NSCLC are non-V600 (89%; P<10(−7)), strongly suggesting that B-Raf mutations in NSCLC are qualitatively different from those in melanoma; thus, there may be therapeutic differences between lung cancer and melanoma in response to RAF inhibitors. Although uncommon, B-Raf mutations in human lung cancers may identify a subset of tumors sensitive to targeted therapy (Brose, M S, et al., (2002) *Cancer Research* 62(23):6997-7000).

Raf protein kinases are key components of signal transduction pathways by which specific extracellular stimuli elicit precise cellular responses in mammalian cells. Activated cell surface receptors activate ras/rap proteins at the inner aspect of the plasma membrane, which in turn recruit and activate Raf proteins. Activated Raf proteins phosphorylate and activate the intracellular protein kinases MEK1 and MEK2. In turn, activated MEKs catalyze phosphorylation and activation of p42/p44 mitogen-activated protein kinase (MAPK). A variety of cytoplasmic and nuclear substrates of activated MAPK are known which directly or indirectly contribute to the cellular response to environmental change. Three distinct genes have been identified in mammals that encode Raf proteins; A-Raf, B-Raf and C-Raf (also known as Raf-1) and isoformic variants that result from differential splicing of mRNA are known.

Inhibitors of Raf kinases have been suggested for use in disruption of tumor cell growth and hence in the treatment of cancers, e.g., histiocytic lymphoma, lung adenocarcinoma, small cell lung cancer and pancreatic and breast carcinoma; and also in the treatment and/or prophylaxis of disorders associated with neuronal degeneration resulting from ischemic events, including cerebral ischemia after cardiac arrest, stroke and multi-infarct dementia and also after cerebral ischemic events such as those resulting from head injury, surgery and/or during childbirth (neurotrauma). In particular, it has been suggested that B-Raf is the major Raf isoform activated by the neurotrophin, nerve growth factor (NGF), for NGF induced extracellular signaling by kinase activation (York, et al. (2000) *Mol. and Cell. Biol.* 20(21):8069-8083).

SUMMARY OF THE INVENTION

The invention relates to compounds that are inhibitors of Raf kinases, in particular inhibitors of B-Raf kinase. Certain hyperproliferative disorders are characterized by the overactivation of Raf kinase function, for example by mutations or overexpression of the protein. Accordingly, the compounds of the invention can be used in the treatment of hyperproliferative disorders such as cancer.

More specifically, one aspect of the invention provides compounds having Formula I

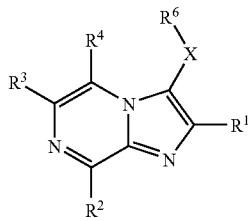

and stereoisomers, tautomers, solvates and pharmaceutically acceptable salts thereof, wherein:

X is $NR^5$, $CH_2$ or CO;

$R^1$ is $C_1$-$C_{10}$ alkyl, $C_2$-$C_{10}$ alkenyl, $C_2$-$C_{10}$ alkynyl, cycloalkyl, heterocycloalkyl, $Z_n$-aryl, heteroaryl, —C(=O)$R^{12}$, —C(=O)O$R^{12}$, —C(=O)$NR^{12}R^{13}$, —$NR^{12}R^{13}$, —N($R^{13}$)C(=O)$R^{12}$, —N($R^{13}$)C(=O)O$R^{12}$, —N($R^{12}$)C(=O)$NR^{13}R^{14}$, —S(O)$R^{14}$, —S(O)$_2R^{14}$ or —S(O)$_2NR^{12}R^{13}$, wherein said alkyl, alkenyl, alkynyl, cycloalkyl, heterocycloalkyl, aryl and heteroaryl portions are optionally substituted with one or more groups independently selected from F, Cl, Br, I, $NO_2$, oxo (with the proviso that it is not on said aryl or heteroaryl) alkyl, $Z_n$-aryl, $Z_n$-heterocycloalkyl, $Z_n$-heteroaryl, $Z_n$-CN, $Z_n$-O$R^{12}$, $Z_n$-C(O)$R^{12}$, $Z_n$-C(O)O$R^{12}$, $Z_n$-C(O)-heterocycloalkyl, $Z_n$-$NR^{15}R^{15}$, $Z_n$-$NR^{12}C(O)R^{13}$, $Z_n$-$NR^{12}C(O)OR^{13}$, $Z_n$-$SR^{12}$, $Z_n$-$SOR^{12}$, $Z_n$-$SO_2R^{12}$, $Z_n$-O—($C_1$-$C_6$ alkyl)-C(O)$NR^{12}R^{13}$, $Z_n$-O—($C_1$-$C_6$ alkyl)-C(O)O$R^{12}$, $Z_n$-O—($C_1$-$C_6$ alkyl)-heterocycloalkyl, $Z_n$-O—($C_1$-$C_6$ alkyl)-C(O)-heterocycloalkyl, $Z_n$-C(O)$NR^{12}R^{13}$, $Z_n$-$NR^{12}$—($C_1$-$C_6$ alkyl)-C(O)$NR^{12}R^{13}$, $Z_n$-$NR^{12}$—($C_1$-$C_6$ alkyl)-C(O)O$R^{12}$, $Z_n$-$NR^{12}$—($C_2$-$C_6$ alkyl)-OC(O)$NR^{12}R^{13}$, $Z_n$-$NR^{12}C(=O)NR^{13}Z_n$-$R^{16}$, and $Z_n$-$NR^{12}$—($C_2$-$C_6$ alkyl)-$NR^{12}C(O)NR^{12}R^{13}$;

$R^2$, $R^3$ and $R^4$ are independently selected from H, F, Cl, Br, I, —C(=O)$R^{12}$, —C(=O)O$R^{12}$, —C(=O)$NR^{12}R^{13}$, —$NR^{12}R^{14}$, —O$R^{12}$, —OC(=O)$R^{12}$, —OC(=O)O$R^{12}$, —OC(=O)$NR^{12}R^{13}$, —$NR^{12}C(O)$—$R^{13}$, —$NR^{12}$—C(O)$NR^{13}R^{14}$ and —$NR^{12}$—C(O)O$R^{13}$;

$R^5$ is H, $C_1$-$C_{10}$ alkyl, $C_2$-$C_{10}$ alkenyl, $C_2$-$C_{10}$ alkynyl, $C_6$-$C_{20}$ cycloalkyl, $C_6$-$C_{20}$ heterocycloalkyl, —C(O)$R^{12}$ or —C(O)O$R^{12}$, wherein said alkyl, alkenyl, alkynyl, cycloalkyl and heterocycloalkyl portions are optionally substituted with one or more groups independently selected from halogen, OH, O-alkyl, and amino;

$R^6$ is

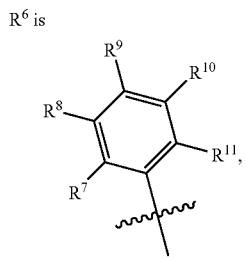

wherein
(i) $R^7$ and $R^8$ form a 5 or 6 membered fused carbocyclic ring substituted with =Y, and $R^9$, $R^{10}$ and $R^{11}$ are independently selected from H, F, Cl, Br, and I, or
(ii) $R^8$ and $R^9$ form a 5 or 6 membered fused carbocyclic ring substituted with =Y, and $R^7$, $R^{10}$ and $R^{11}$ are independently selected from H, F, Cl, Br, and I;

Y is O or N—OH;

$R^{12}$, $R^{13}$ and $R^{14}$ are independently selected from H, alkyl, alkenyl, alkynyl, heteroalkyl, heteroalkenyl, heteroalkynyl, cycloalkyl, heterocycloalkyl, aryl and heteroaryl, wherein said alkyl, alkenyl, alkynyl, heteroalkyl, heteroalkenyl, heteroalkynyl, cycloalkyl, heterocycloalkyl, aryl and heteroaryl are optionally substituted with one or more groups independently selected from halogen, OH, O-alkyl, amino, alkylamino and dialkylamino;

$R^{15}$ is H, —$SO_2$-alkyl, —$SO_2NR^{13}R^{14}$, ($C_1$-$C_6$ alkyl)-OH, —C(O)O-alkyl, alkyl, alkenyl, alkynyl, heteroalkyl, heteroalkenyl, heteroalkynyl, cycloalkyl, heterocycloalkyl, aryl or heteroaryl, wherein said alkyl, alkenyl, alkynyl, heteroalkyl, heteroalkenyl, heteroalkynyl, cycloalkyl, heterocycloalkyl, aryl and heteroaryl portions are optionally substituted with one or more groups independently selected from halogen, OH, O-alkyl, amino, alkylamino and dialkylamino;

$R^{16}$, is heteroaryl that is substituted with one or more alkyl, alkenyl, or alkynyl;

Z is alkylene having from 1 to 4 carbons, or alkenylene or alkynylene each having from 2 to 4 carbons, wherein said alkylene, alkenylene and alkynylene are optionally substituted with one or more groups independently selected from halogen, OH, O-alkyl, and amino; and n is 0, 1, 2, 3 or 4.

Another aspect of the invention provides methods of inhibiting Raf kinase activity, comprising contacting a Raf kinase with an effective inhibitory amount of a compound of Formula I or a composition containing compound of Formula I.

Another aspect of the invention provides methods of preventing or treating disease or disorder modulated by Raf kinases, comprising administering to a mammal in need of such treatment an effective amount of a compound of Formula I or a composition containing a compound of Formula I. Examples of such diseases and disorders include, but are not limited to, hyperproliferative disorders, neurodegeneration, cardiac hypertrophy, pain, migraine or neurotraumatic disease.

Another aspect of the invention provides methods of preventing or treating cancer, comprising administering to a mammal in need of such treatment an effective amount of a compound of Formula I alone or in combination with one or more additional compounds having anti-cancer properties.

Another aspect of the invention provides a compound of Formula I for use in medical therapy.

Another aspect of the invention provides a compound of Formula I for use as a medicament for the treatment of an abnormal cell growth condition in a human or animal.

Another aspect of the invention provides the use of a compound of Formula I in the manufacture of a medicament for the treatment of an abnormal cell growth condition in a human or animal.

Another aspect of the invention includes articles of manufacture, i.e., kits, comprising a compound of Formula I, a container, and a package insert or label indicating a treatment.

Another aspect of the invention includes methods of preparing compounds of Formula I.

DETAILED DESCRIPTION OF THE INVENTION

Raf Inhibitor Compounds

The present invention provides compounds, and pharmaceutical formulations thereof, that are potentially useful in the treatment of diseases, conditions and/or disorders modulated by Raf kinases.

The term "alkyl" as used herein refers to a saturated linear or branched-chain monovalent hydrocarbon radical of one to twelve carbon atoms, wherein the alkyl radical may be optionally substituted independently with one or more substituents described below. Examples of alkyl groups include, but are not limited to, methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$), 1-heptyl, 1-octyl, cyclopropyl, cyclobutyl, cyclopentyl, cyclohexyl, cycloheptyl, and cyclooctyl.

The term "alkenyl" refers to linear or branched-chain monovalent hydrocarbon radical of two to twelve carbon atoms with at least one site of unsaturation, i.e., a carbon-carbon, sp$^2$ double bond, wherein the alkenyl radical may be optionally substituted independently with one or more substituents described herein, and includes radicals having "cis" and "trans" orientations, or alternatively, "E" and "Z" orientations. Examples include, but are not limited to, ethylene or vinyl (—CH═CH$_2$), allyl (—CH$_2$CH═CH$_2$), 1-cyclopent-1-enyl, 1-cyclopent-2-enyl, 1-cyclopent-3-enyl, 5-hexenyl (—CH$_2$CH$_2$CH$_2$CH$_2$CH═CH$_2$), 1-cyclohex-1-enyl, 1-cyclohex-2-enyl, and 1-cyclohex-3-enyl.

The term "alkynyl" refers to a linear or branched monovalent hydrocarbon radical of two to twelve carbon atoms with at least one site of unsaturation, i.e., a carbon-carbon, sp triple bond, wherein the alkynyl radical may be optionally substituted independently with one or more substituents described herein. Examples include, but are not limited to, acetylenic (—C≡CH) and propargyl (—CH$_2$C≡CH).

The term "alkylene" refers to a saturated, branched or straight chain or cyclic hydrocarbon radical of 1-18 carbon atoms, and having two monovalent radical centers derived by the removal of two hydrogen atoms from the same or two different carbon atoms of a parent alkane. Typical alkylene radicals include, but are not limited to: methylene (—CH$_2$—) 1,2-ethyl (—CH$_2$CH$_2$—), 1,3-propyl (—CH$_2$CH$_2$CH$_2$—), 1,4-butyl (—CH$_2$CH$_2$CH$_2$CH$_2$—), and the like.

The term "alkenylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkene. Typical alkenylene radicals include, but are not limited to, 1,2-ethylene (—CH═CH—).

The term "alkynylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkyne. Typical alkynylene radicals include, but are not limited to, acetylene (—C≡C—), propargyl (—CH$_2$C≡C—) and 4-pentynyl (—CH$_2$CH$_2$CH$_2$C≡C—).

"Carbocycle" and "carbocyclyl" mean a non-aromatic, saturated or unsaturated ring having 3 to 12 carbon atoms as a monocyclic ring or 7 to 12 carbon atoms as a bicyclic ring. Bicyclic carbocycles have 7 to 12 ring atoms, e.g., arranged as a bicyclo[4,5], [5,5], [5,6] or [6,6] system, or 9 or 10 ring atoms arranged as a bicyclo[5,6] or [6,6] system, or as bridged systems such as bicyclo[2.2.1]heptane, bicyclo[2.2.2]octane and bicyclo[3.2.2]nonane. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl and cyclododecyl.

"Aryl" means a monovalent aromatic hydrocarbon radical of 6-20 carbon atoms derived by the removal of one hydrogen atom from a single carbon atom of a parent aromatic ring system. Some aryl groups are represented in the exemplary structures as "Ar". Aryl includes a bicyclic radical comprising an aromatic ring with a fused non-aromatic or partially saturated ring. Typical aryl groups include, but are not limited to, radicals derived from benzene, substituted benzene, naphthalene, anthracene, biphenyl, indenyl, indanyl, 1,2-dihydronapthalene, 1,2,3,4-tetrahydronapthyl, and the like.

The term "heteroalkyl" refers to saturated linear or branched-chain monovalent hydrocarbon radical of one to twelve carbon atoms, wherein at least one of the carbon atoms is replaced with a heteroatom selected from N, O, or S, and wherein the radical may be a carbon radical or heteroatom radical (i.e., the heteroatom may appear in the middle or at the end of the radical). The heteroalkyl radical may be optionally substituted independently with one or more substituents described herein. The term "heteroalkyl" encompasses alkoxy and heteroalkoxy radicals.

The term "heteroalkenyl" refers to linear or branched-chain monovalent hydrocarbon radical of two to twelve carbon atoms, containing at least one double bond, e.g., ethenyl, propenyl, and the like, wherein at least one of the carbon atoms is replaced with a heteroatom selected from N, O, or S, and wherein the radical may be a carbon radical or heteroatom radical (i.e., the heteroatom may appear in the middle or at the end of the radical). The heteroalkenyl radical may be optionally substituted independently with one or more substituents described herein, and includes radicals having "cis" and "trans" orientations, or alternatively, "E" and "Z" orientations.

The term "heteroalkynyl" refers to a linear or branched monovalent hydrocarbon radical of two to twelve carbon atoms containing at least one triple bond. Examples include, but are not limited to, ethynyl, propynyl, and the like, wherein at least one of the carbon atoms is replaced with a heteroatom selected from N, O or S, and wherein the radical may be a carbon radical or heteroatom radical (i.e., the heteroatom may appear in the middle or at the end of the radical). The heteroalkynyl radical may be optionally substituted independently with one or more substituents described herein.

The terms "heterocycloalkyl," "heterocycle" or "hetercyclyl" refer to a saturated or partially unsaturated carbocyclic radical of 3 to 8 ring atoms in which at least one ring atom is a heteroatom selected from nitrogen, oxygen and sulfur, the remaining ring atoms being C, where one or more ring atoms may be optionally substituted independently with one or more substituent described below. The radical may be a carbon radical or heteroatom radical. The term further includes bicyclic and tricyclic fused ring systems which include a heterocycle fused one or more carbocyclic or heterocyclic rings. "Heterocycloalkyl" also includes radicals where heterocycle radicals are fused with aromatic or heteroaromatic rings. Examples of heterocycloalkyl rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl and quinolizinyl. Spiro moieties are also included within the scope of this definition. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached). An example of a heterocyclic group wherein 2 ring carbon atoms are substituted with oxo (=O) moieties is 1,1-dioxo-thiomorpholinyl. The heterocycle groups herein are unsubstituted or, as specified, substituted in one or more substitutable positions with various groups.

The term "heteroaryl" refers to a monovalent aromatic radical of 5-, 6-, or 7-membered rings which includes fused ring systems (at least one of which is aromatic) of 5-10 atoms containing at least one and up to four heteroatoms selected from nitrogen, oxygen, or sulfur. Examples of heteroaryl groups include, but are not limited to, pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl and furopyridinyl. Spiro moieties are also included within the scope of this definition. Heteroaryl groups are optionally mono-, di-, or trisubstituted with, e.g., halogen, lower alkyl, lower alkoxy, haloalkyl, aryl, heteroaryl, and hydroxy.

By way of example and not limitation, carbon bonded heterocycles and heteroaryls are bonded at position 2, 3, 4, 5, or 6 of a pyridine, position 3, 4, 5 or 6 of a pyridazine, position 2, 4, 5, or 6 of a pyrimidine, position 2, 3, 5 or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7 or 8 of an isoquinoline. Examples of carbon bonded heterocycles include, but are not limited to, 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl or 5-thiazolyl.

By way of example and not limitation, nitrogen bonded heterocycles and heteroaryls are bonded at position I of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole or β-carboline. Examples of nitrogen bonded heterocycles include 1-aziridyl, 1-azetedyl, 1-pyrrolyl, 1-imidazolyl, 1-pyrazolyl and 1-piperidinyl.

"Substituted alkyl", "substituted aryl", "substituted heterocyclyl" and "substituted cycloalkyl" mean alkyl, aryl, heterocyclyl and cycloalkyl respectively, in which one or more hydrogen atoms are each independently replaced with a substituent. Typical substituents include, but are not limited to, F, Cl, Br, I, OH, OR, R, =O, =S, =NR, =N$^+$(O)(R), =N(OR), =N$^+$(O)(OR), =N—NRR', —C(=O)R, —C(=O)OR, —C(=O)NRR', —NRR', —N$^+$RR'R", —N(R)C(=O)R', —N(R)C(=O)OR', —N(R)C(=O)NR'R", —SR, —OC(=O)R, —OC(=O)OR, —OC(=O)NRR', —OS(O)$_2$(OR), —OP(=O)(OR)$_2$, —OP(OR)$_2$, —P(=O)(OR)$_2$, —P(=O)(OR)NR'R", —S(O)R, —S(O)$_2$R, —S(O)$_2$NR, —S(O)(OR), —S(O)$_2$(OR), —SC(=O)R, —SC(=O)OR, =O and —SC(=O)NRR'; where each R, R' and R" is independently selected from H, $C_1$-$C_{10}$ alkyl, $C_1$-$C_{10}$ alkenyl, $C_1$-$C_{10}$ alkynyl, $C_6$-$C_{20}$ aryl and $C_2$-$C_{20}$ heterocycle. Alkenyl, alkynyl, alkylene, alkenylene and alkynylene groups as described above may also be similarly substituted.

In one embodiment the invention also provides compounds of formula I wherein:

X is NR$^5$, CH$_2$ or CO;

R$^1$ is $C_1$-$C_{10}$ alkyl, $C_2$-$C_{10}$ alkenyl, $C_2$-$C_{10}$ alkynyl, cycloalkyl, heterocycloalkyl, $Z_n$-aryl, heteroaryl, —C(=O)R$^{12}$, —C(=O)OR$^{12}$, —C(=O)NR$^{12}$R$^{13}$, —NR$^{12}$R$^{13}$, —N(R$^{13}$)C(=O)R$^{12}$, —N(R$^{13}$)C(=O)OR$^{12}$, —N(R$^{12}$)C(=O)NR$^{13}$R$^{14}$, —S(O)R$^{14}$, —S(O)$_2$R$^{14}$ or —S(O)$_2$NR$^{12}$R$^{13}$, wherein said alkyl, alkenyl, alkynyl, cycloalkyl, heterocycloalkyl, aryl and heteroaryl portions are optionally substituted with one or more groups independently selected from F, Cl, Br, I, NO$_2$, oxo (with the proviso that it is not on said aryl or heteroaryl) alkyl, $Z_n$-aryl, $Z_n$-heterocycloalkyl, $Z_n$-heteroaryl, $Z_n$-CN, $Z_n$-OR$^{12}$, $Z_n$-C(O)R$^{12}$, $Z_n$-C(O)OR$^{12}$, $Z_n$-C(O)-heterocycloalkyl, $Z_n$-NR$^{12}$R$^{15}$, $Z_n$-NR$^{12}$C(O)R$^{13}$, $Z_n$-NR$^{12}$C(O)OR$^{13}$, $Z_n$-SR$^{12}$, $Z_n$-SOR$^{12}$, $Z_n$-SO$_2$R$^{12}$, $Z_n$-O—($C_1$-$C_6$ alkyl)-C(O)NR$^{12}$R$^{13}$, $Z_n$-O—($C_1$-$C_6$ alkyl)-C(O)OR$^{12}$, $Z_n$-O—($C_1$-$C_6$ alkyl)-heterocycloalkyl, $Z_n$-C(O)NR$^{12}$R$^{13}$, $Z_n$-NR$^{12}$-($C_1$-$C_6$ alkyl)-C(O)NR$^{12}$R$^{13}$, $Z_n$-NR$^{12}$-($C_1$-$C_6$ alkyl)-C(O)OR$^{12}$, $Z_n$-NR$^{12}$—

($C_2$-$C_6$ alkyl)-OC(O)NR$^{12}$R$^{13}$, $Z_n$-NR$^{12}$C(=O)NR$^{13}$ and $Z_n$-NR$^{12}$—($C_2$-$C_6$ alkyl)-NR$^{12}$C(O)NR$^{12}$R$^{13}$;

R$^2$, R$^3$ and R$^4$ are independently selected from H, F, Cl, Br, I, —C(=O)R$^{12}$, —C(=O)OR$^{12}$, —C(=O)NR$^{12}$R$^{13}$, —NR$^{12}$R$^{14}$, —OR$^{12}$, —OC(=O)R$^{12}$, —OC(=O)OR$^{12}$, —OC(=O)NR$^{12}$R$^{13}$, —NR$^{12}$C(O)—R$^{13}$, —NR$^{12}$—C(O)NR$^{13}$R$^{14}$ and —NR$^{12}$—C(O)OR$^{13}$;

R$^5$ is H, $C_1$-$C_{10}$ alkyl, $C_2$-$C_{10}$ alkenyl, $C_2$-$C_{10}$ alkynyl, $C_6$-$C_{20}$ cycloalkyl, $C_6$-$C_{20}$ heterocycloalkyl, —C(O)R$^{12}$ or —C(O)OR$^{12}$, wherein said alkyl, alkenyl, alkynyl, cycloalkyl and heterocycloalkyl portions are optionally substituted with one or more groups independently selected from halogen, OH, O-alkyl, and amino;

R$^6$ is

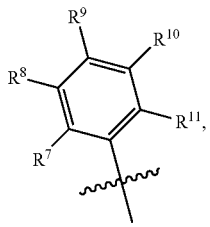

wherein (i) R$^7$ and R$^8$ form a 5 or 6 membered fused carbocyclic ring substituted with =Y, and R$^9$, R$^{10}$ and R$^{11}$ are independently selected from H, F, Cl, Br, and I, or (ii) R$^8$ and R$^9$ form a 5 or 6 membered fused carbocyclic ring substituted with =Y, and R$^7$, R$^{10}$ and R$^{11}$ are independently selected from H, F, Cl, Br, and I;

Y is O or N—OH;

R$^{12}$, R$^{13}$ and R$^{14}$ are independently selected from H, alkyl, alkenyl, alkynyl, heteroalkyl, heteroalkenyl, heteroalkynyl, cycloalkyl, heterocycloalkyl, aryl and heteroaryl, wherein said alkyl, alkenyl, alkynyl, heteroalkyl, heteroalkenyl, heteroalkynyl, cycloalkyl, heterocycloalkyl, aryl and heteroaryl are optionally substituted with one or more groups independently selected from halogen, OH, O-alkyl, amino, alkylamino and dialkylamino;

R$^{15}$ is H, —SO$_2$-alkyl, —SO$_2$NR$^{13}$R$^{14}$, ($C_1$-$C_6$ alkyl)-OH, —C(O)O-alkyl, alkyl, alkenyl, alkynyl, heteroalkyl, heteroalkenyl, heteroalkynyl, cycloalkyl, heterocycloalkyl, aryl or heteroaryl, wherein said alkyl, alkenyl, alkynyl, heteroalkyl, heteroalkenyl, heteroalkynyl, cycloalkyl, heterocycloalkyl, aryl and heteroaryl portions are optionally substituted with one or more groups independently selected from halogen, OH, O-alkyl, and amino;

Z is alkylene having from 1 to 4 carbons, or alkenylene or alkynylene each having from 2 to 4 carbons, wherein said alkylene, alkenylene and alkynylene are optionally substituted with one or more groups independently selected from halogen, OH, O-alkyl, and amino; and n is 0, 1, 2, 3 or 4.

Exemplary embodiments of R$^1$ for compounds of Formula I include, but are not limited to, 2-pyridyl, 3-pyridyl, 4-pyridyl, 2-imidazolyl, 4-imidazolyl, 3-pyrazolyl, 4-pyrazolyl, 2-pyrrolyl, 3-pyrrolyl, 2-thiazolyl, 4-thiazolyl, 5-thiazolyl, 3-pyridazinyl, 4-pyridazinyl, 5-pyridazinyl, 2-pyrimidinyl, 5-pyrimidinyl, 6-pyrimidinyl, 2-pyrazinyl, 2-oxazolyl, 4-oxazolyl, 5-oxazolyl, 2-furanyl, 3-furanyl, 2-thienyl, 3-thienyl, phenyl, 3-indolyl, and substituted forms thereof, and shown as:

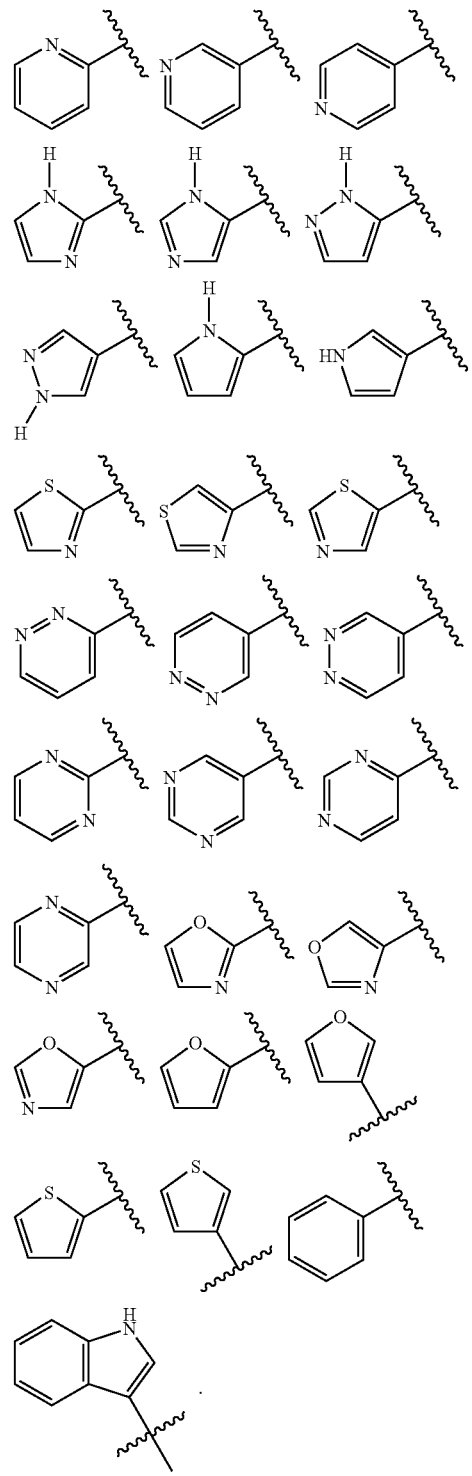

Exemplary embodiments of R$^1$ for compounds of Formula I include, but are not limited to, aryl optionally substituted with one or more hydroxymethyl, methylaminocarbonylmethoxy, amino, 2-(dimethylamino)-ethylaminocarbonyl, methoxycarbonylmethoxy, ethylamino, acylamino, dimethylaminocarbonylmethoxy, carboxymethoxy, hydroxy, aminocarbonylmethoxy, methoxy, fluoro, methyl, methylami nocarbonyl, morpholinocarbonylmethoxy, N-(2-methoxyethyl)-N-methylaminocarbonylmethoxy, isopropylaminocarbonyl, methoxycarbonyl, carboxy, acylaminomethyl, nitro, methylsulfonylamino, morpholino, methylsulfonyl, dimethylamino, cyano, methylthio, tert-butoxycarbonylamino, N-(2-hydroxyethyl)methylamino, aminomethyl, morpholinocarbonyl, 2-methoxyethoxy, pyrazol-1-yl, N-(tert-butoxycarbonyl)ethylamino, 3,5-dimethylpyrazol-1-yl, or N,N-di(methylsulfonyl)amino.

Exemplary embodiments of $R^1$ for compounds of Formula I include, but are not limited to, phenyl optionally substituted with one or more hydroxymethyl, methylaminocarbonylmethoxy, amino, 2-(dimethylamino)-ethylaminocarbonyl, methoxycarbonylmethoxy, ethylamino, acylamino, dimethylaminocarbonylmethoxy, carboxymethoxy, hydroxy, aminocarbonylmethoxy,methoxy, fluoro, methyl, methylaminocarbonyl, morpholinocarbonylmethoxy, N-(2-methoxyethyl)-N-methylaminocarbonylmethoxy, isopropylaminocarbonyl, methoxycarbonyl, carboxy, acylaminomethyl, nitro, methylsulfonylamino, morpholino, methylsulfonyl, dimethylamino, cyano, methylthio, tert-butoxycarbonylamino, N-(2-hydroxyethyl)methylamino, aminomethyl, morpholinocarbonyl, 2-methoxyethoxy, pyrazol-1-yl, N-(tert-butoxycarbonyl)ethylamino, 3,5-dimethylpyrazol-1-yl, or N,N-di(methylsulfonyl)amino.

Exemplary embodiments of $R^1$ for compounds of Formula I include, but are not limited to, 1-methyl-1H-indol-3-yl, 2-furyl, 2-thienyl, 2-thiazoyl, 1-methylpyrazol-4-yl, 3-furyl, 6-aminopyrid-3-yl1-methylpyrrol-2-yl, 1-ethyl-2-oxo-1,2-dihydropyrid-5-yl, 1-(pyrid-3-yl)pyrrol-2-yl, 3-thienyl, 5-thiazolyl, 5-cyano-6-methylthiopyrid-2-yl, 6-methoxypyrid-3-yl, 2-pyrrolyl, 6-(tert-butoxycarbonylamino)pyrid-3-yl, 1,2,3thiadiazole-4-yl, 2-quinolyl, 3-pyridyl, 5-methoxypyrid-2-yl, 2-hydroxypropyl, benzyl, 2-oxo-1,2-dihydropyrid-5-yl, 2-(methoxycarbonyl)ethyl, 1-(2-cyanoethyl)pyrrol-2-yl, 3-piperidinyl, 2-oxo-1,2-dihydropyrid-4-yl, 3-aminopropyl, methyl, 4-methoxybenzyl, 1-(2-thiazolyl)pyrrol-2-yl, 2-tetrahydrofuranyl, 1-(tertbutoxycarbonyl)piperidin-3-yl, 2-aminoethyl, 1-(4-methylpyrid-2-yl))pyrrol-2-yl, 1-(tertbutoxycarbonyl)piperidin-4-yl, or 4-piperidyl.

Exemplary embodiments of compounds of Formula I include Formulas Ia and Ib:

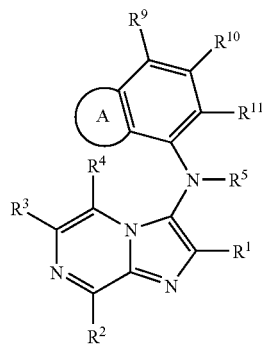

Ia

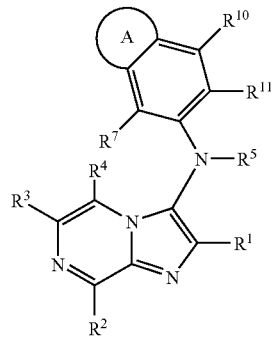

Ib where A is a 5 or 6 membered fused carbocyclic ring substituted with =Y.

Exemplary embodiments of compounds of Formula I also include Formulas Ic-Ip:

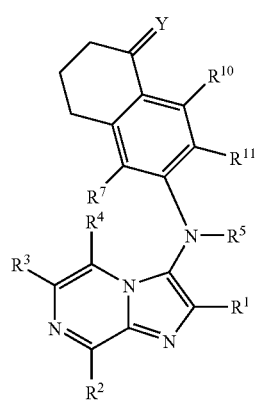

Ic

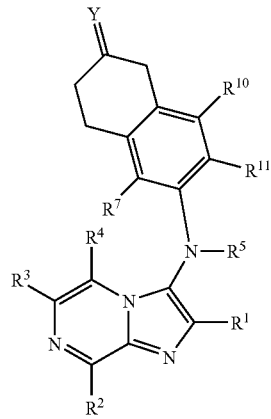

Id

-continued
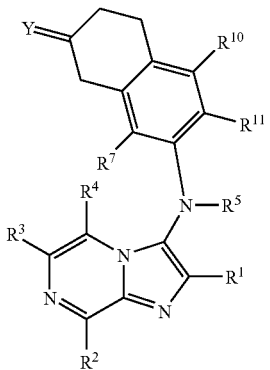
Ie
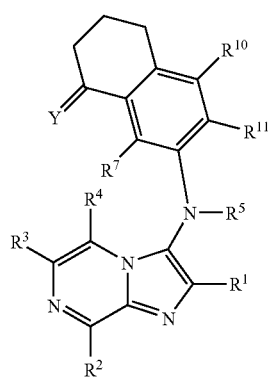
If
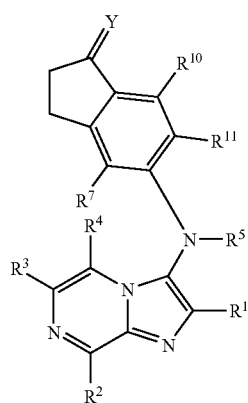
Ig
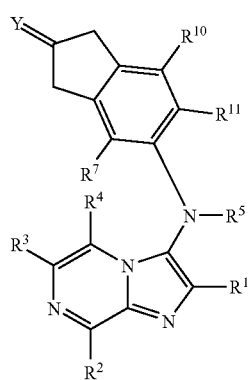
Ih
-continued
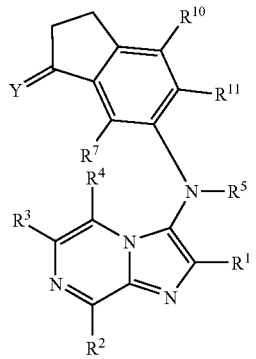
Ii
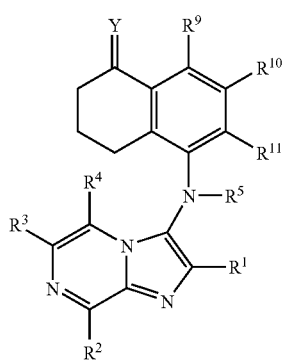
Ij
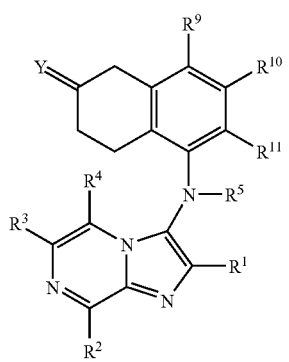
Ik
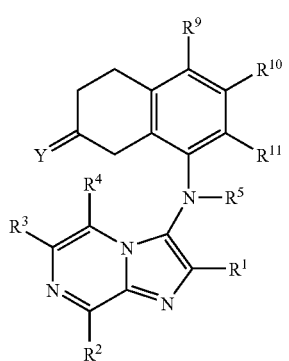
Il -continued
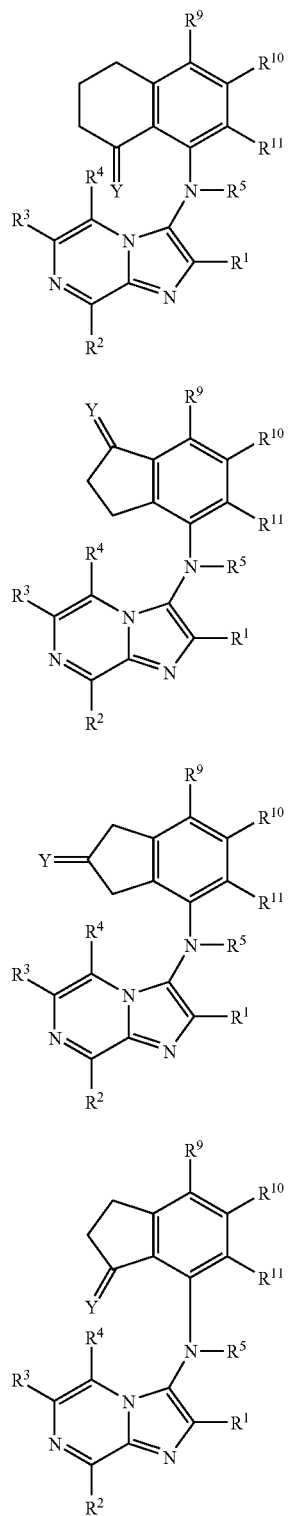
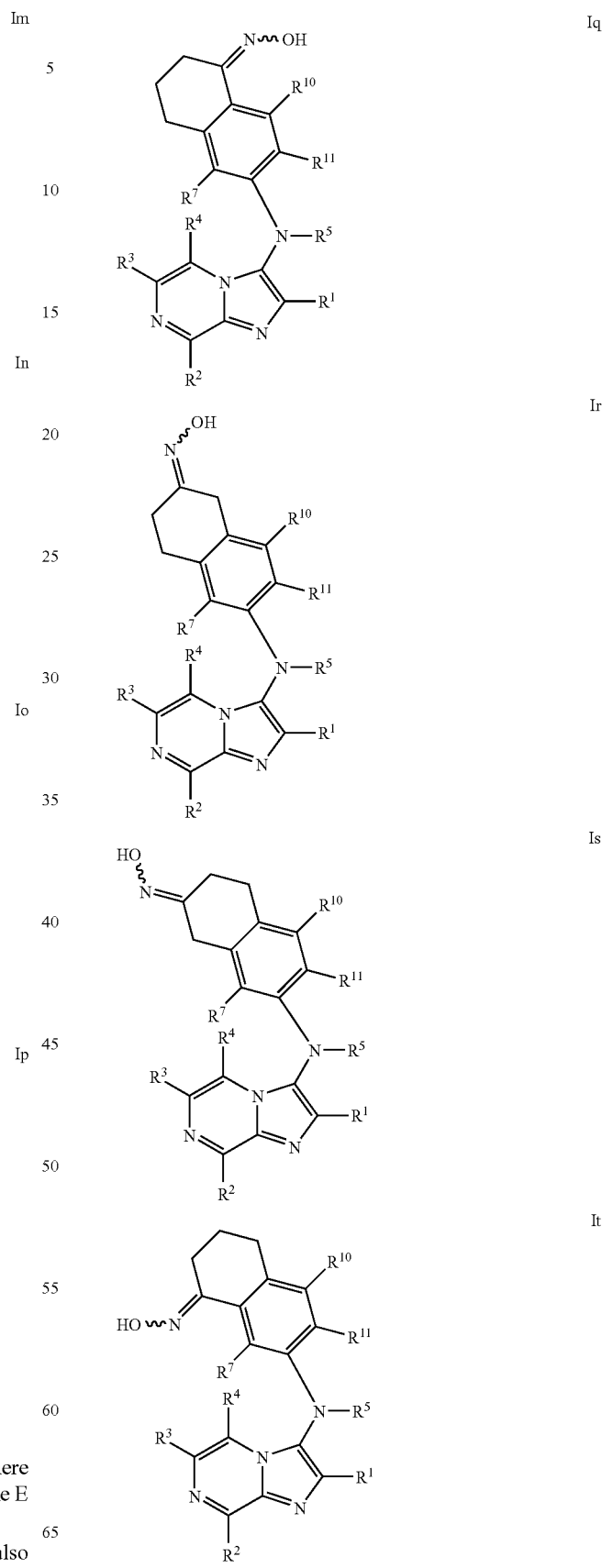
In embodiments of compounds of Formula Ic-Ip where =Y is =N—OH, the oxime moiety can exist as either the E or Z isomer or as a mixture of both.
Exemplary embodiments of compounds of Formula I also include Formulas Iq-Idd:

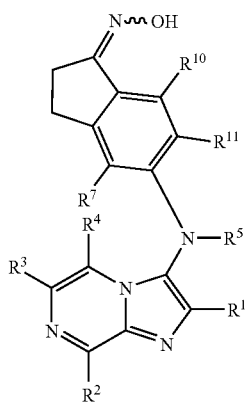
Iu
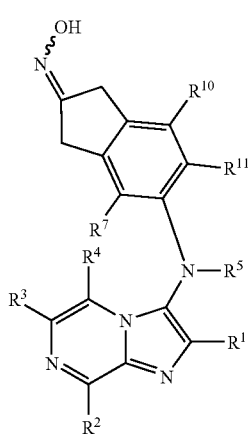
Iv
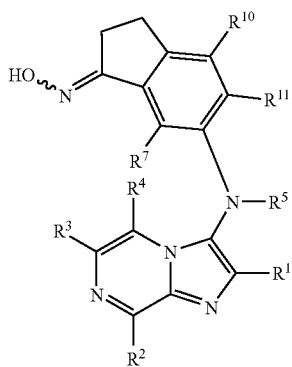
Iw
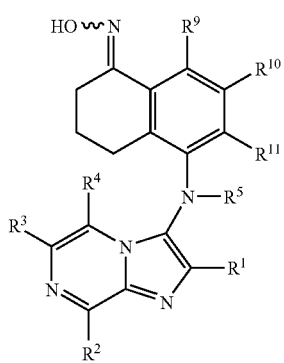
Ix
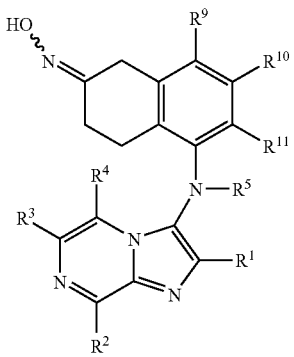
Iy
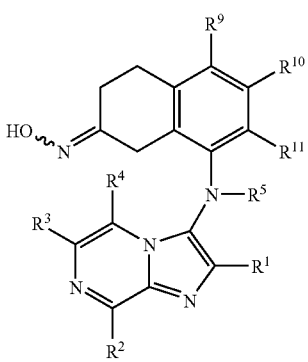
Iz
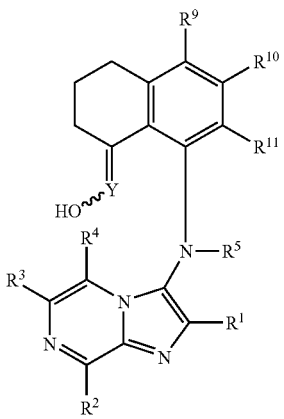
Iaa
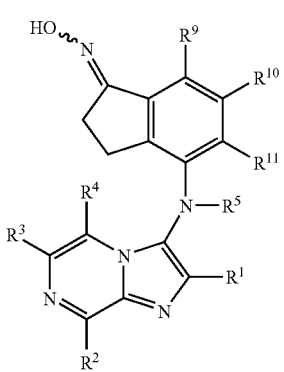
Ibb

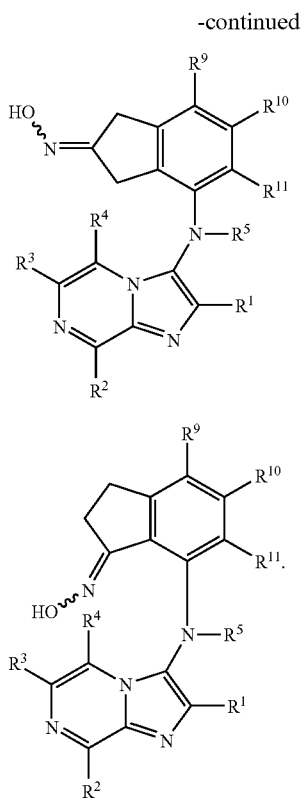

In embodiments of compounds of Formula Iq-Idd where =Y is =N—OH, the oxime moiety can exist as either the E or Z isomer or as a mixture of both.

In addition to compounds of Formula I, the invention also includes solvates, pharmaceutically acceptable prodrugs, pharmaceutically active metabolites, and pharmaceutically acceptable salts of such compounds.

The term "solvate" refers to an aggregate of a molecule with one or more solvent molecules.

The term "prodrug" as used herein refers to a precursor or derivative form of a compound of Formula I that is less cytotoxic to tumor cells compared to the parent compound of Formula I and is capable of being enzymatically or hydrolytically activated or converted into the more active parent form. See, e.g., Wilman, "Prodrugs in Cancer Chemotherapy" Biochemical Society Transactions, 14, pp. 375-382, 615th Meeting Belfast (1986) and Stella, et al., "Prodrugs: A Chemical Approach to Targeted Drug Delivery," *Directed Drug Delivery*, Borchardt, et al., (ed.), pp. 247-267, Humana Press (1985). Prodrugs of this invention include, but are not limited to, phosphate-containing prodrugs, thiophosphate-containing prodrugs, sulfate-containing prodrugs, peptide-containing prodrugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Prodrugs also include compounds of Formula I wherein an amino acid residue, or a chain of two or more (e.g., two, three or four) amino acid residues, is covalently joined through an amide or ester bond to a free amino, hydroxy or carboxylic acid group of a compound of Formula I. The amino acid residues include, but are not limited to, the 20 naturally occurring amino acids commonly designated by three letter symbols, and also include 4-hydroxyproline, hydroxylysine, demosine, isodemosine, 3-methylhistidine, norvaline, beta-alanine, gamma-aminobutyric acid, cirtulline, homocysteine, homoserine, omithine and methionine sulfone.

Additional types of prodrugs are also encompassed. For instance, free carboxyl groups of compounds of Formula I can be derivatized as amides or alkyl esters. As another example, compounds of this invention comprising free hydroxy groups may be derivatized as prodrugs by converting the hydroxy group groups including to a phosphate ester, hemisuccinate, dimethylaminoacetate, or phosphoryloxymethyloxycarbonyl, as outlined in *Advanced Drug Delivery Reviews,* 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including, but not limited to, ether, amine and carboxylic acid functionalities, or where the acyl group is an amino acid ester as described above, are also encompassed. Prodrugs of this type are described in *J. Med. Chem.,* 1996, 39, 10. More specific examples include replacement of the hydrogen atom of the alcohol group with a group such as ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino ($C_1$-$C_4$)alkanoyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1$-$C_6)alkyl)_2$ or glycosyl (the radical resulting from the removal of a hydroxyl group of the hemiacetal form of a carbohydrate).

Free amines of compound of Formula I can also be derivatized as amide, sulfonamide or phosphonamide prodrugs. All of these prodrug moieties may incorporate groups including, but not limited to, ether, amine and carboxylic acid functionalities. For example, a prodrug can be formed by the replacement of a hydrogen atom in the amine group with a group such as R-carbonyl, RO-carbonyl, NRR'-carbonyl where R and R' are each independently ($C_1$-$C_{10}$)alkyl, ($C_3$-$C_7$)cycloalkyl, benzyl, or R-carbonyl is a natural α-aminoacyl or natural α-aminoacyl-natural α-aminoacyl, —C(OH)C(O)OY wherein Y is H, ($C_1$-$C_6$)alkyl or benzyl, —C($OY_0$)$Y_1$ wherein $Y_0$ is ($C_1$-$C_4$) alkyl and $Y_1$ is ($C_1$-$C_6$)alkyl, carboxy ($C_1$-$C_6$)alkyl, amino($C_1$-$C_4$)alkyl or mono-N— or di-N,N-($C_1$-$C_6$)alkylaminoalkyl, —C($Y_2$)$Y_3$ wherein $Y_2$ is H or methyl and $Y_3$ is mono-N— or di-N,N-($C_1$-$C_6$)alkylamino, morpholino, piperidin-1-yl or pyrrolidin-1-yl.

A "metabolite" is a product produced through metabolism in the body of a specified compound or salt thereof. Metabolites of a compound may be identified using routine techniques known in the art and their activities determined using tests such as those described herein.

A "pharmaceutically acceptable salt," as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the inventive compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the inventive compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The phrase "pharmaceutically acceptable" indicates that the substance or composition must be compatible chemically and/or toxicologically, with the other ingredients comprising a formulation, and/or the mammal being treated therewith.

The compounds of the invention may contain asymmetric or chiral centers, and therefore exist in different stereoisomeric forms. The term "chiral" refers to molecules which have the property of non-superimposability of the mirror image partner, while the term "achiral" refers to molecules which are superimposable on their mirror image partner. It is intended that all stereoisomeric forms of the compounds of the invention, including but not limited to, diastereomers, enantiomers and atropisomers, as well as mixtures thereof such as racemic mixtures, form part of the present invention. The term "stereoisomers" refers to compounds which have identical chemical constitution, but differ with regard to the arrangement of the atoms or groups in space. "Diastereomer" refers to a stereoisomer with two or more centers of chirality and whose molecules are not mirror images of one another. Diastereomers have different physical properties, e.g., melting points, boiling points, spectral properties and reactivities. Mixtures of diastereomers may separate under high resolution analytical procedures such as electrophoresis and chromatography. "Enantiomers" refer to two stereoisomers of a compound which are non-superimposable mirror images of one another. Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

In addition, the present invention embraces all geometric and positional isomers. For example, if a compound of the present invention incorporates a double bond or a fused ring, the cis- and trans-forms, as well as mixtures thereof, are embraced within the scope of the invention. Both the single positional isomers and mixture of positional isomers, e.g., resulting from the N-oxidation of the pyrimidine and pyrazine rings, are also within the scope of the present invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The compounds of the present invention may exist in unsolvated as well as solvated forms with pharmaceutically acceptable solvents such as water, ethanol, and the like, and it is intended that the invention embrace both solvated and unsolvated forms.

It is also possible that the compounds of the present invention may exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The present invention also embraces isotopically-labeled compounds of the present invention which are identical to those recited herein, but for the fact that one or more atoms are replaced by an atom having an atomic mass or mass number different from the atomic mass or mass number usually found in nature. All isotopes of any particular atom or element as specified is contemplated within the scope of the compounds of the invention, and their uses. Exemplary isotopes that can be incorporated into compounds of the invention include isotopes of hydrogen, carbon, nitrogen, oxygen, phosphorus, sulfur, fluorine, chlorine and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$ and $^{125}I$. Certain isotopically-labeled compounds of the present invention (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are useful for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$ and $^{18}F$ are useful for positron emission tomography (PET) studies to examine substrate receptor occupancy. Isotopically labeled compounds of the present invention can generally be prepared by following procedures analogous to those disclosed in the Schemes and/or in the Examples herein below, by substituting an isotopically labeled reagent for a non-isotopically labeled reagent.

Synthesis of Raf Inhibitor Compounds

Compounds of Formula I may be synthesized by synthetic routes that include processes analogous to those well-known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, Reagents for Organic Synthesis, v. 1-19, Wiley, N.Y. (1967-1999 ed.), or Beilsteins Handbuch der organischen Chemie, 4, Aufl. ed. Springer-Verlag, Berlin, including supplements (also available via the Beilstein online database).

For illustrative purposes, Schemes 1 and 2 depicted below provide potential routes for synthesizing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

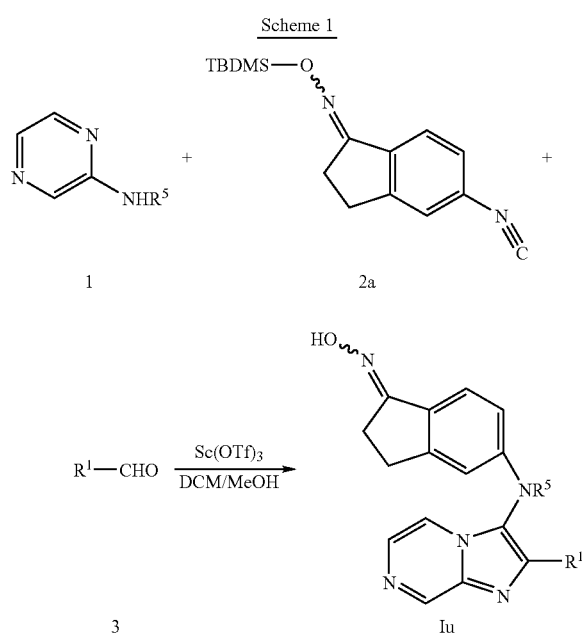

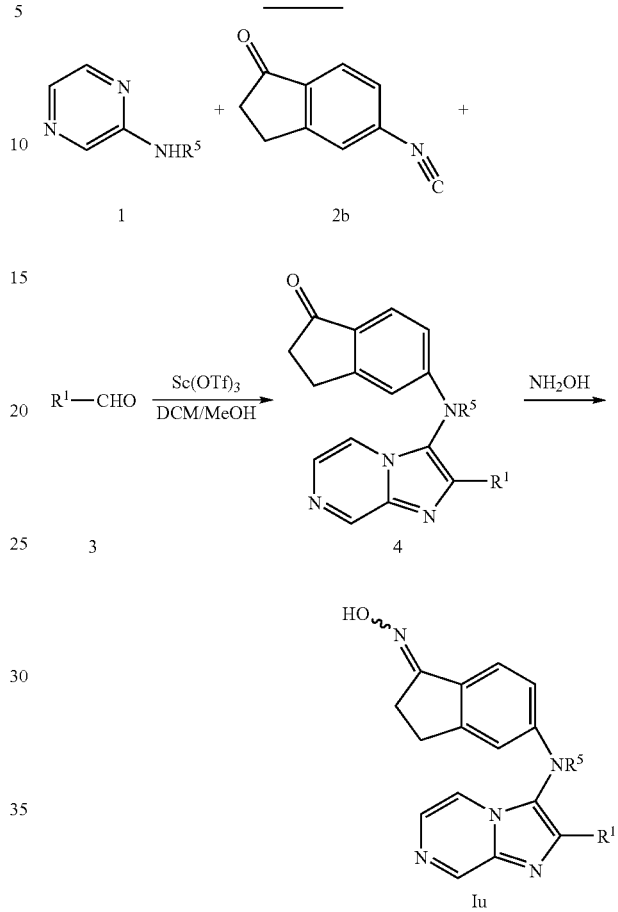

A general procedure for the synthesis of compounds of Formula Iu as shown in Schemes 1 and 2 comprises a [4+1] cyclization reaction (see, for example see Blackburn, C., et al., *Tet. Letters,* 39 (1998), 3635-3638 and Groebke, K. and Mehlin, F., *Synlet,* (1998), 661-663) involving the appropriate pyrazine (1), isonitrile (2a or 2b) and aldehyde (3) components. The reaction can be carried out with either oxime derivative as shown in Scheme 1 to provide the desired oxime, or with the ketone derivative as shown in Scheme 2, where the imidazopyrazine intermediate 4 is converted to the oxime Iu by treatment with hydroxylamine. All compounds were characterized by proton NMR and MS.

Schemes 3 and 4 show additions routes to compounds of the present invention. Condensation of pyrazine derivatives with alkyl or aryl functionalized alpha-halo ketones can be carried out to prepare the 2,3-substituted imidazopyrazines (see Rimoli, M. G.,et al., *Eur. J. Med. Chem.,* 32 (1997), 195-203 and Sablayrolles, C., et al., *J. Med. Chem.,* 27 (1984), 206-212). Bromination of the methyl group at C3 can be carried out with NBS to afford the intermediate bromide that can be coupled with boronic acids in a Suzuki-type coupling reaction to prepare the functionalized imidazopyrazines.

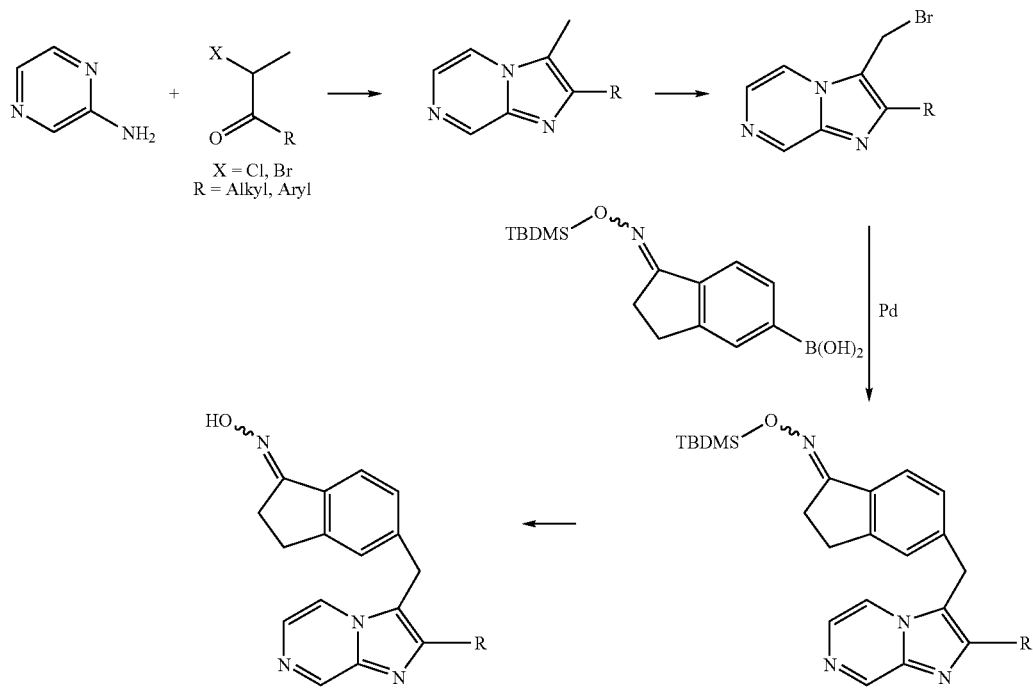

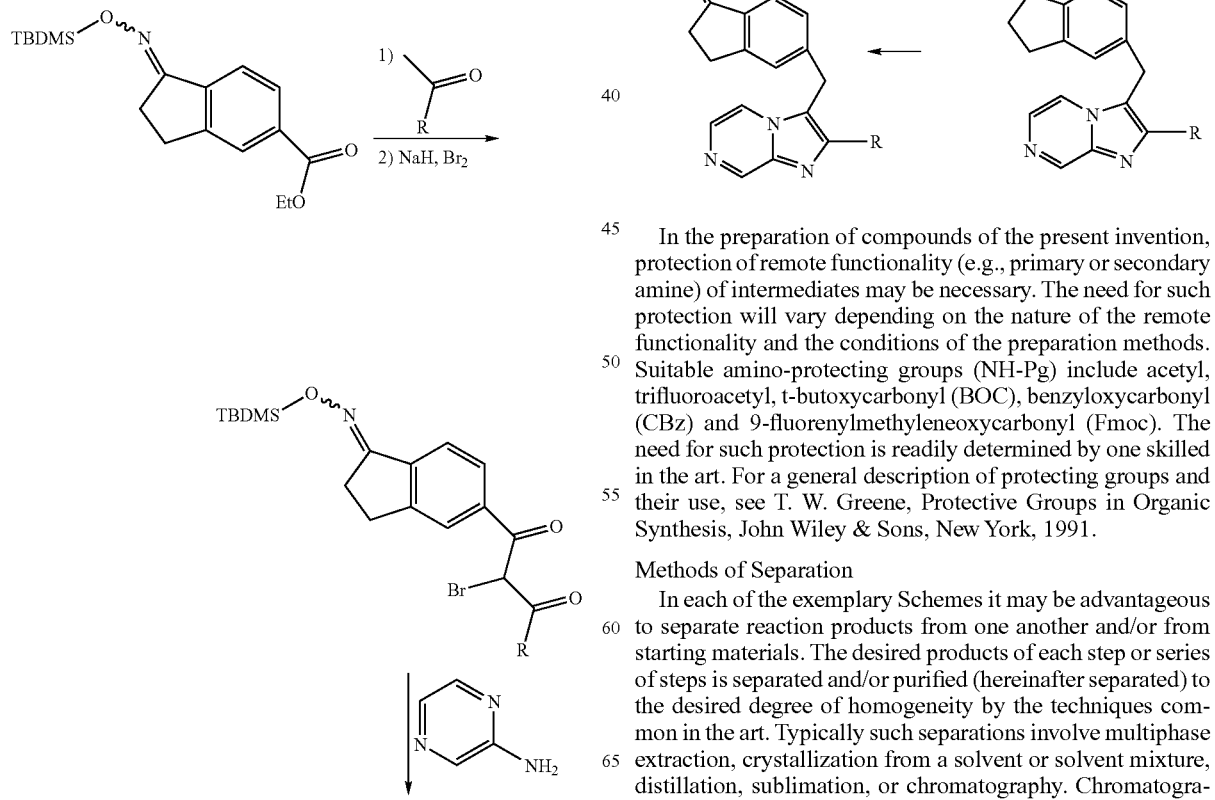

In the preparation of compounds of the present invention, protection of remote functionality (e.g., primary or secondary amine) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

Methods of Separation

In each of the exemplary Schemes it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point and molecular weight in distillation and sublimation, presence or absence of polar functional groups in chromatography, stability of materials in acidic and basic media in multiphase extraction, and the like. One skilled in the art will apply techniques most likely to achieve the desired separation.

Diastereomeric mixtures can be separated into their individual diastereoisomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., (1975) J. Chromatogr., 113(3):283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III. (1982) J. Org. Chem. 47:4165), of the racemic mixture, and analyzing the NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase ("Chiral Liquid Chromatography" (1989) W. J. Lough, Ed., Chapman and Hall, New York; Okamoto, (1990) J. of Chromatogr. 513:375-378). Enriched or purified enantiomers can be distinguished by methods used to distinguish other chiral molecules with asymmetric carbon atoms, such as optical rotation and circular dichroism.

Administration of Compounds of Formula I

The compounds of the invention may be administered by any route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal. For local immunosuppressive treatment, the compounds may be administered by intralesional administration, including perfusing or otherwise contacting the graft with the inhibitor before transplantation. It will be appreciated that the preferred route may vary with for example the condition of the recipient. Where the compound is administered orally, it may be formulated as a pill, capsule, tablet, etc. with a pharmaceutically acceptable carrier or excipient. Where the compound is administered parenterally, it may be formulated with a pharmaceutically acceptable parenteral vehicle and in a unit dosage injectable form, as detailed below.

Pharmaceutical Formulations

As indicated, the compounds of Formula I and the pharmaceutically acceptable salts and prodrugs thereof are useful in the treatment and/or prophylaxis of: disorders associated with neuronal degeneration resulting from ischemic events, cancer, chronic neurodegneration, pain, migraine and cardiac hypertrophy. Accordingly, another aspect of the invention provides methods of preventing or treating a hyperproliferative disorder, neurodegeneration, cardiac hypertrophy, pain, migraine or a neurotraumatic disease or event, by administering to a mammal in need of such treatment an effective amount of a compound of Formula I, or a composition containing a compound of Formula I. In addition, the present invention further provides a pharmaceutical composition, i.e., formulation, comprising a therapeutically effective amount of a compound of Formula I. According to a further aspect of the invention there is provided the use of a compound of Formula I or a pharmaceutically acceptable salt or prodrug thereof in the manufacture of a medicament for the prophylactic or therapeutic treatment of any disease state in a human, or other mammal, which is exacerbated or caused by a hyperproliferative disorder, neurodegeneration, cardiac hypertrophy, pain, migraine or a neurotraumatic disease or event.

Neurotraumatic diseases/events as defined herein include both open or penetrating head trauma, such as caused by surgery, or a closed head trauma injury, such as caused by an injury to the head region. Also included within this definition is ischemic stroke, particularly to the brain area, transient ischemic attacks following coronary by-pass and cognitive decline following other transient ischemic conditions.

Ischemic stroke may be defined as a focal neurologic disorder that results from insufficient blood supply to a particular brain area, usually as a consequence of an embolus, thrombi, or local atheromatous closure of the blood vessel. Roles for stress stimuli (such as anoxia), redox injury, excessive neuronal excitatory stimulation and inflammatory cytokines in this area has been emerging and the present invention provides a means for the potential treatment of these injuries. Relatively little treatment, for an acute injury such as these has been available.

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small- cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

The terms "treat" and "treatment" refer to both therapeutic treatment and prophylactic or preventative measures, wherein the object is to reverse, prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilization (i.e., not worsening) of the state of the disease, delay or slowing of disease progression, amelioration or palliation of the disease state and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented. Thus the terms "treating", "treat", or "treatment" embrace both preventative, i.e., prophylactic and palliative treatment.

The phrase "therapeutically effective amount" means an amount of a compound of Formula I that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, a therapeutically effective amount of the compound of Formula I may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent a compound of Formula I may prevent growth and/or kill existing cancer cells, it may be cytostatic and/or cytotoxic. For cancer therapy, efficacy can be measured, for example, by assessing the time to disease progression (TTP) and/or determining the response rate (RR).

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more of the excipients described above. The compound of the present invention is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations of the compounds of the present invention may be prepared for various routes and types of administration. For example, a compound of Formula I having the desired degree of purity may optionally be mixed with pharmaceutically acceptable diluents, carriers, excipients or stabilizers (Remington's Pharmaceutical Sciences (1980) 16th edition, Osol, A. Ed.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The inhibitory compound for use herein is preferably sterile. In particular, formulations to be used for in vivo administration must be sterile. Such sterilization is readily accomplished by filtration through sterile filtration membranes.

The compound ordinarily can be stored as a solid composition, a lyophilized formulation or as an aqueous solution.

The pharmaceutical compositions of the invention will be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to prevent, ameliorate, or treat the coagulation factor mediated disorder. Such amount is preferably below the amount that is toxic to the host or renders the host significantly more susceptible to bleeding.

As a general proposition, the initial pharmaceutically effective amount of the inhibitor administered parenterally per dose will be in the range of about 0.01-100 mg/kg, namely about 0.1 to 20 mg/kg of patient body weight per day, with the typical initial range of compound used being 0.3 to 15 mg/kg/day.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980). A "liposome" is a small vesicle composed of various types of lipids, phospholipids and/or surfactant which is useful for delivery of a drug (such as the Raf inhibitors disclosed herein and, optionally, a chemotherapeutic agent) to a mammal. The components of the liposome are commonly arranged in a bilayer formation, similar to the lipid arrangement of biological membranes.

Sustained-release preparations of compounds of Formula I may be prepared. Suitable examples of sustained-release preparations include semipermeable matrices of solid hydrophobic polymers containing a compound of Formula I, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid.

The formulations include those suitable for the administration routes detailed herein. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of a compound of Formula I suitable for oral administration may be prepared as discrete units such as pills, capsules, cachets or tablets each containing a predetermined amount of a compound of Formula I.

Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g., gelatin capsules, syrups or elixirs may be prepared for oral use. Formulations of compounds of Formula I intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

For treatment of the eye or other external tissues e.g., mouth and skin, the formulations are preferably applied as a topical ointment or cream containing the active ingredient(s) in an amount of, for example, 0.075 to 20% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of the emulsions of this invention may be constituted from known ingredients in a known manner. While the phase may comprise merely an emulsifier, it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of the invention contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

The pharmaceutical compositions of compounds of Formula I may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis disorders as described below.

Formulations suitable for vaginal administration may be presented as pessaries; tampons, creams, gels, pastes, foams or spray formulations containing in addition to the active ingredient such carriers as are known in the art to be appropriate.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

The compounds of Formula I and pharmaceutically acceptable derivatives thereof, may be employed alone or in combination with other therapeutic agents for the treatment of the above-mentioned conditions. In particular, a compound of Formula I may be combined in a pharmaceutical combination formulation, or dosing regimen as combination therapy, with a second compound that has anti-hyperproliferative properties or that is useful for treating a hyperproliferative disorder (e.g., cancer). The second compound of the pharmaceutical combination formulation or dosing regimen preferably has complementary activities to the compound of Formula I such that they do not adversely affect each other. Such molecules are suitably present in combination in amounts that are effective for the purpose intended.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and may be lowered due to the combined action (synergy) of the newly identified agent and other chemotherapeutic agents or treatments.

The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes. In general, during alternation therapy, an effective dosage of each active ingredient is administered sequentially, i.e., serially, whereas in combination therapy, effective dosages of two or more active ingredients are administered together.

In a particular embodiment, in anti-cancer therapy, a compound of Formula I may be combined with other chemotherapeutic, hormonal or antibody agents as well as combined with surgical therapy and radiotherapy. Combination therapies according to the present invention thus comprise the administration of at least one compound of Formula I or a pharmaceutically acceptable derivative thereof, and the use of at least one other cancer treatment method. Preferably, combination therapies according to the present invention comprise the administration of at least one compound of Formula I or a pharmaceutically acceptable derivative thereof, and at least one other pharmaceutically active chemotherapeutic agent. These include existing and prospective chemotherapeutic agents. The compound(s) of Formula I and the other pharmaceutically active chemotherapeutic agent(s) may be administered together in a unitary pharmaceutical composition or separately and, when administered separately this may occur simultaneously or sequentially in any order. Such sequential administration may be close in time or remote in time. The amounts of the compound(s) of Formula I and the other pharmaceutically active chemotherapeutic agent(s) and the relative timings of administration will be selected in order to achieve the desired combined therapeutic effect.

Pharmaceutically active chemotherapeutic agents which can be useful in combination with a compound of Formula I or a pharmaceutically acceptable derivative thereof, include but are not limited to the following:

1) cell cycle specific anti-neoplastic agents include, but are not limited to, diterpenoids such as paclitaxel and its analog docetaxel; tubulin poisons such as taxo/taxane or vinca alkaloids such as vinblastine, vincristine, vindesine, and vinorelbine; epipodophyllotoxins such as etoposide and teniposide; fluoropyrimidines such as 5-fluorouracil and fluorodeoxyuridine; antimetabolites such as allopurinol, fludarabine, methotrexate, cladribine, cytarabine, mercaptopurine, gemcitabine, and thioguanine; and camptothecins such as 9-amino camptothecin, irinotecan, topotecan, and the various optical forms of 7-(4-methylpiperazino-methylene)-10,11-ethylenedioxy-20-camptothecin;

(2) cytotoxic chemotherapeutic agents including, but not limited to, alkylating agents such as melphalan, chlorambucil, cyclophosphamide, mechlorethamine, hexamethylmelamine, busulfan, carmustine, lomustine, dacarbazine and nitrosoureas; anti-tumour antibiotics such as doxorubicin, daunomycin, epirubicin, idarubicin, mitomycin-C, dactinomycin, bleomycin and mithramycin; and platinum coordination complexes such as cisplatin, carboplatin, and oxaliplatin; and (3) other chemotherapeutic agents including, but not limited to, anti-estrogens such as tamoxifen, toremifene, raloxifene, droloxifene and iodoxyfene; progestrogens such as megestrol acetate; aromatase inhibitors such as anastrozole, letrazole, vorazole, and exemestane; antiandrogens such as flutamide, nilutamide, bicalutamide, and cyproterone acetate; LHRH agonists and antagagonists such as goserelin acetate and luprolide, testosterone 5.alpha.-dihydroreductase inhibitors such as finasteride; metalloproteinase inhibitors such as marimastat; antiprogestrogens; mitoxantrone, 1-asparaginase, urokinase plasminogen activator receptor function inhibitors; inhibitors or c-kit and bcr/abl tyrosine kinases, (such as Gleevec), immunotherapy, immunoconjugates, cytokines (such as IL-2, IFN alpha and beta), tumor vaccines (including dendritic cell vaccines), thalidomide, COX-2 inhibitors, glucocorticoids (such as prednisone and decadrot), radiation sensitizers, (such as temazolamide), growth factor function inhibitors such as inhibitors of the functions of hepatocyte growth factor; erb-B2, erb-B4, epidermal growth factor receptor (EGFR) and platelet derived growth factor receptors (PDGFR); inhibitors of angiogenesis such as inhibitors of the function of Ephrin receptors (such as, EphB4), vascular endothelial growth factor receptors (VEGFR) and the angiopoietin receptors (Tie1 and Tie2); and other kinase inhibitors such as inhibitors of CDK2 and CDK4.

Anti-neoplastic agents may induce anti-neoplastic effects in a cell-cycle specific manner, i.e., are phase specific and act at a specific phase of the cell cycle, or bind DNA and act in a non cell-cycle specific manner, i.e., are non-cell cycle specific and operate by other mechanisms.

Metabolites of Compounds of Formula I

Also falling within the scope of this invention are the in vivo metabolic products of compounds of Formula I described herein. A "metabolite" is a pharmacologically active product produced through metabolism in the body of a specified compound or salt thereof. Such products may result for example from the oxidation, reduction, hydrolysis, amidation, deamidation, esterification, deesterification, enzymatic cleavage, and the like, of the administered compound. Accordingly, the invention includes metabolites of compounds of Formula I, including compounds produced by a process comprising contacting a compound of this invention with a mammal for a period of time sufficient to yield a metabolic product thereof.

Metabolite products typically are identified by preparing a radiolabelled (e.g., $^{14}C$ or $^{3}H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well-known to those skilled in the art. The metabolite products, so long as they are not otherwise found in vivo, are useful in diagnostic assays for therapeutic dosing of the compounds of the invention.

Articles of Manufacture

In another embodiment of the invention, an article of manufacture, or "kit", containing materials useful for the treatment of the disorders described above is provided. In one embodiment, the kit comprises a container comprising a composition of Formula I. The kit may further comprise a label or package insert on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container holds a compound of Formula I or a formulation thereof which is effective for treating the condition and may have a sterile access port (for example, the container may be an intravenous solution bag or a vial having a stopper pierceable by a hypodermic injection needle). The label or package insert indicates that the composition is used for treating the condition of choice, such as cancer. In one embodiment, the label or package inserts indicates that the composition comprising a compound of Formula I can be used to treat a disorder resulting from abnormal cell growth. In addition, the label or package insert may indicate that the patient to be treated is one having a disorder such as a hyperproliferative disorder, neurodegeneration, cardiac hypertrophy, pain, migraine or a neurotraumatic disease or event. The label or package insert may also indicate that the composition can be used to treat other disorders. Alternatively, or additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the compound of Formula I and, if present, the second pharmaceutical formulation. For example, if the kit comprises a first composition comprising Formula I and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of a compound of Formula I, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, an article of manufacture may comprise (a) a first container with a compound of Formula I contained therein; and optionally (b) a second container with a second pharmaceutical formulation contained therein, wherein the second pharmaceutical formulation comprises a second compound with anti-hyperproliferative activity. Alternatively, or additionally, the article of manufacture may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain other embodiments wherein the kit comprises a composition of Formula I and a second therapeutic agent, the kit may comprise a container for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

Biological Evaluation

B-Raf mutant protein 447-717 (V600E) was co-expressed with the chaperone protein Cdc37, complexed with Hsp90 (Roe, et al. (2004) *Cell* 16:87-98; Stancato, et al. (1993) *J. Biol. Chem.* 268:21711-21716).

Determining the activity of Raf in the sample is possible by a number of direct and indirect detection methods (U.S. Patent Publication No. 2004/082014). Activity of human recombinant B-Raf protein may be assessed in vitro by assay of the incorporation of radiolabelled phosphate to recombinant MAP kinase (MEK), a known physiologic substrate of B-Raf, according to U.S. Patent Publication No. 2004/127496 and WO 03/022840. The activity/inhibition of V600E full-length B-Raf was estimated by measuring the incorporation of radiolabeled phosphate from [γ-$^{33}$P]ATP into FSBA-modified wild-type MEK (Example 8).

Suitable methods of Raf activity depend on the nature of the sample. In cells, the activity of Raf is on the one hand determined by the amount of the Raf expressed in the cell, and on the other hand by the amount of the activated Raf. The activation of the transcription of the genes coding for Raf protein, in particular B-Raf protein, may be made, for example, by determining the amount of the Raf mRNA. Prior art standard methods comprise for instance the DNA chip hybridization, RT-PCR, primer extension and RNA protection. Furthermore, the determination of the Raf activity based on the induction or repression of the transcription of the respective Raf gene(s), may also take place by the coupling of the Raf promoter to suitable reporter gene constructs. Examples for suitable reporter genes are the chloramphenicol transferase gene, the green fluorescent protein (GFP) and variants thereof, the luciferase gene and the Renilla gene. The detection of the increase of expression of Raf proteins may however also be made on the protein level, in this case the amount of protein being detected for instance by antibodies directed against Raf protein. The change of the activity of the Raf protein can however also be put down to increased or reduced phosphorylation or dephosphorylation of the protein. For instance, the B-Raf kinase is regulated by the phosphorylation of the 599Thr and 602Ser remainders (Zhang B. H. and Guan K. L. (2000) *EMBO J.* 19:5429). The change of the phosphorylation of B-Raf proteins may be detected, for example, by antibodies directed against phosphorylated threonine or serine.

Since Raf proteins are threonine/serine kinases, the activity of the Raf proteins can also be determined by their enzymatic activity. The protein MEK is for instance a substrate of B-Raf and the degree of the phosphorylation of MEK permits the determination of the B-Raf activity in the sample. In the same way, the phosphorylation of other substrates, as for instance MBP and peptides which are specifically phosphorylated by Raf (Salh, et al. (1999) *Anticancer Res.* 19:731-740; Bondzi, et al. (2000) *Oncogene* 19:5030-5033), of the Raf proteins can be used for determining the respective activity. Since Raf is part of a signal cascade where a series of kinases are respectively phosphorylated and activated by a superordinated kinase, the activity of Raf can also be determined by evaluating the phosphorylation degree of each kinase subordinated to Raf. This so-called map kinase pathway leads, among other features, also to a specific activation of transcription factors and thus to a transcriptional activation of genes, such that the activity of Raf can indirectly be determined by measuring the activity of these target genes.

Exemplary compounds from Table 1 were prepared, characterized, and assayed for their B-Raf binding activity and in vitro activity against tumor cells. The range of B-Raf binding activities was less than 1 nM to about 10 μM. Certain exemplary compounds of the invention had B-Raf binding activity $IC_{50}$ values less than 10 nM. Certain compounds of the invention had cell-based activity, i.e. cells expressing activated mutants of the B-Raf target kinase, $IC_{50}$ values less than 100 nM.

EXAMPLES

In order to illustrate the invention, the following examples are included. However, it is to be understood that these examples do not limit the invention and are only meant to suggest a method of practicing the invention. Persons skilled in the art will recognize that the chemical reactions described may be readily adapted to prepare a number of other Raf inhibitors of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention Example 1

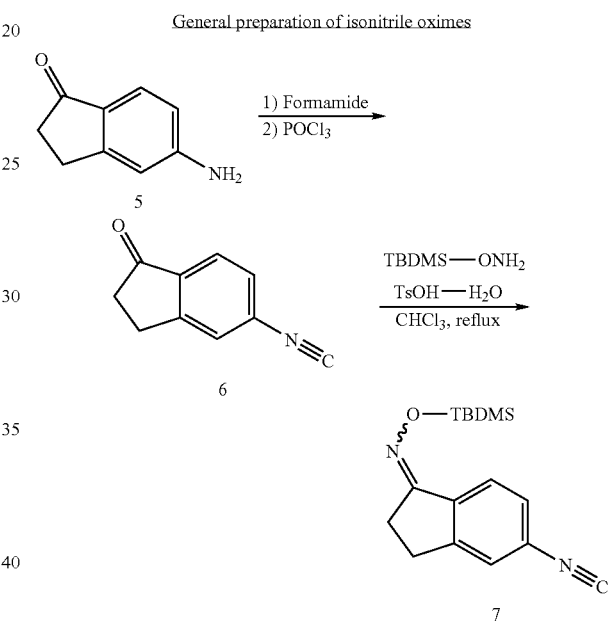

Step A: A mixture of 5-amino-2,3-dihydroinden-1-one (5) and butyl formate (5 eq.) was allowed to reflux overnight. The reaction mixture was then concentrated to an oil which solidified upon standing. The crude material [N-(1-oxo-2,3-dihydro-1H-inden-5-yl)formamide (15.00 g, 73 mmol)] was suspended in cold (0° C.) THF (300 mL) and triethylamine (81 mL, 582 mmol). To this was slowly added 6.6 mL (1 eq.) of POCl$_3$. HPLC after 2 hours showed almost complete conversion. The crude reaction mixture was added to silica gel and concentrated (the bath temp was kept at about 25° C.), and the concentrated mixture was loaded onto a silica column. The product was eluted with DCM (100%) to give 5-isocyano-2,3-dihydroinden-1-one (6).

Step B: 5-isocyano-2,3-dihydroinden-1-one (6) (3.00 g, 19.1 mmol) was combined with 1.4 eq. of O-(tert-butyldimethylsilyl)hydroxylamine (3.94 g, 26.7 mmol) and TsOH-H$_2$O (0.363 g, 1.91 mmol) in 100 mL CHCl$_3$ and heated to reflux overnight. TLC showed a small amount of remaining starting material and two non-polar spots corresponding to the oxime isomers. The reaction mixture was filtered and concentrated to a brown semi-solid, then purified immediately by loading onto a silica column with DCM and eluting with 1% MeOH/DCM to give 4.1 g (75%) of 5-isocyano-2,3-dihydroinden-1-one O-tert-butyldimethylsilyl oxime (7).

Example 2

Preparation of 5-(2-(4-(hydroxymethyl)phenyl)imidazo[1,2-a]pyrazin-3-ylamino)-2,3-dihydro-1H-inden-1-one oxime (13)

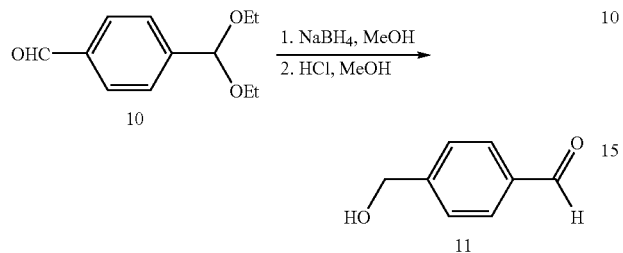

Step A: To a cold (0° C.) solution of 4-(diethyoxymethyl)benzaldehyde (5.2 g, 24 mmol) in MeOH (50 mL) was added NaBH$_4$ (0.93 g, 24 mmol), and the reaction mixture was stirred for 3 hours. The MeOH was removed and the residue was taken up in DCM and diluted with water. The aqueous layer was extracted with DCM (3×50 mL). The combine organic layers were dried, filtered and concentrated. The crude oil was dissolved in MeOH (50 mL) and cooled to 0° C. To this was added 2N HCl (10.0 mL) in ether. The reaction mixture was left at room temperature for 24 hours. The MeOH was removed and the crude product was purified by flash column chromatography, eluting with EtOAc/Hexane (3:7) to yield 2.92 g of 4-(hydroxymethyl)benzaldehyde (11) as a colorless oil.

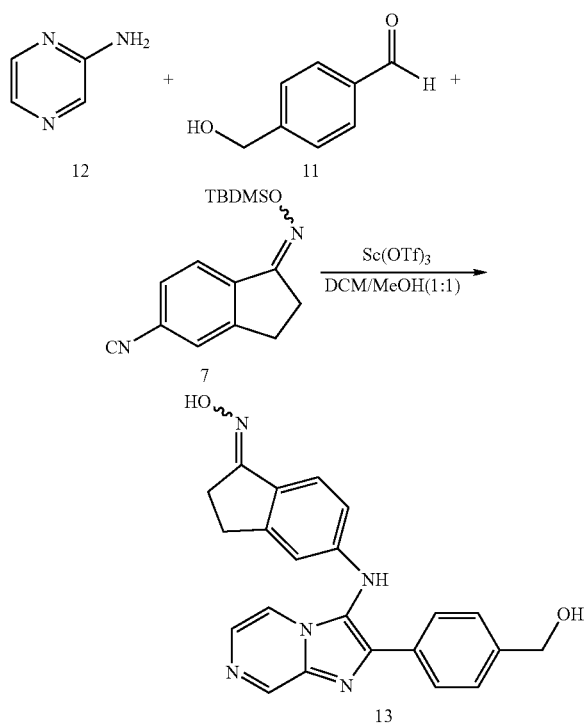

Step B: Pyrazin-2-amine (12) (0.10 g, 1.1 mmol) was combined with 0.21 g (1.3 mmol) of 4-(hydroxymethyl)benzaldehyde (11) and Sc(OTf)$_3$ (0.053 g, 0.11 mmol) and the combination was dissolved in DCM/MeOH (1:1) and stirred for 1 hours. To this was added 0.310 g (1.1 mmol) of 5-isocyano-2,3-dihydroinden-1-one O-tert-butyldimethylsilyl oxime (7) and the reaction mixture was left at room temperature overnight. The reaction mixture was concentrated and purified by flash column chromatography, eluting with DCM, DCM/MeOH (50:1) and DCM/MeOH (25:1) to provide 0.175 g of the desired product (13). MS (APCI) m/z 386.0 (M+1).

Example 3

Preparation of 2-(4-(3-(1-(hydroxyimino)-2,3-dihydro-1H-inden-5-ylamino)imidazo[1,2-a]pyrazin-2-yl)phenoxy)-N-methylacetamide (14)

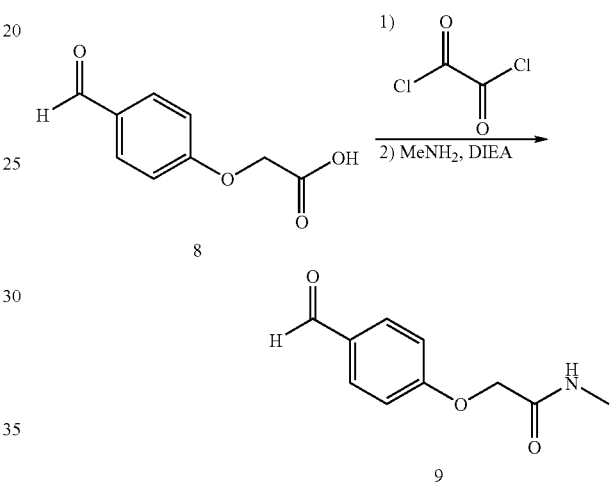

Step A: 2-(4-formylphenoxy)acetic acid was suspended in 20 mL of DCM at 0° C., and 0.5 mL of DMF was added followed by the dropwise addition of oxalyl chloride. The solution was allowed to warm to room temperature with stirring until gas evolution stopped and the solution was homogeneous. The solution containing the crude acid chloride was concentrated under vacuum and the residue resuspended in DCM, cooled to 0° C., and methylamine and DIEA were added. The mixture was allowed to warm to room temperature with stirring over 12 hours. The reaction mixture was then poured into 5% HCl, washed 3 times with EtOAc, dried over sodium sulfate, filtered and concentrated to a thick brown oil which was purified by column using DMC/MeOH to afford 2-(4-formylphenoxy)-N-methylacetamide (9) as an off white solid. NMR (CDCl3, 400 mHz), d=9.9 (1H, s), 7.88 (2H, d, J=8.6 Hz), 7.04 (2H, d, J=8.6 Hz), 6.6-6.5 (1H, BS, 4.54 (2H, s), 2.93 (3H, d, J=4.7 Hz).

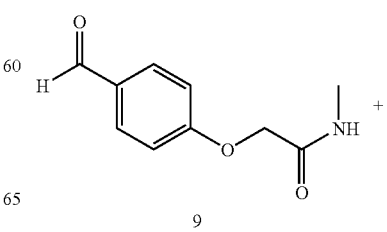

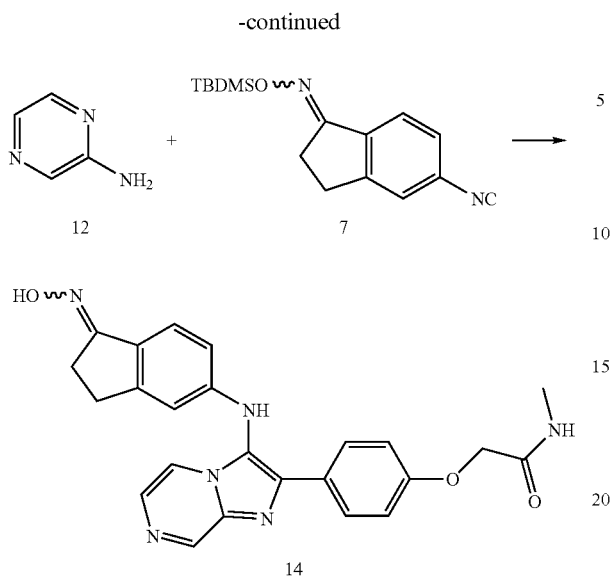

Step B: A mixture of pyrazin-2-amine (12) (1.1 eq.), 2-(4-formylphenoxy)-N-methylacetamide (9) (1.1 eq.) and a catalytic amount of Sc(OTf)$_3$ was stirred in 2 mL of 1:1 DCM/MeOH at room temperature for 30 minutes. To this was added 5-isocyano-2,3-dihydroinden-1-one O-tert-butyldimethylsilyl oxime (1 eq.) as a 2 mL solution in 1:1 DCM/MeOH and the mixture was stirred at room temperature for 18 hours. The reaction mixture was then concentrated under vacuum and the residue taken up in EtOAc (with a small amount of methanol added to help with dissolution) and purified by column using 1-5% MeOH/EtOAc+1% NH$_4$OH. The desired product (14) was isolated as a light yellow solid. MS (APCI) m/z 443.1 (M+1).

Example 4

Preparation of 5-(2-(1-methyl-1H-indol-3-yl)imidazo[1,2-a]pyrazin-3-ylamino)-2,3-dihydro-1H-inden-1-one oxime (17)

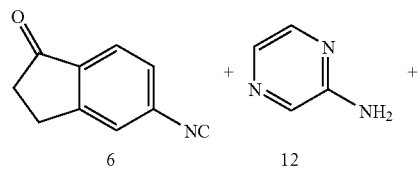

Step A: 5-Isocyano-2,3-dihydroinden-1-one (6) (60.0 mg, 379 μmol) was combined with pyrazin-2-amine (12) (36.1 mg, 379 μmol), 1-methyl-1H-indole-3-carbaldehyde (15) (60.4 mg, 379 μmol) and Sc(OTf)$_3$ (18.7 mg, 37.9 μmol) in DCM/MeOH and stirred at room temperature overnight. The solvent was evaporated and purified by silica using 2% MeOH/EtOAc to provide 5-(2-(1-methyl-1H-indol-3-yl)imidazo[1,2-a]pyrazin-3-ylamino)-2,3-dihydroinden-1-one (16). MS (APCI) m/z (M+1)

Step B: The ketone (16) was suspended in 20 mL 1:1 EtOH/H$_2$O and heated to reflux with an excess of aqueous H$_2$NOH (2 mL). TLC showed the reaction was complete after 6 hours, which was confirmed by LCMS. The reaction mixture was concentrated under reduced pressure, and the residue was transferred to a separatory funnel and extracted between EtOAc and water. The organic layer was dried, filtered and concentrated the to a yellow solid. Purification was carried out using silica gel chromatography using 2% MeOH/EtOAc. The desired product (17) was isolated (13% yield).

Example 5

Preparation of 5-(2-(4-aminophenyl)imidazo[1,2-a]pyrazin-3-ylamino)-2,3-dihydro-1H-inden-1-one oxime (20)

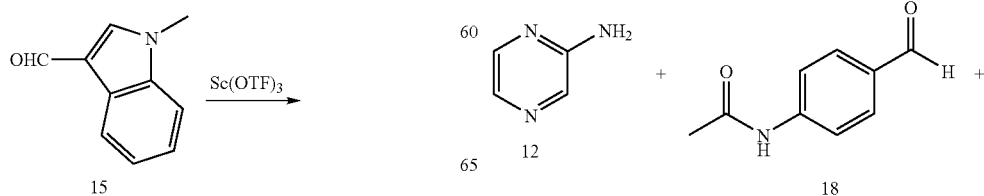

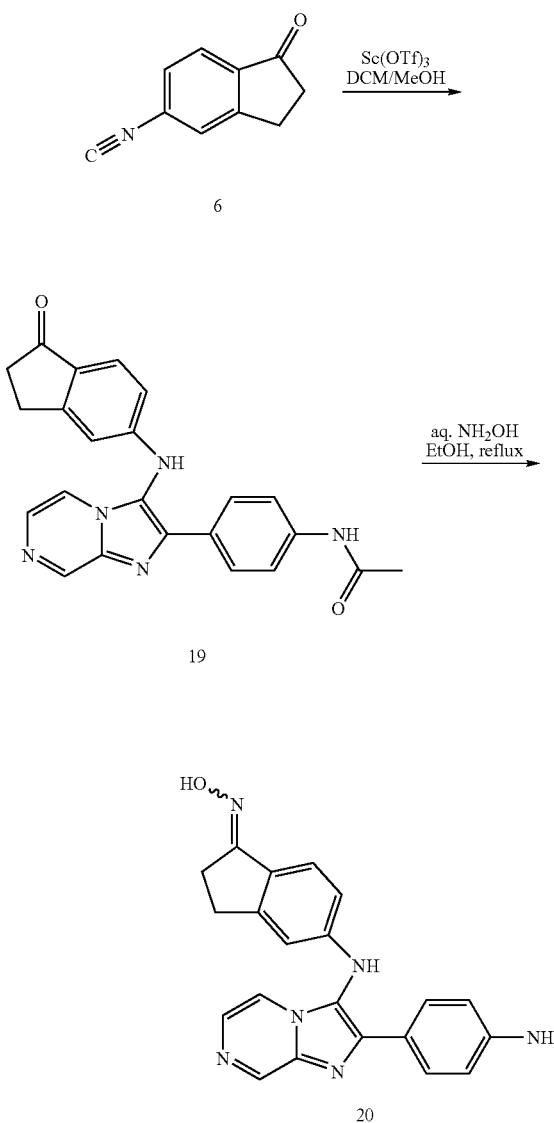

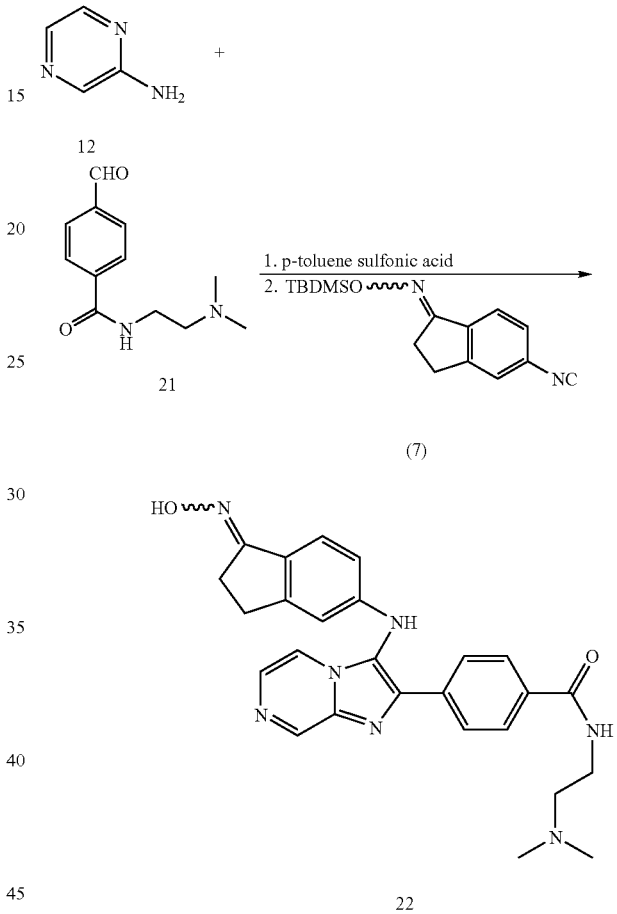

Step A: Pyrazin-2-amine (12) (0.060 g, 0.63 mmol), 2-(4-formylphenoxy)-N-methylacetamide (18) (0.12 g, 0.76 mmol) and Sc(OTf)$_3$ (0.031 g, 0.063 mmol) were dissolved in DCM/MeOH (1:1) and stirred for 1 hour. To this was added 5-isocyano-2,3-dihydroinden-1-one (6) (0.100 g, 0.63 mmol), and the reaction mixture was left at room temperature overnight. The reaction mixture was concentrated and purified by flash column chromatography, eluting with DCM, DCM/MeOH (50:1), DCM/MeOH (25:1) to yield 0.111 g of N-(4-(3-(1-oxo-2,3-dihydro-1H-inden-5-ylamino)imidazo[1,2-a]pyrazin-2-yl)phenyl) acetamide (19) as an orange solid. MS (APCI) m/z 398.2 (M+1).

Step B: A mixture of the acetamide (19) (0.108 g, 0.26 mmol) and hydroxyl amine (50% wt, 2.0 mL) was refluxed in EtOH (5 mL) for 48 hours. The resulting yellow precipitate was collected by filtration and washed with MeOH and DCM to yield 0.040 g of the desired product (20). MS (APCI) m/z 371.2 (M+1).

Example 6

Preparation of N-(2-(dimethylamino)ethyl)-4-(3-(1-(hydroxyimino)-2,3-dihydro-1H-inden-5-ylamino)imidazo[1,2-a]pyrazin-2-yl)benzamide (22)

A mixture of pyrazin-2-amine (12) (0.05 g, 0.52 mmol, 1.0 equiv.), N-(2-(dimethylamino)ethyl)-4-formylbenzamide (21) (0.12 g, 0.52 mmol, 1.0 equiv.) and toluene sulfonic acid (0.12 g, 0.65 mmol, 1.25 equiv.) was stirred in 2 mL 1:1 MeOH/DCM at room temperature for 45 minutes. To this was added 5-isocyano-2,3-dihydroinden-1-one O-tert-butyldimethylsilyl oxime (7) (0.150 g, 0.52 mmol, 1.0 equiv.) in 1 mL 1:1 DCM/MeOH followed by the addition of a catalytic amount of Sc(OTf)$_3$. Reaction stirred at room temperature for 3 hours. TLC showed product (10% MeOH/EtOAc, 1% NH$_4$OH), which was confirmed by MS and LC/MS. Water (0.5 mL) was added followed by solid sodium bicarbonate. The solution was stirred for 30 minutes, and then solid sodium sulfate was added. The reaction mixture was filtered after 1 hour and concentrated to a yellow solid. The residue was taken up in ethyl acetate, washed with water, dried, and

Example 7

Preparation of methyl 2-(4-(3-(1-(hydroxyimino)-2,3-dihydro-1H-inden-5-ylamino)imidazo[1,2-a]pyrazin-2-yl)phenoxy)acetate (24)

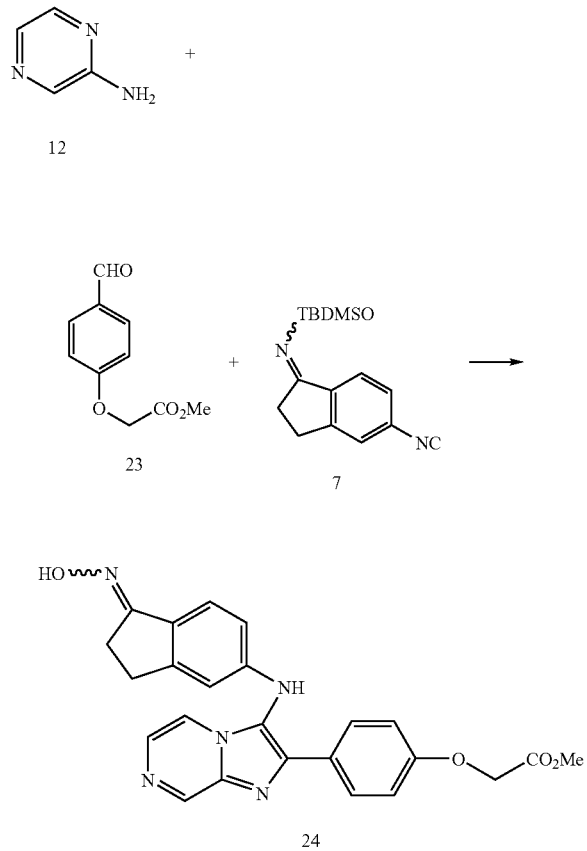

In a 1 mL solution of 1:1 DCM/MeOH was added pyrazin-2-amine (12) (0.0498 g, 0.524 mmol), methyl 2-(4-formylphenoxy)acetate (23) (0.102 g, 0.524 mmol) (prepared from the acid and trimethylsilyl diazomethane) and catalytic Sc(OTf)$_3$. The mixture was stirred for 1 hour before adding (E)-5-isocyano-2,3-dihydroinden-1-one O-tert-butyldimethylsilyl oxime (7) (0.150 g, 0.524 mmol) in 1 mL DCM/MeOH and then stirred for an additional 12 hours. TFA (2 drops) was added to the reaction and stirred for 1 hour. The TFA was quenched by adding saturated sodium bicarbonate, followed by the addition of sodium sulfate and a small amount of silica gel. The mixture was concentrated to dryness and loaded onto a prewetted column (1% MeOH/DCM), eluting with 1-4% MeOH/DCM+1% NH4OH. The compound (24) was isolated as a light yellow solid. MS (APCI) m/z 444.2 (M+1).

purified by column chromatography using DCM-MeOH. The desired product (22) was isolated as a yellow solid. MS (APCI) m/z 470.1 (M+1).

Example 8

Preparation of 5-(2-(3-(ethylamino)phenyl)imidazo[1,2-a]pyrazin-3-ylamino)-2,3-dihydro-1H-inden-1-one oxime (31)

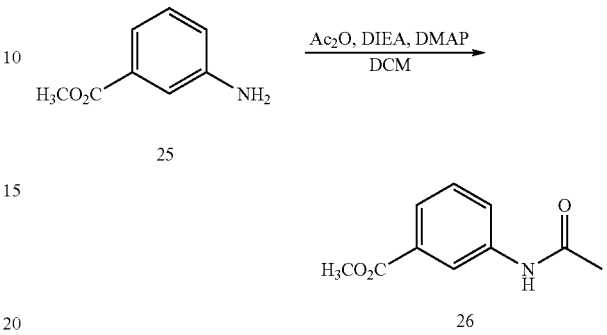

Step A: Methyl 3-aminobenzoate (25) (5.0 g) was combined in DCM (120 mL) with DIEA (7.5 mL) and Ac$_2$O (3.7 mL). DMAP was added to the solution and the reaction mixture was stirred overnight at room temperature. Water was added to the reaction mixture and the layers were separated. The organic layer was diluted with CHCl$_3$ and washed sequentially with 1N NaOH, 1N HCl, water, and brine, and then dried over Na$_2$SO$_4$, filtered and concentrated to provide compound (26) as a pink solid (5.5 g, 86% yield).

Step B: A solution of methyl 3-acetamidobenzoate (26) (1.5 g) in THF was treated with LAH (30 mL of a 1M solution in THF) and heated to 50° C. overnight. The solution was cooled in an ice bath and quenched carefully in succession with water (1.1 mL), 15% NaOH (1.1 mL), and water (3.3 mL). The precipitate was filtered and rinsed with DCM. The crude mixture was purified by silica gel chromatography (50% ethyl acetate/hexanes) to provide the product (27) as a brown oil (941 mg, 80%).

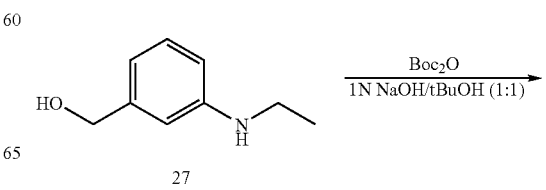

-continued

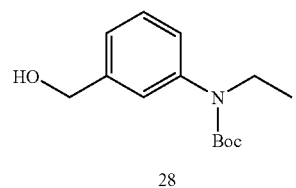

28

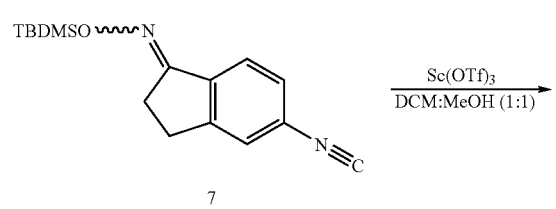

7

Step C: To a solution of (3-(ethylamino)phenyl)methanol (27) (838 mg) in t-BuOH (6 mL) and Boc$_2$O (1.33 g, 1.1 equiv.) was added 1N NaOH (1.1 equiv., 6.09 mL). The reaction was stirred overnight at room temperature. The white precipitate was filtered off and the cake was washed with EtOAc. Water was added to the filtrate and the organic layer was collected, dried (MgSO$_4$), filtered, and concentrated. The product (27) was obtained as a light orange oil (825 mg, 59%) after silica gel chromatography.

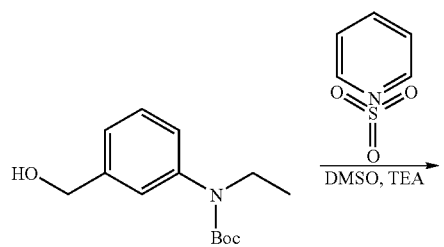

28

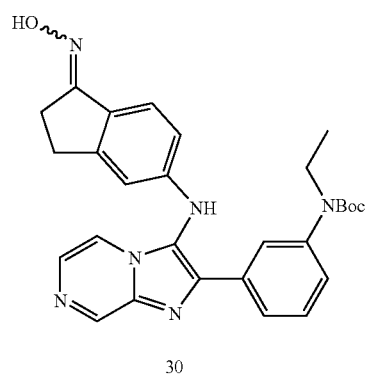

30

Step E: A mixture of aminopyrazine (12) (38 mg) and tert-butyl ethyl(3-formylphenyl)carbamate (29) (105 mg) in 1:1 DCM:MeOH (4 mL) with a catalytic amount of Sc(OTf)$_3$ (17 mg) was shaken at room temperature for 1 hour. Neat 5-isocyano-2,3-dihydroinden-1-one O-tert-butyldimethylsilyl oxime (7) (113 mg) was added to the reaction mixture, and the mixture was stirred overnight at room temperature. Volatiles were removed by rotary evaporation, and the residue was taken up in DCM and purified by Sep-Pak column (100% ethyl acetate) to provide the crude product (30), which was taken on directly in the next step.

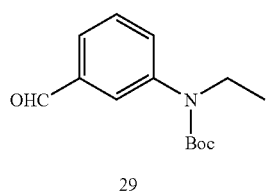

29

Step D: To a solution of tert-butyl ethyl(3-(hydroxymethyl)phenyl)carbamate (28) (793 mg) and TEA (2.0 mL) in a 1:1 v/v mixture of DMSO and DCM (14 mL) at 0° C. was added sulfur trioxide-pyridine (1.8 g) at once. The reaction was allowed to stir at 0° C. for 1 hour, and then diluted with ether and was washed sequentially with water, saturated citric acid, water, and brine. The combined aqueous layers were extracted once with EtOAc and added to the collected organics, which were dried over anhydrous MgSO$_4$. The product was obtained by column chromatography (20% ethyl acetate/hexanes) as a yellow oil (691 mg, 88%). $^1$H NMR (400 MHz, CDCl$_3$): 10.0 (s, 1 H), 7.73 (m, 2 H), 7.52 (m, 2 H), 3.76 (q, 2H), 1.42 (s, 9 H), 1.19 (t, 3H).

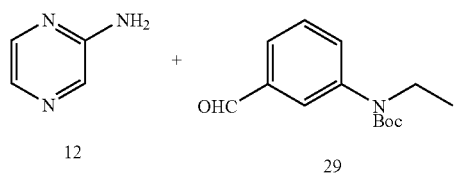

12     29

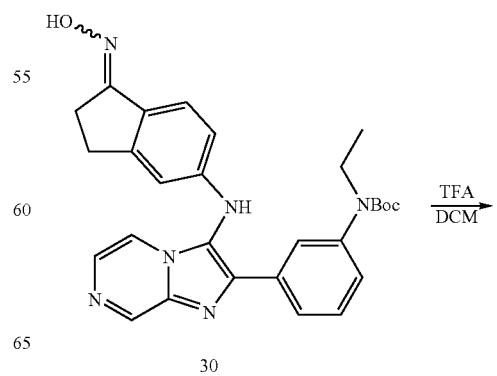

30

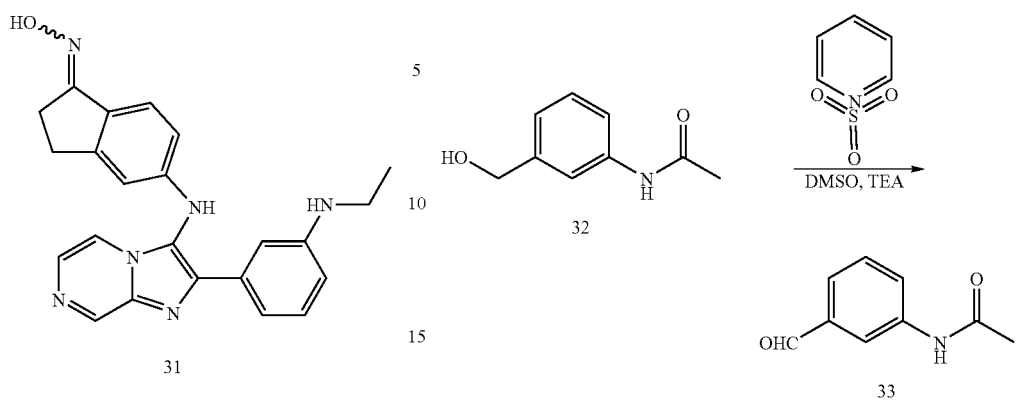

Step F: Tert-Butyl ethyl(3-(3-(1-(hydroxyimino)-2,3-dihydro-1H-inden-5-ylamino)imidazo[1,2-a]pyrazin-2-yl)phenyl)carbamate (30) (81 mg) was dissolved in DCM (2 mL) in an ice bath. To this was added TFA (2 mL) and the mixture was stirred for 30 minutes at 0° C. Volatiles were removed by rotary evaporation, and the residue was diluted with DCM and made basic with TEA. Volatiles were removed by rotary evaporation, and the residue was purified by column chromatography to afford the product (31) as a yellow solid (61 mg, 94%). MS (pos-APCI) shows M+1=399.2.

Example 9

Preparation of N-(3-(3-(1-(hydroxyimino)-2,3-dihydro-1H-inden-5-ylamino)imidazo[1,2-a]pyrazin-2-yl)phenyl)acetamide (34)

Step A: Methyl 3-acetamidobenzoate (26) (2.0 g) was taken up in THF (30 mL). A solution of LiBH4 (50 mL of a 2.0 M solution in THF) was added and the reaction was heated to 50° C. overnight, then cooled in an ice bath and carefully quenched with 1N HCl. The crude reaction mixture was then diluted with water and EtOAc. The layers were separated and the organic layer was purified by column chromatography (100% EtOAc) to afford the product (32) as a white solid (872 mg, 51%).

Step B: To a solution of N-(3-(hydroxymethyl)phenyl)acetamide (32) (872 mg) and TEA (3.3 mL) in a 1:1 v/v mixture of DMSO and DCM (12 mL) at 0° C. was added sulfur trioxide-pyridine (2.9 g) at once. The reaction was stirred at 0° C. for 1 hour, and then diluted with ether and washed sequentially with water, saturated citric acid, water, and brine. The combined aqueous layers were extracted 4× with EtOAc and added to the collected organic layers, which were dried over anhydrous MgSO4. The product (33) was obtained by silica gel chromatography (75% EtOAc/hexanes) as a colorless glass (761 mg, 88%). ¹HNMR (400 MHz, CDCl3): 10.0 (s, 1 H), 8.0 (s, 1 H), 7.87 (m, 1 H), 7.61 (m, 1 H), 7.49 (m, 1 H), 2.22 (s, 3 H).

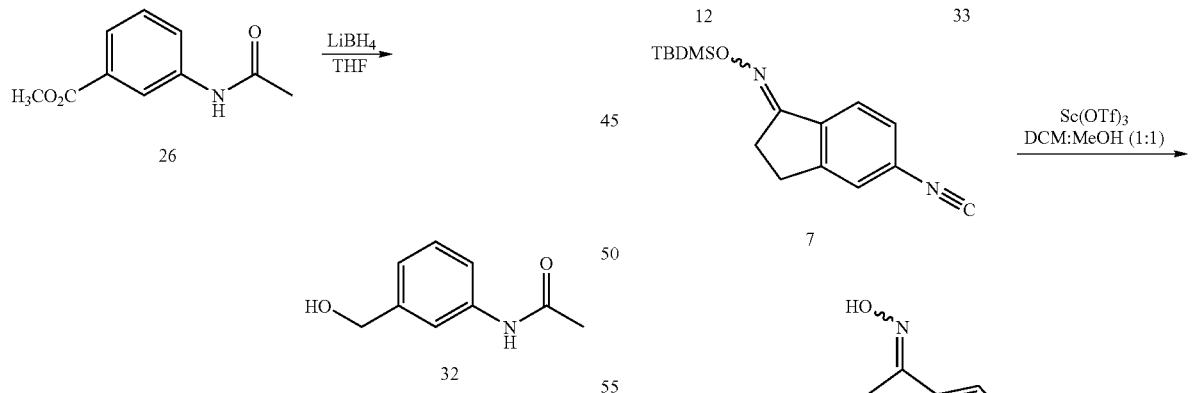

Step C: Aminopyrazine (12) (54 mg) and N-(3-formylphenyl)acetamide (33) (109 mg) were combined in 1:1 DCM:MeOH (4 mL) with a catalytic amount of Sc(OTf)$_3$ (36 mg). The reaction mixture was shaken at room temperature for 1 hour, followed by addition of neat 5-isocyano-2,3-dihydroinden-1-one O-tert-butyldimethylsilyl oxime (7) (160 mg) and then stirred overnight at room temperature. Volatiles were removed by rotary evaporation, and the residue was diluted with DCM and purified by silica gel chromatography (5% MeOH/EtOAc) to afford the product (34).

Example 10

Preparation of 5-(2-(3-aminophenyl)imidazo[1,2-a]pyrazin-3-ylamino)-2,3-dihydro-1H-inden-1-one oxime (35)

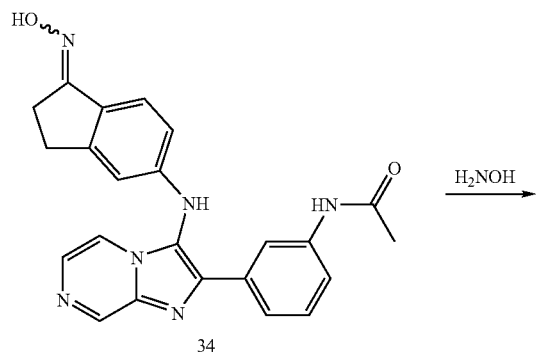

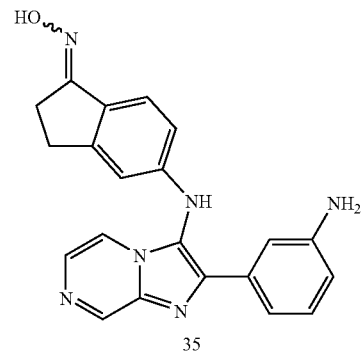

N-(3-(3-(1-(Hydroxyimino)-2,3-dihydro-1H-inden-5-ylamino)imidazo[1,2-a]pyrazin-2-yl)phenyl)acetamide (34) (83 mg) was dissolved in EtOH (10 mL) and treated with a 50% wt. H$_2$NOH solution in water (5 mL). The solution was refluxed overnight at 100° C. Volatiles were removed by rotary evaporation, and the residue was purified by silica gel chromatography to provide the product (35). MS (pos-APCI) shows M+1=371.2.

The following compounds shown in Table 1 were prepared using the methods previously described. The oxime geometry shown is implied; however, the oxime moiety of the compounds 36-119 can exist as either the E or Z isomer, or as a mixture of both.

TABLE 1

| Compound # | Structure | Mol. Weight | Formula | MS APCI, m/z, m + 1 |
|---|---|---|---|---|
| 36 | 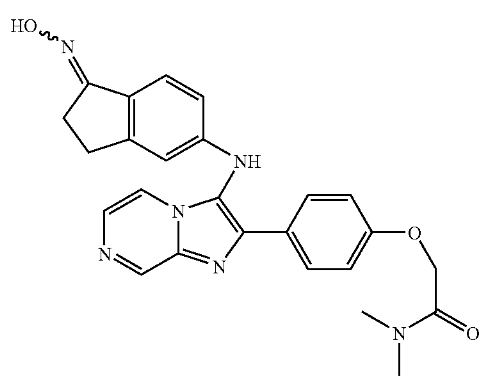 | 456.496 | $C_{25}H_{24}N_6O_3$ | 457.3 |

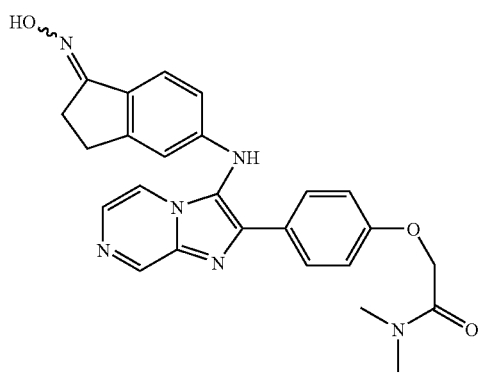

TABLE 1-continued
| Compound # | Structure | Mol. Weight | Formula | MS APCI, m/z, m + 1 |
|---|---|---|---|---|
| 37 | 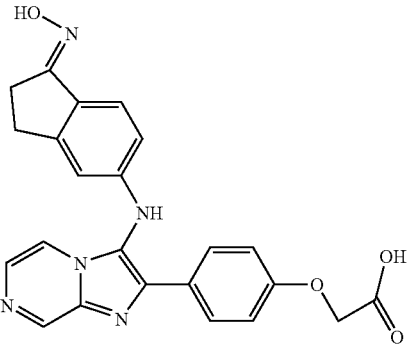 | 429.428 | $C_{23}H_{19}N_5O_4$ | 430.2 |
| 38 | 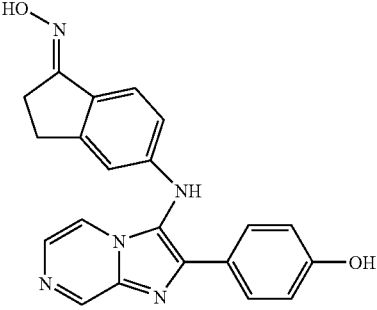 | 371.392 | $C_{21}H_{17}N_5O_2$ | 372.2 |
| 39 | 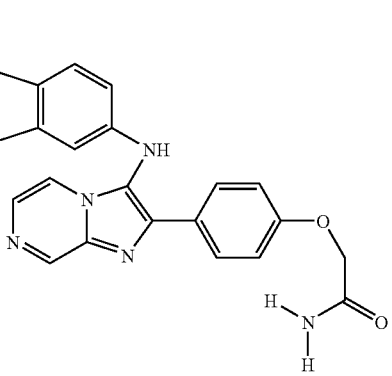 | 428.443 | $C_{23}H_{20}N_6O_3$ | 457.3 |
| 40 | 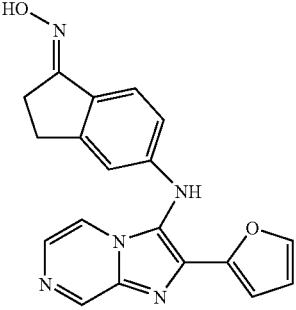 | 345.355 | $C_{19}H_{15}N_5O_2$ | 346.1 |

TABLE 1-continued

| Compound # | Structure | Mol. Weight | Formula | MS APCI, m/z, m + 1 |
|---|---|---|---|---|
| 41 | 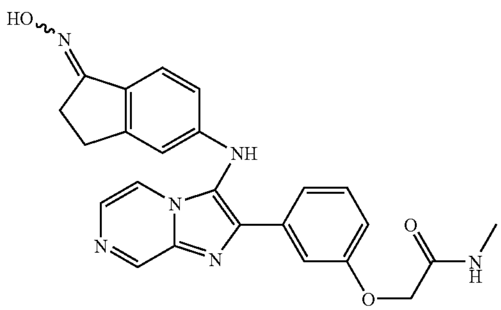 | 442.47 | $C_{24}H_{22}N_6O_3$ | 443.1 |
| 42 | 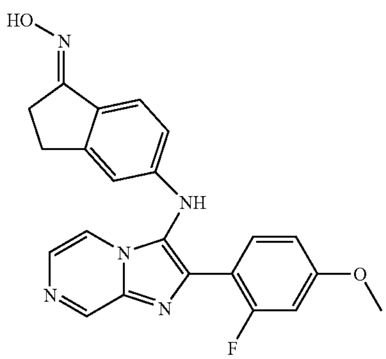 | 403.409 | $C_{22}H_{18}FN_5O_2$ | 404.3 |
| 43 | 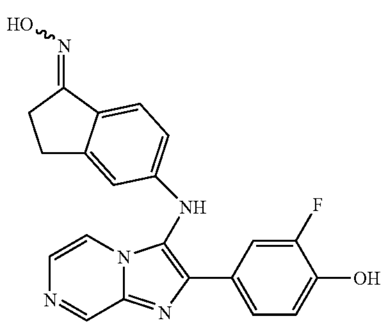 | 389.382 | $C_{21}H_{16}FN_5O_2$ | 390.1 |
| 44 | 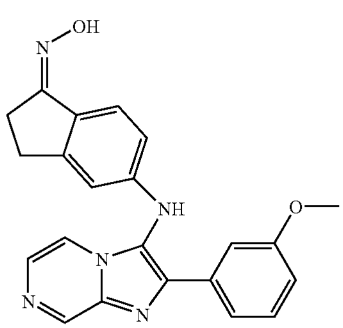 | 385.419 | $C_{22}H_{19}N_5O_2$ | 386 |

TABLE 1-continued

| Compound # | Structure | Mol. Weight | Formula | MS APCI, m/z, m + 1 |
|---|---|---|---|---|
| 45 | 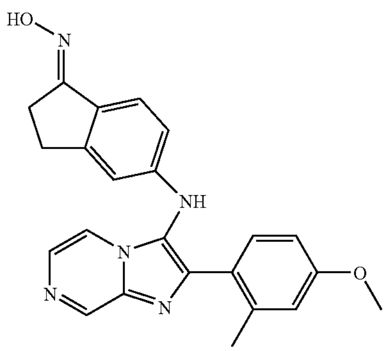 | 399.445 | $C_{23}H_{21}N_5O_2$ | 400.2 |
| 46 | 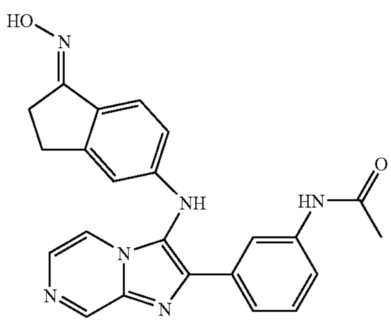 | 412.444 | $C_{23}H_{20}N_6O_2$ | 413.1 |
| 47 | 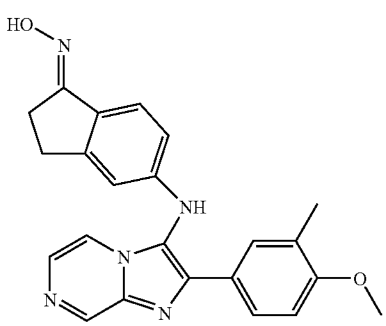 | 399.445 | $C_{23}H_{21}N_5O_2$ | 400.2 |
| 48 | 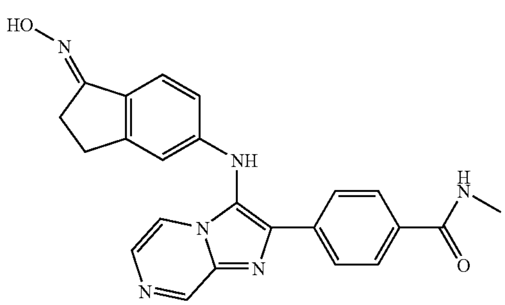 | 412.444 | $C_{23}H_{20}N_6O_2$ | 413.1 |

TABLE 1-continued
| Compound # | Structure | Mol. Weight | Formula | MS APCI, m/z, m + 1 |
|---|---|---|---|---|
| 49 | 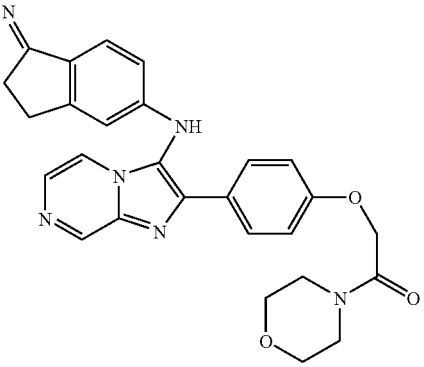 | 498.533 | $C_{27}H_{26}N_6O_4$ | 499.2 |
| 50 | 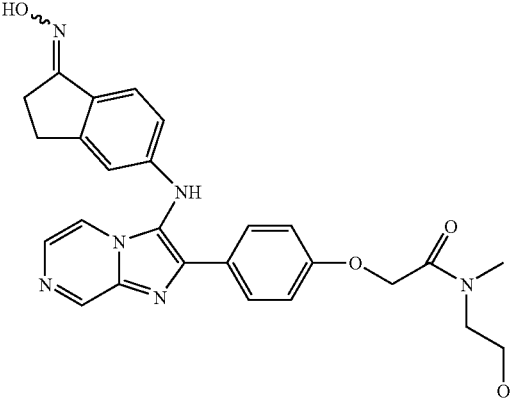 | 500.549 | $C_{27}H_{28}N_6O_4$ | 501.2 |
| 51 | 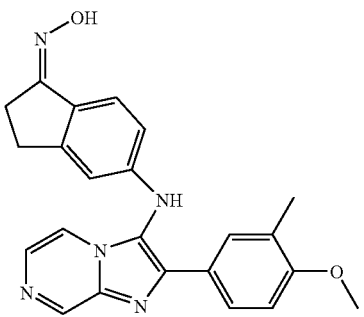 | 399.445 | $C_{23}H_{21}N_5O_2$ | 400.1 |
| 52 | 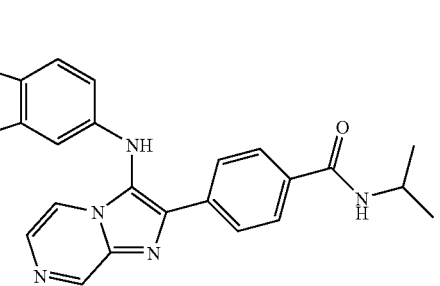 | 440.497 | $C_{25}H_{24}N_6O_2$ | 441 |

TABLE 1-continued

| Compound # | Structure | Mol. Weight | Formula | MS APCI, m/z, m + 1 |
|---|---|---|---|---|
| 53 | 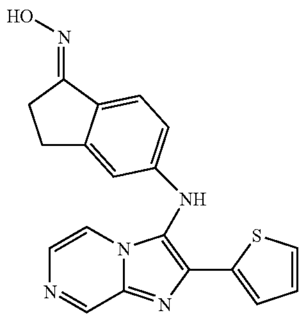 | 361.42 | $C_{19}H_{15}N_5OS$ | 362.1 |
| 54 | 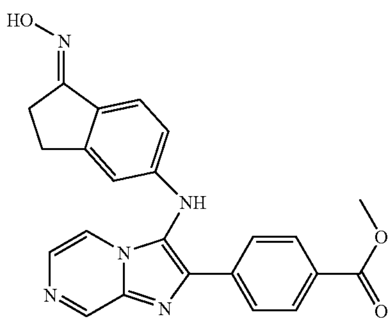 | 413.429 | $C_{23}H_{19}N_5O_3$ | 414.1 |
| 55 | 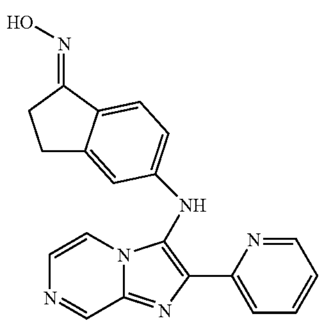 | 356.381 | $C_{20}H_{16}N_6O$ | 357.3 |
| 56 | 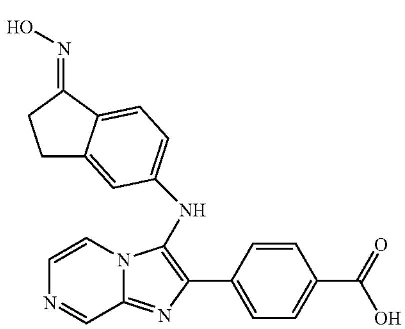 | 399.402 | $C_{22}H_{17}N_5O_3$ | 400 |

TABLE 1-continued

| Compound # | Structure | Mol. Weight | Formula | MS APCI, m/z, m + 1 |
|---|---|---|---|---|
| 57 | 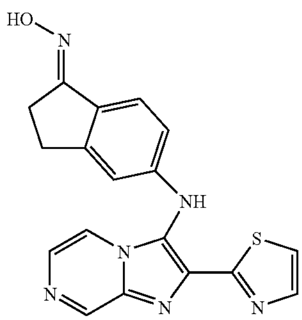 | 362.408 | C₁₈H₁₄N₆OS | 363.1 |
| 58 | 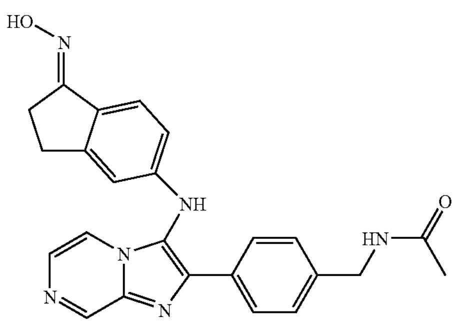 | 426.47 | C₂₄H₂₂N₆O₂ | 427.1 |
| 59 | 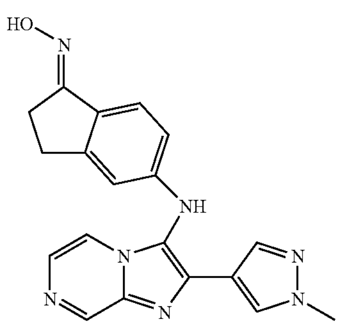 | 359.385 | C₁₉H₁₇N₇O | 360.1 |
| 60 | 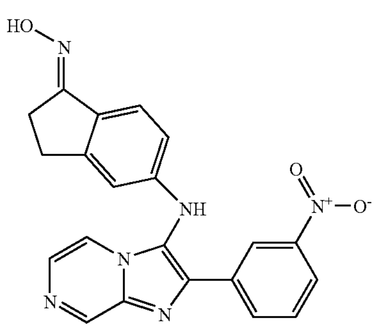 | 400.39 | C₂₁H₁₆N₆O₃ | 401.1 |

TABLE 1-continued

| Compound # | Structure | Mol. Weight | Formula | MS APCI, m/z, m + 1 |
|---|---|---|---|---|
| 61 | 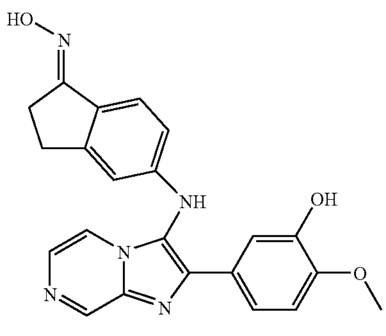 | 401.418 | $C_{22}H_{19}N_5O_3$ | 402 |
| 62 | 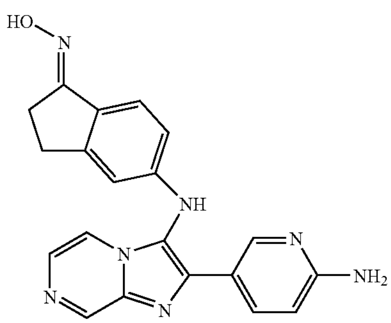 | 371.395 | $C_{20}H_{17}N_7O$ | 372.2 |
| 63 | 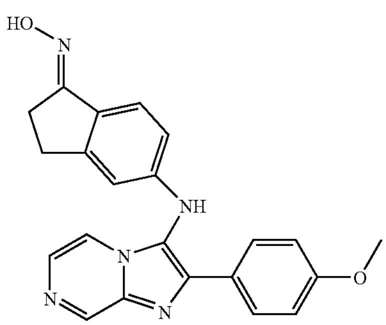 | 385.419 | $C_{22}H_{19}N_5O_2$ | 386.2 |
| 64 | 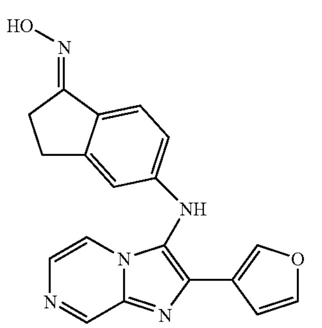 | 345.355 | $C_{19}H_{15}N_5O_2$ | 346.1 |

TABLE 1-continued

| Compound # | Structure | Mol. Weight | Formula | MS APCI, m/z, m + 1 |
|---|---|---|---|---|
| 65 | 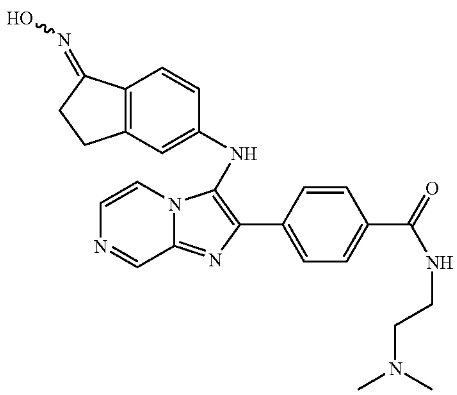 | 469.538 | $C_{26}H_{27}N_7O_2$ | 470.1 |
| 66 | 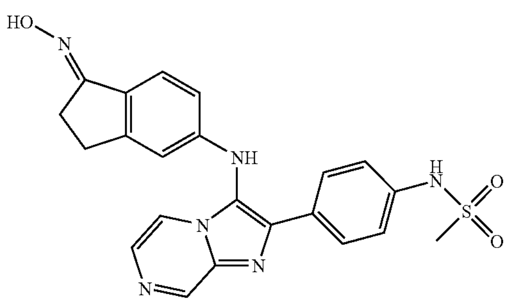 | 448.498 | $C_{22}H_{20}N_6O_3S$ | 447(M−1) |
| 67 | 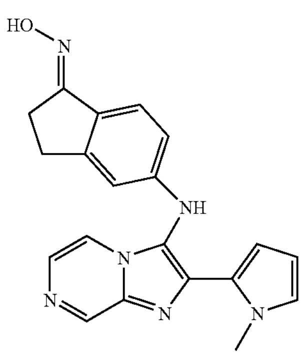 | 358.397 | $C_{20}H_{18}N_6O$ | 359.2 |
| 68 | 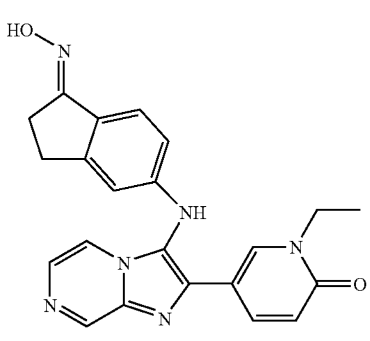 | 400.433 | $C_{22}H_{20}N_6O_2$ | 401.1 |

TABLE 1-continued
| Compound # | Structure | Mol. Weight | Formula | MS APCI, m/z, m + 1 |
|---|---|---|---|---|
| 69 | 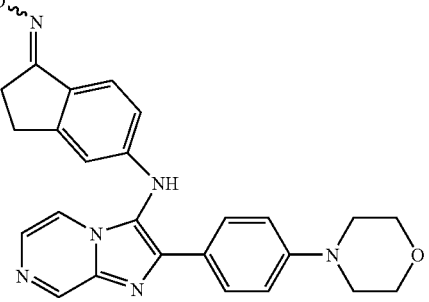 | 440.497 | $C_{25}H_{24}N_6O_2$ | 441.2 |
| 70 | 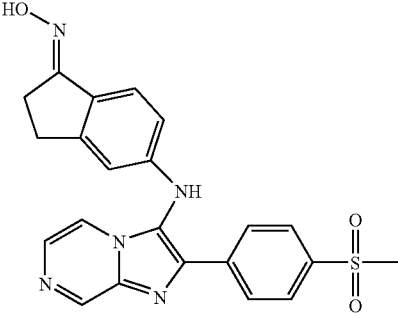 | 433.483 | $C_{22}H_{19}N_5O_3S$ | 434.1 |
| 71 | 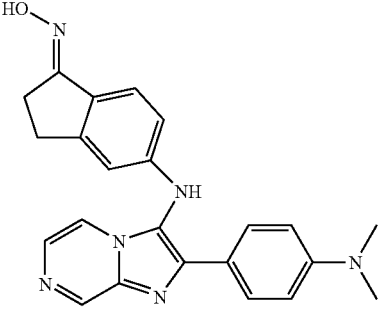 | 398.46 | $C_{23}H_{22}N_6O$ | 399.2 |
| 72 | 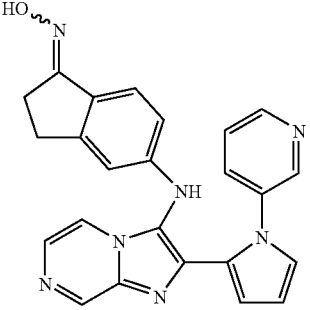 | 421.454 | $C_{24}H_{19}N_7O$ | 422.2 |

TABLE 1-continued
| Compound # | Structure | Mol. Weight | Formula | MS APCI, m/z, m + 1 |
|---|---|---|---|---|
| 73 | 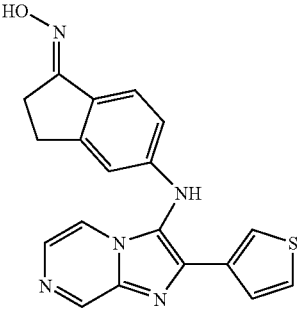 | 361.42 | C₁₉H₁₅N₅OS | 362.1 |
| 74 | 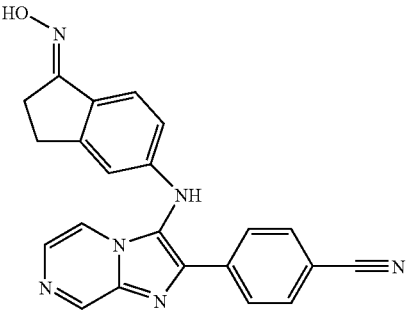 | 380.402 | C₂₂H₁₆N₆O | 381.1 |
| 75 | 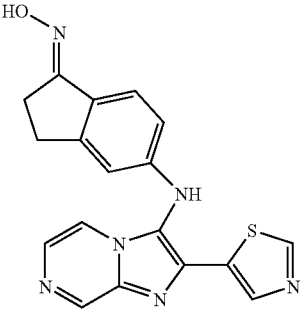 | 362.408 | C₁₈H₁₄N₆OS | 363.1 |
| 76 | 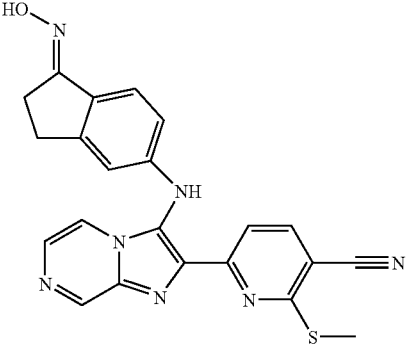 | 427.482 | C₂₂H₁₇N₇OS | 428 |

TABLE 1-continued

| Compound # | Structure | Mol. Weight | Formula | MS APCI, m/z, m + 1 |
|---|---|---|---|---|
| 77 | 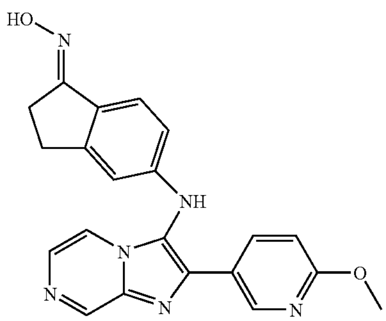 | 386.407 | C₂₁H₁₈N₆O₂ | 387.1 |
| 78 | 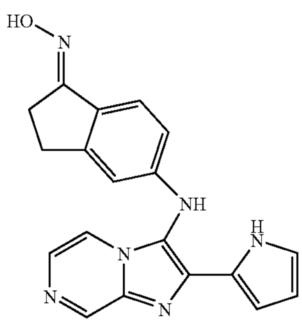 | 344.37 | C₁₉H₁₆N₆O | 345.2 |
| 79 | 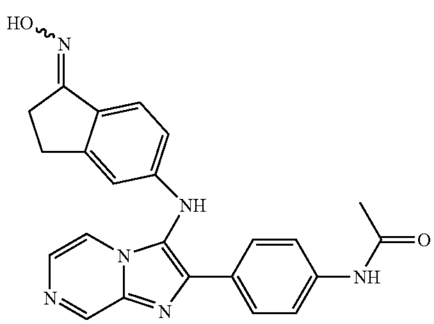 | 412.444 | C₂₃H₂₀N₆O₂ | 413.1 |
| 80 | 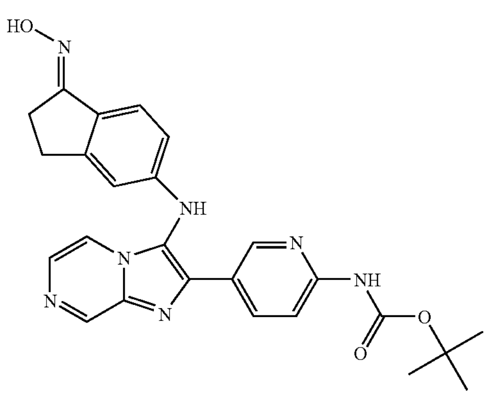 | 471.511 | C₂₅H₂₅N₇O₃ | 471.8 |

TABLE 1-continued

| Compound # | Structure | Mol. Weight | Formula | MS APCI, m/z, m + 1 |
|---|---|---|---|---|
| 81 | 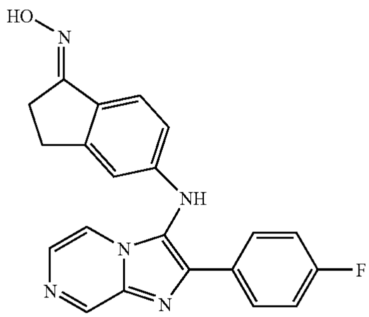 | 373.383 | C₂₁H₁₆FN₅O | 374.2 |
| 82 | 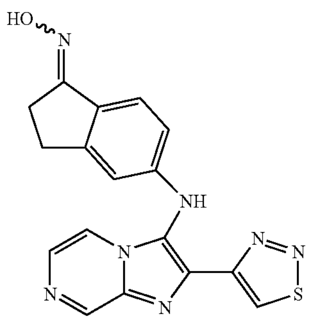 | 363.396 | C₁₇H₁₃N₇OS | 364 |
| 83 | 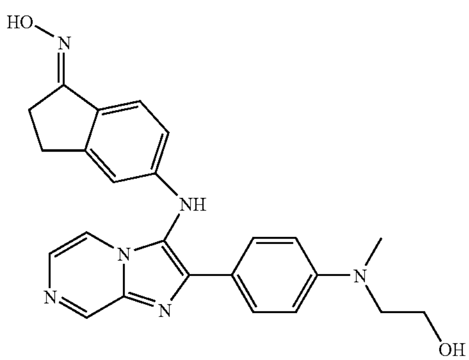 | 428.486 | C₂₄H₂₄N₆O₂ | 429.4 |
| 84 | 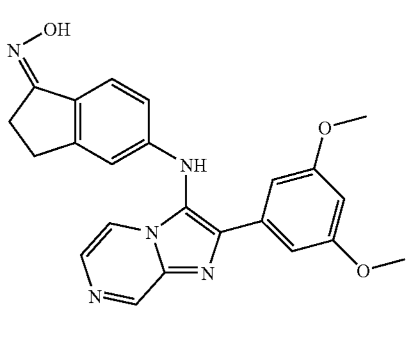 | 415.445 | C₂₃H₂₁N₅O₃ | 416 |

TABLE 1-continued

| Compound # | Structure | Mol. Weight | Formula | MS APCI, m/z, m + 1 |
|---|---|---|---|---|
| 85 | 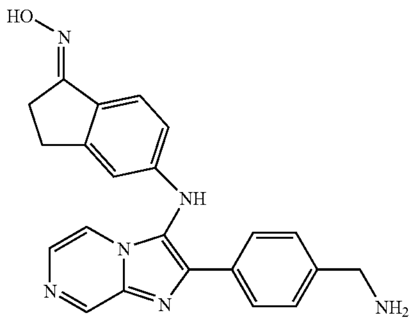 | 384.434 | $C_{22}H_{20}N_6O$ | 384.9 |
| 86 | 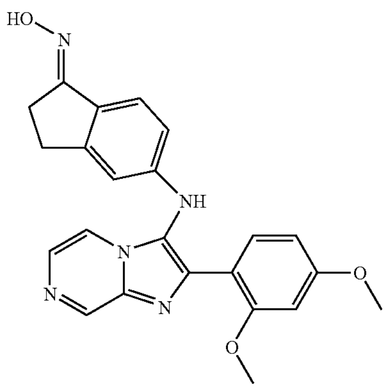 | 415.445 | $C_{23}H_{21}N_5O_3$ | 416.3 |
| 87 | 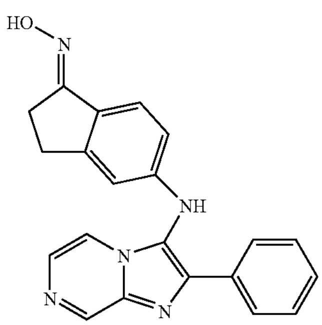 | 355.393 | $C_{21}H_{17}N_5O$ | 356.2 |
| 88 | 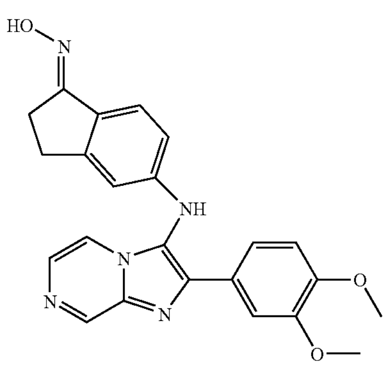 | 415.445 | $C_{23}H_{21}N_5O_3$ | 416.2 |

TABLE 1-continued

| Compound # | Structure | Mol. Weight | Formula | MS APCI, m/z, m + 1 |
|---|---|---|---|---|
| 89 | 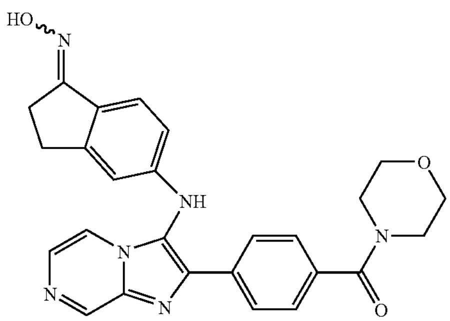 | 468.507 | C₂₆H₂₄N₆O₃ | 469.1 |
| 90 | 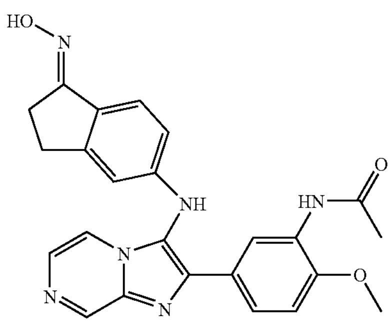 | 442.47 | C₂₄H₂₂N₆O₃ | 443.1 |
| 91 | 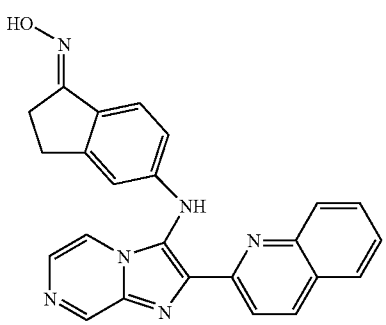 | 406.439 | C₂₄H₁₈N₆O | 407.3 |
| 92 | 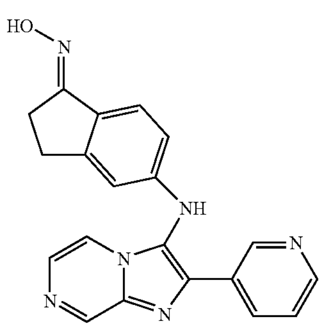 | 356.381 | C₂₀H₁₆N₆O | 357.2 |

TABLE 1-continued
| Compound # | Structure | Mol. Weight | Formula | MS APCI, m/z, m + 1 |
|---|---|---|---|---|
| 93 | 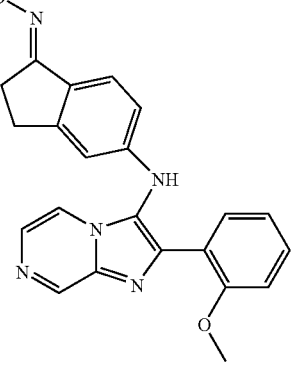 | 385.419 | $C_{22}H_{19}N_5O_2$ | 386.3 |
| 94 | 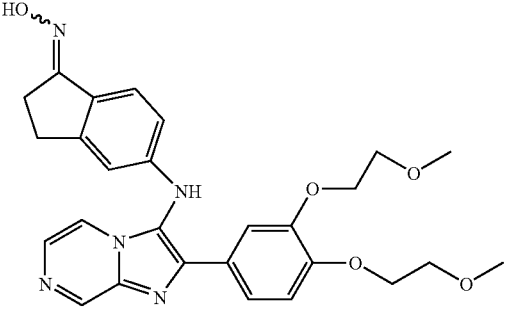 | 503.55 | $C_{27}H_{29}N_5O_5$ | 504.2 |
| 95 | 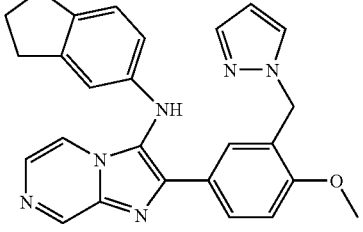 | 465.507 | $C_{26}H_{23}N_7O_2$ | 466 |
| 96 | 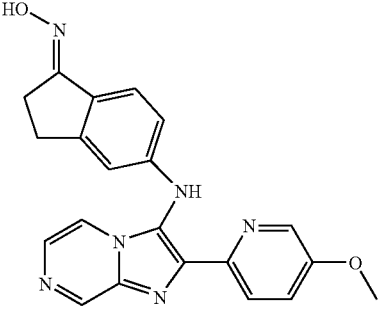 | 386.407 | $C_{21}H_{18}N_6O_2$ | 387.3 |

TABLE 1-continued
| Compound # | Structure | Mol. Weight | Formula | MS APCI, m/z, m + 1 |
|---|---|---|---|---|
| 97 | 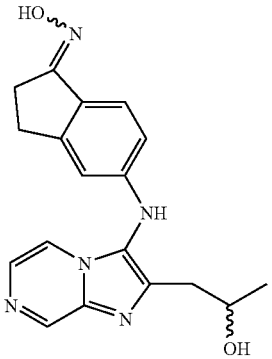 | 337.376 | $C_{18}H_{19}N_5O_2$ | 338.1 |
| 98 | 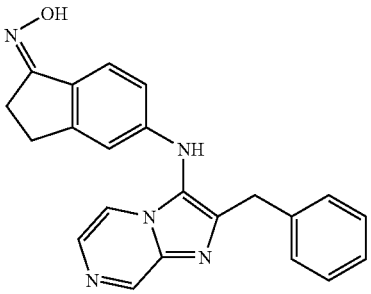 | 369.419 | $C_{22}H_{19}N_5O$ | 370 |
| 99 | 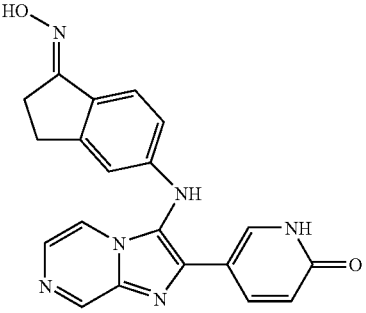 | 372.38 | $C_{20}H_{16}N_6O_2$ | 373.1 |
| 100 | 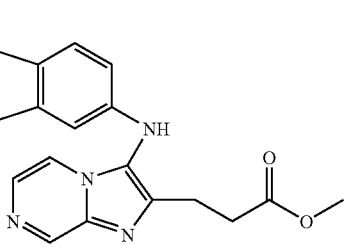 | 365.386 | $C_{19}H_{19}N_5O_3$ | 366.1 |

TABLE 1-continued

| Compound # | Structure | Mol. Weight | Formula | MS APCI, m/z, m + 1 |
|---|---|---|---|---|
| 101 | 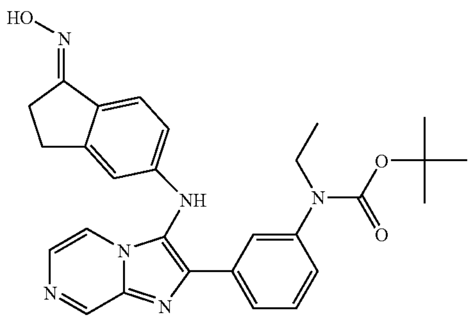 | 498.576 | $C_{28}H_{30}N_6O_3$ | 498.9 |
| 102 | 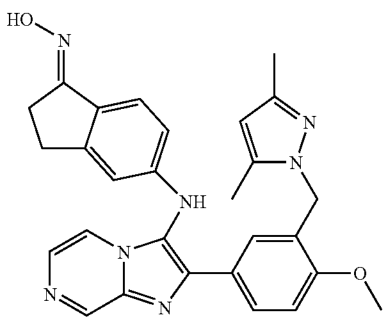 | 493.56 | $C_{28}H_{27}N_7O_2$ | 494 |
| 103 | 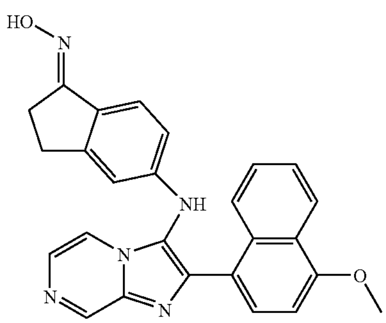 | 435.477 | $C_{26}H_{21}N_5O_2$ | 436.3 |
| 104 | 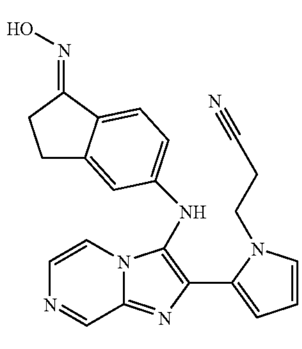 | 397.433 | $C_{22}H_{19}N_7O$ | 398.2 |

TABLE 1-continued

| Compound # | Structure | Mol. Weight | Formula | MS APCI, m/z, m + 1 |
|---|---|---|---|---|
| 105 | 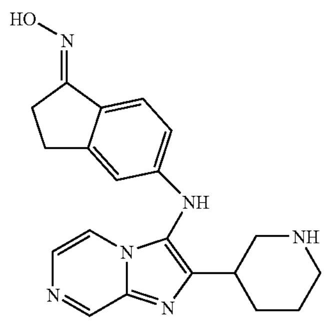 | 362.428 | $C_{20}H_{22}N_6O$ | 363.2 |
| 106 | 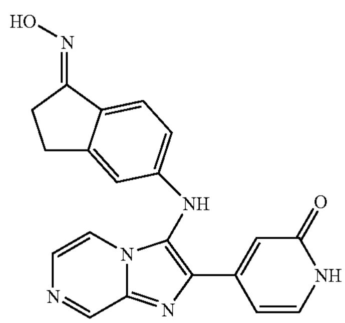 | 372.38 | $C_{20}H_{16}N_6O_2$ | 373.1 |
| 107 | 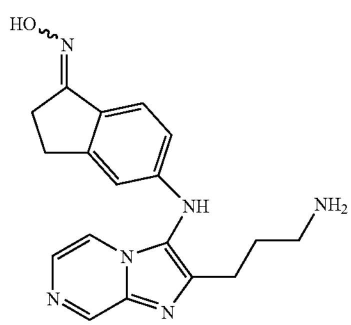 | 336.391 | $C_{18}H_{20}N_6O$ | 337 |
| 108 | 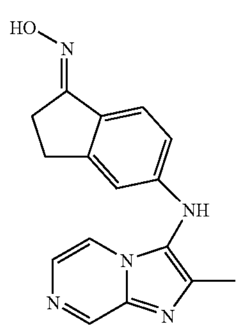 | 293.323 | $C_{16}H_{15}N_5O$ | 294.3 |

TABLE 1-continued

| Compound # | Structure | Mol. Weight | Formula | MS APCI, m/z, m + 1 |
|---|---|---|---|---|
| 109 | 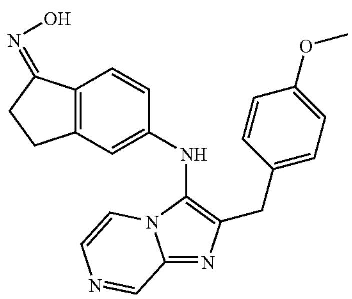 | 399.445 | $C_{23}H_{21}N_5O_2$ | 400 |
| 110 | 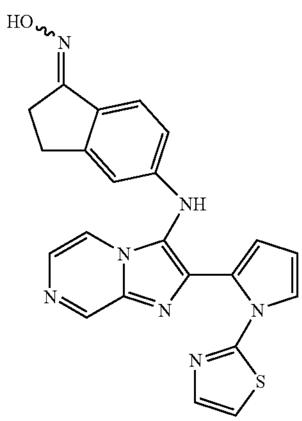 | 427.482 | $C_{22}H_{17}N_7OS$ | 428.1 |
| 111 | 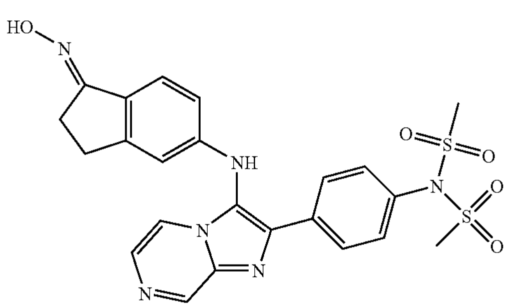 | 526.588 | $C_{23}H_{22}N_6O_5S_2$ | 527.1 |
| 112 | 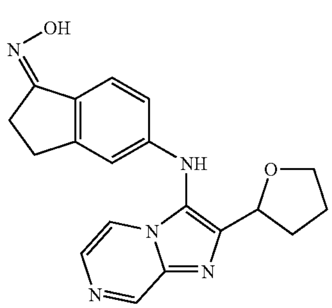 | 349.386 | $C_{19}H_{19}N_5O_2$ | 350 |

TABLE 1-continued

| Compound # | Structure | Mol. Weight | Formula | MS APCI, m/z, m + 1 |
|---|---|---|---|---|
| 113 | 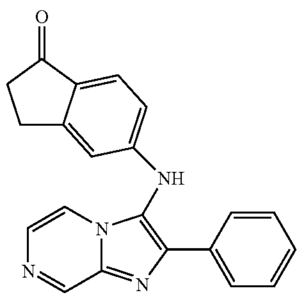 | 340.378 | $C_{21}H_{16}N_4O$ | 341.3 |
| 114 | 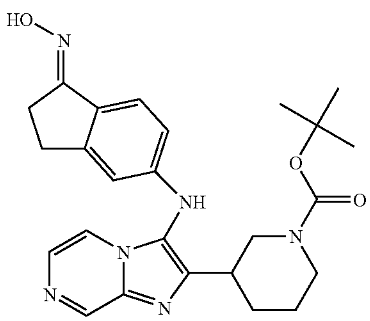 | 462.544 | $C_{25}H_{30}N_6O_3$ | 463 |
| 115 | 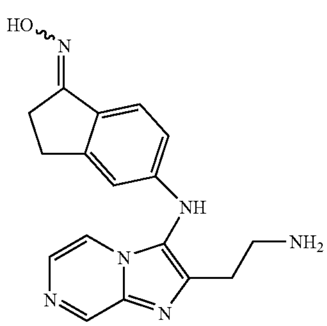 | 322.364 | $C_{17}H_{18}N_6O$ | 323.1 |
| 116 | 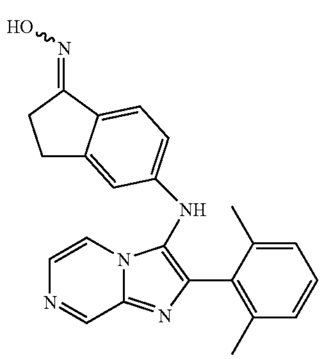 | 383.446 | $C_{23}H_{21}N_5O$ | 384.2 |

TABLE 1-continued

| Compound # | Structure | Mol. Weight | Formula | MS APCI, m/z, m + 1 |
|---|---|---|---|---|
| 117 | 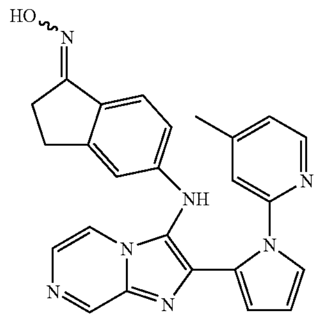 | 435.481 | $C_{25}H_{21}N_7O$ | 436.1 |
| 118 | 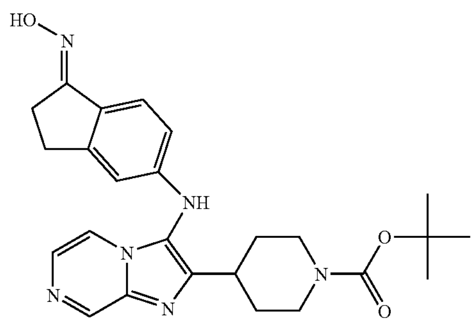 | 462.544 | $C_{25}H_{30}N_6O_3$ | 463 |
| 119 | 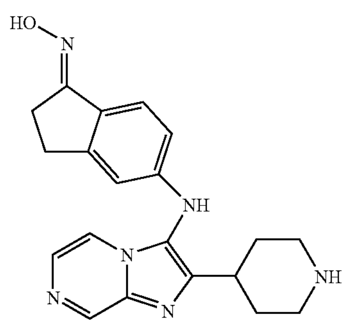 | 362.428 | $C_{20}H_{22}N_6O$ | 363.2 |

Example 11

B-Raf IC$_{50}$ Assay Protocol

Activity of human recombinant B-Raf protein may be assessed in vitro by assay of the incorporation of radiolabelled phosphate to recombinant MAP kinase (MEK), a known physiologic substrate of B-Raf, according to U.S. Patent Publication No. 2004/127496 and PCT Publication No. WO 03/022840 Catalytically active human recombinant B-Raf protein is obtained by purification from sf9 insect cells infected with a human B-Raf recombinant baculovirus expression vector. To ensure that all substrate phosphorylation resulted from B-Raf activity, a catalytically inactive form of MEK was utilized. This protein is purified from bacterial cells expression mutant inactive MEK as a fusion protein with glutathione-S-transferase (GST-kdMEK).

The activity/inhibition of V600E full-length B-Raf was estimated by measuring the incorporation of radiolabeled phosphate from [γ-$^{33}$P]ATP into FSBA-modified wild-type MEK. The 30-μL assay mixtures contained 25 mM Na Pipes, pH 7.2, 100 mM KCl, 10 mM MgCl$_2$, 5 mM β-glycerophosphate, 100 μM Na Vanadate, 4 μM ATP, 500 nCi [γ-$^{33}$P]ATP, 1 μM FSBA-MEK and 20 nM V600E full-length B-Raf. Incubations were carried out at 22° C. in a Costar 3365 plate (Corning). Prior to the assay, the B-Raf and FSBA-MEK were preincubated together in assay buffer at 1.5× (20 μL of 30 nM and 1.5 μM, respectively) for 15 minutes, and the assay was initiated by the addition of 10 μL of 12 μM ATP. Following the 60-minute incubation, the assay mixtures were quenched by the addition of 200 μL of 25% TCA, the plate was mixed on a rotary shaker for 10 minutes, and the product was captured on a Perkin-Elmer GF/B filter plate using a Tomtec Mach III Harvester. After sealing the bottom of the plate, 32 μL of Bio-Safe II (Research Products International) scintillation cocktail were added to each well and the plate was top-sealed and counted in a Topcount NXT (Packard).

Example 12

Cellular ERK ½ Phosphorylation Assay

Inhibition of basal ERK½ phosphorylation was determined by the following in vitro cellular proliferation assay, which comprises incubating cells with a compound of Formula I for 1 hour and quantifying the fluorescent pERK signal on fixed cells and normalizing to total ERK signal.

Materials and Methods: Malme-3M cells were obtained from ATCC and grown in RPMI-1640 supplemented with 10% fetal bovine serum. Cells were plated in 96-well plates at 15,000 cells/well and allowed to attach for 1-2 hours. Diluted compounds were then added at a final concentration of 1% DMSO. After 1 hour, cells were washed with PBS and fixed in 3.7% formaldehyde in PBS for 15 minutes. This was followed by washing in PBS/0.2% Triton X-100 and permeabilizing in 100% MeOH for 15 minutes. Cells were blocked in Odyssey blocking buffer (LI-COR Biosciences) for at least 1 hour. Antibodies to phosphorylated ERK (Cell Signaling #9106, monoclonal) and total ERK (Santa Cruz Biotechnology #sc-94, polyclonal) were added to the cells and incubated for at least 1 hour. After washing with PBS/0.2% TritonX-100, the cells were incubated with fluorescently-labeled secondary antibodies (goat anti-rabbit IgG-IRDye800, Rockland and goat anti-mouse IgG-Alexa Fluor 680, Molecular Probes) for an additional hour. Cells were then washed and analyzed for fluorescence at both wavelengths using the Odyssey Infrared Imaging System (LI-COR Biosciences). Phosphorylated ERK signal was normalized to total ERK signal.

Example 13

Cell Viability Assay

Viable cells after a 3 day incubation with Formula I compounds were quantified using the MTS/PMS calorimetric assay from Promega.

Materials and Methods: Malme-3M cells were plated in 96 well plates at a density of 20,000 cells/well. The cells were allowed to attach for 1-2 hours. Diluted compounds were then added to the cells at a final concentration of 0.5% DMSO. After 3 days, the number of viable cells was determined using the MTS assay (Promega, CellTiter 96 Aqueous Non-radioactive Cell Proliferation Assay). Briefly, MTS reagents were added to the cells and incubated for 1 hour. Absorbance at 490 nm was then read using a microplate reader. Background from medium only wells was subtracted.

While the invention has been described in conjunction with the enumerated embodiments, it will be understood that they are not intended to limit the invention to those embodiments. On the contrary, the invention is intended to cover all alternatives, modifications and equivalents, which may be included within the scope of the present invention as defined by the claims. Thus, the foregoing description is considered as illustrative only of the principles of the invention.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

The invention claimed is:

1. A compound of Formula I, stereoisomers, tautomers or pharmaceutically acceptable salts thereof,

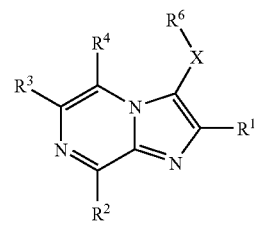

wherein:

X is $NR^5$;

$R^1$ is $C_1$-$C_{10}$ alkyl, $C_2$-$C_{10}$ alkenyl, $C_2$-$C_{10}$ alkynyl, cycloalkyl, heterocycloalkyl, $Z_n$-aryl, or heteroaryl, wherein said alkyl, alkenyl, alkynyl, cycloalkyl, heterocycloalkyl, aryl and heteroaryl portions are optionally substituted with one or more groups independently selected from F, Cl, Br, I, $NO_2$, oxo (with the proviso that it is not on said aryl or heteroaryl), alkyl, $Z_n$-aryl, $Z_n$-heterocycloalkyl, $Z_n$-heteroaryl, $Z_n$-CN, $Z_n$-$OR^{12}$, $Z_n$-C(O)$R^{12}$, $Z_n$-C(O)$OR^{12}$, $Z_n$-C(O)-heterocycloalkyl, $Z_n$-$NR^{15}R^{15}$, $Z_n$-$NR^{12}$C(O)$R^{13}$, $Z_n$-$NR^{12}$C(O)$OR^{13}$, $Z_n$-$SR^{12}$, $Z_n$-$SOR^{12}$, $Z_n$-$SO_2R^{12}$, $Z_n$-O—($C_1$-$C_6$ alkyl)-C(O)$NR^{12}R^{13}$, $Z_n$-O—($C_1$-$C_6$ alkyl)-C(O)$OR^{12}$, $Z_n$-O—($C_1$-$C_6$ alkyl)-heterocycloalkyl, $Z_n$-O—($C_1$-$C_6$ alkyl)-C(O)-heterocycloalkyl, $Z_n$-C(O)$NR^{12}R^{13}$, $Z_n$-$NR^{12}$—($C_1$-$C_6$ alkyl)-C(O)$NR^{12}R^{13}$, $Z_n$-$NR^{12}$—($C_1$-$C_6$ alkyl)-C(O)$OR^{12}$, $Z_n$-$NR^{12}$—($C_2$-$C_6$ alkyl)-OC(O)$NR^{12}R^{13}$, $Z_n$-$NR^{12}$C(=O)$NR^{13}Z_n$-$R^{16}$, and $Z_n$-$NR^{12}$—($C_2$-$C_6$ alkyl)-$NR^{12}$C(O)$NR^{12}R^{13}$;

$R^2$, $R^3$ and $R^4$ are;

$R^5$ is H, or $C_1$-$C_{10}$ alkyl;

$R^6$ is

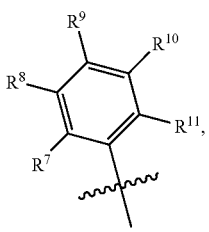

wherein (i) $R^7$ and $R^8$ form a 5 or 6 membered fused carbocyclic ring substituted with =Y, and $R^9$, $R^{10}$ and $R^{11}$ are independently selected from H, F, Cl, Br, and I, or (ii) $R^8$ and $R^9$ form a 5 or 6 membered fused carbocyclic ring substituted with =Y, and $R^7$, $R^{10}$ and $R^{11}$ are independently selected from H, F, Cl, Br, and I;

Y is O or N—OH;

$R^{12}$, $R^{13}$ and $R^{14}$ are independently selected from H, alkyl, alkenyl, alkynyl, heteroalkyl, heteroalkenyl, heteroalkynyl, cycloalkyl, heterocycloalkyl, aryl and heteroaryl, wherein said alkyl, alkenyl, alkynyl, heteroalkyl, heteroalkenyl, heteroalkynyl, cycloalkyl, heterocycloalkyl, aryl and heteroaryl are optionally substituted with one or more groups independently selected from halogen, OH, O-alkyl, amino, alkylamino and dialkylamino;

$R^{15}$ is H, —$SO_2$-alkyl, —$SO_2NR^{13}R^{14}$, ($C_1$-$C_6$ alkyl)-OH, —C(O)O-alkyl, alkyl, alkenyl, alkynyl, heteroalkyl, heteroalkenyl, heteroalkynyl, cycloalkyl, heterocycloalkyl, aryl or heteroaryl, wherein said alkyl, alkenyl, alkynyl, heteroalkyl, heteroalkenyl, heteroalkynyl, cycloalkyl, heterocycloalkyl, aryl and heteroaryl portions are optionally substituted with one or more groups independently selected from halogen, OH, O-alkyl, amino, alkylamino and dialkylamino;

$R^{16}$, is heteroaryl that is substituted with one or more alkyl, alkenyl, or alkynyl;

Z is alkylene having from 1 to 4 carbons, or alkenylene or alkynylene each having from 2 to 4 carbons, wherein said alkylene, alkenylene and alkynylene are optionally substituted with one or more groups independently selected from halogen, OH, O-alkyl, and amino; and n is 0, 1, 2, 3 or 4.

2. The compound of claim 1 wherein:

$R^1$ is $C_1$-$C_{10}$ alkyl, $C_2$-$C_{10}$ alkenyl, $C_2$-$C_{10}$ alkynyl, cycloalkyl, heterocycloalkyl, $Z_n$-aryl, or heteroaryl, wherein said alkyl, alkenyl, alkynyl, cycloalkyl, heterocycloalkyl, aryl and heteroaryl portions are optionally substituted with one or more groups independently selected from F, Cl, Br, I, $NO_2$, oxo (with the proviso that it is not on said aryl or heteroaryl) alkyl, $Z_n$-aryl, $Z_n$-heterocycloalkyl, $Z_n$-heteroaryl, $Z_n$-CN, $Z_n$-$OR^{12}$, $Z_n$-C(O)$R^{12}$, $Z_n$-C(O)O$R^{12}$, $Z_n$-C(O)-heterocycloalkyl, $Z_n$-$NR^{12}R^{15}$, $Z_n$-$NR^{12}$C(O)$R^{13}$, $Z_n$-$NR^{12}$C(O)O$R^{13}$, $Z_n$-$SR^{12}$, $Z_n$-$SOR^{12}$, $Z_n$-$SO_2R^{12}$, $Z_n$-O—($C_1$-$C_6$ alkyl)-C(O)$NR^{12}R^{13}$, $Z_n$-O—($C_1$-$C_6$ alkyl)-C(O)O$R^{12}$, $Z_n$-O—($C_1$-$C_6$ alkyl)-heterocycloalkyl, $Z_n$-O—($C_1$-$C_6$ alkyl)-C(O)$NR^{12}R^{13}$, $Z_n$-$NR^{12}$—($C_1$-$C_6$ alkyl)-C(O)$NR^{12}R^{13}$, $Z_n$-$NR^{12}$—($C_1$-$C_6$ alkyl)-C(O)O$R^{12}$, $Z_n$-$NR^{12}$—($C_2$-$C_6$ alkyl)-OC(O)$NR^{12}R^{13}$, $Z_n$-$NR^{12}$C(=O)$NR^{13}$ and $Z_n$-$NR^{12}$—($C_2$-$C_6$ alkyl)-$NR^{12}$C(O)$NR^{12}R^{13}$; and $R^{15}$ is H, —$SO_2$-alkyl, —$SO_2NR^{13}R^{14}$, ($C_1$-$C_6$ alkyl)-OH, —C(O)O-alkyl, alkyl, alkenyl, alkynyl, heteroalkyl, heteroalkenyl, heteroalkynyl, cycloalkyl, heterocycloalkyl, aryl or heteroaryl, wherein said alkyl, alkenyl, alkynyl, heteroalkyl, heteroalkenyl, heteroalkynyl, cycloalkyl, heterocycloalkyl, aryl and heteroaryl portions are optionally substituted with one or more groups independently selected from halogen, OH, O-alkyl, and amino.

3. The compound of claim 1, where Y is N—OH.

4. The compound of claim 1, where Y is O.

5. The compound of claim 2, wherein $R^1$ is aryl.

6. The compound of claim 5, wherein said aryl is substituted with one or more groups independently selected from $Z_n$-$OR^{12}$, $Z_n$-C(O)O$R^{12}$, $Z_n$-$NR^{12}R^{15}$, $Z_n$-$NR^{12}$C(O)$R^{13}$, $Z_n$-O—($C_1$-$C_6$ alkyl)-C(O)$NR^{12}R^{13}$ and $Z_n$-O—($C_1$-$C_6$ alkyl)-C(O)O$R^{12}$.

7. The compound of claim 1, wherein $R^1$ is heteroaryl.

8. The compound of claim 7, wherein said heteroaryl is substituted with one or more groups independently selected from alkyl and $Z_n$-$OR^{12}$.

9. The compound of claim 1, wherein $R^7$ $R^8$ form a 5 membered fused carbocyclic ring.

10. The compound of claim 1, wherein $R^1$ is selected from 2-pyridyl, 3-pyridyl, 4-pyridyl, 2-imidazolyl, 4-imidazolyl, 3-pyrazolyl, 4-pyrazolyl, 2-pyrrolyl, 3-pyrrolyl, 2-thiazolyl, 4-thiazolyl, 5-thiazolyl, 3-pyridazinyl, 4-pyridazinyl, 5-pyridazinyl, 2-pyrimidinyl, 5-pyrimidinyl, 6-pyrimidinyl, 2-pyrazinyl, 2-oxazolyl, 4-oxazolyl, 5-oxazolyl, 2-furanyl, 3-furanyl, 2-thienyl, 3-thienyl, phenyl and 3-indolyl, wherein the 2-pyridyl, 3-pyridyl, 4-pyridyl, 2-imidazolyl, 4-imidazolyl, 3-pyrazolyl, 4-pyrazolyl, 2-pyrrolyl, 3-pyrrolyl, 2-thiazolyl, 4-thiazolyl, 5-thiazolyl, 3-pyridazinyl, 4-pyridazinyl, 5-pyridazinyl, 2-pyrimidinyl, 5-pyrimidinyl, 6-pyrimidinyl, 2-pyrazinyl, 2-oxazolyl, 4-oxazolyl, 5-oxazolyl, 2-furanyl, 3-furanyl, 2-thienyl, 3-thienyl, phenyl, and 3-indolyl may be optionally substituted with one or more groups independently selected from F, Cl, Br, I, $NO_2$, alkyl, $Z_n$-aryl, $Z_n$-heterocycloalkyl, $Z_n$-heteroaryl, $Z_n$-CN, $Z_n$-$OR^{12}$, $Z_n$-C(O)$R^{12}$, $Z_n$-C(O)O$R^{12}$, $Z_n$-C(O)-heterocycloalkyl, $Z_n$-$NR^{15}R^{15}$, $Z_n$-$NR^{12}$C(O)$R^{13}$, $Z_n$-$NR^{12}$C(O)O$R^{13}$, $Z_n$-$SR^{12}$, $Z_n$-$SOR^{12}$, $Z_n$-$SO_2R^{12}$, $Z_n$-O—($C_1$-$C_6$ alkyl)-C(O)$NR^{12}R^{13}$, $Z_n$-O—($C_1$-$C_6$ alkyl)-C(O)O$R^{12}$, $Z_n$-O—($C_1$-$C_6$ alkyl)-heterocycloalkyl, $Z_n$-O—($C_1$-$C_6$ alkyl)-C(O)-heterocycloalkyl, $Z_n$-C(O)$NR^{12}R^{13}$, $Z_n$-$NR^{12}$—($C_1$-$C_6$ alkyl)-C(O)$NR^{12}R^{13}$, $Z_n$-$NR^{12}$—($C_1$-$C_6$ alkyl)-C(O)O$R^{12}$, $Z_n$-$NR^{12}$—($C_2$-$C_6$ alkyl)-OC(O)$NR^{12R13}$, $Z_n$-$NR^{12}$C(=O)$NR^{13}$ $Z_n$-$R^{16}$, and $Z_n$-$NR^{12}$—($C_2$-$C_6$ alkyl)-$NR^{12}$C(O)$NR^{12}R^{13}$.

11. The compound of claim 1, wherein $R^1$ is selected from phenyl, 2-furanyl, 2-thiazolyl, 2-pyrrolyl, 3-indolyl and 3-pyridyl.

12. The compound of claim 1 selected from Formulas Ia and Ib:

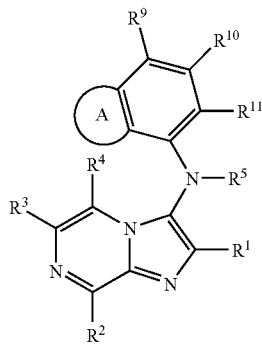

Ia

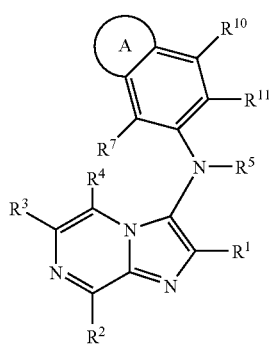

Ib where A is a 5 or 6 membered fused carbocyclic ring substituted with =Y.

13. The compound of claim 1, selected from Formulas Ic-Ip:

-continued
Ic
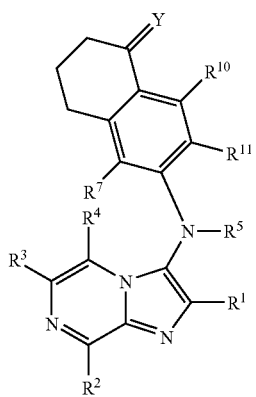
Ig
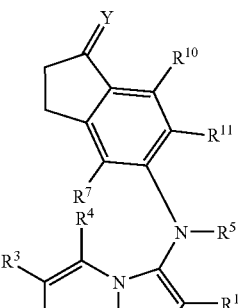
Id
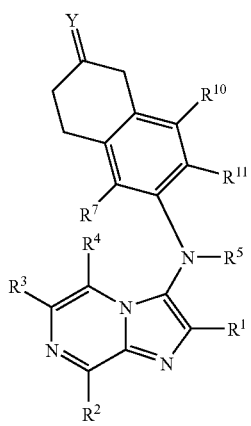
Ih
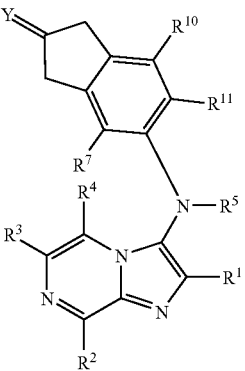
Ie
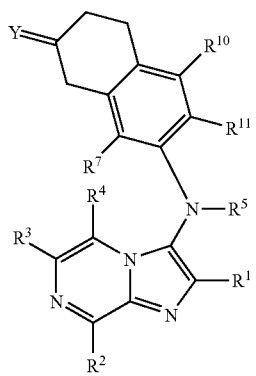
Ii
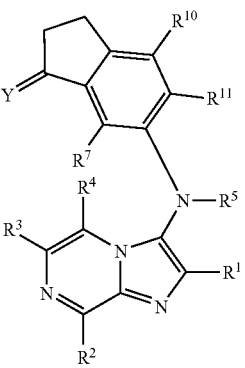
If
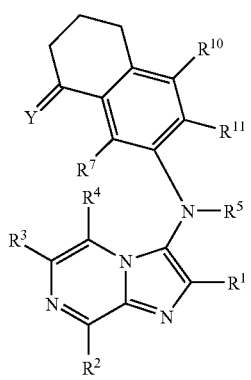
Ij
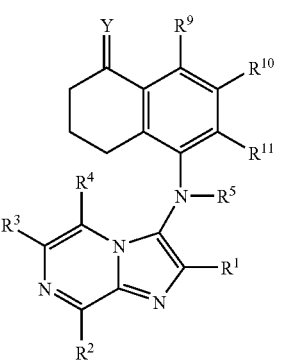

Ik
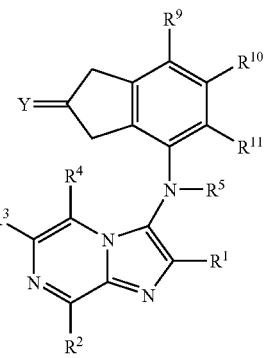
Il
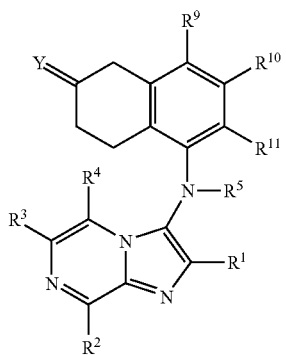
Im
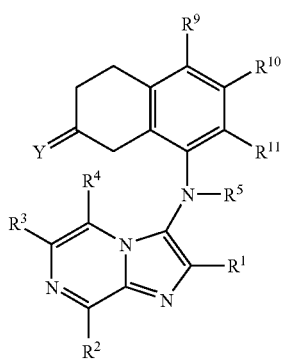
In
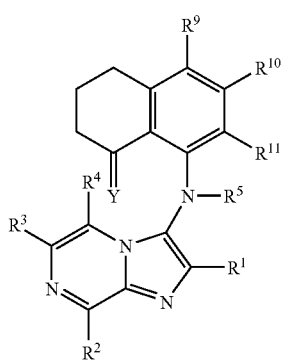
Io
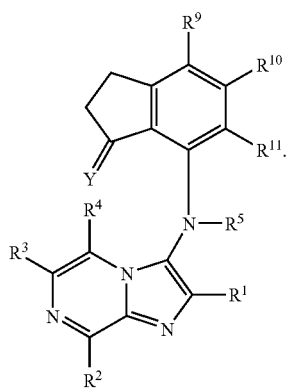
Ip
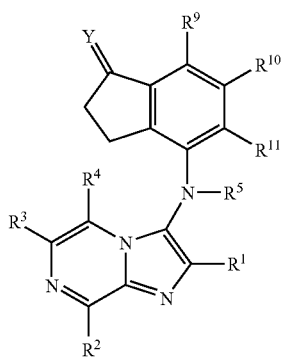
14. The compound of claim 1, selected from Formulas Iq-Idd:
Iq
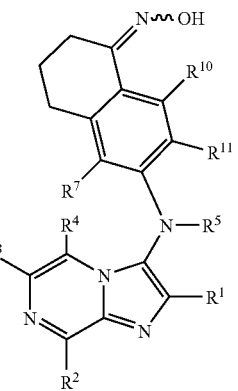

-continued
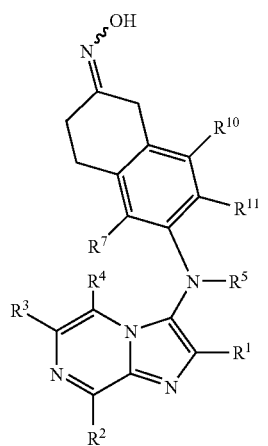
Ir
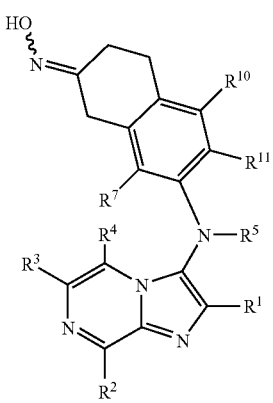
Is
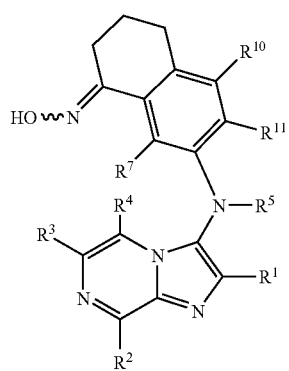
It
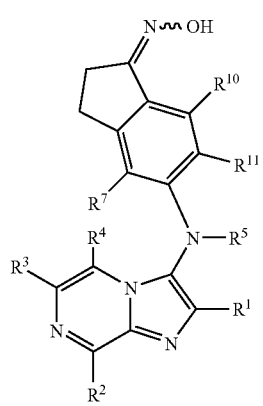
Iu
-continued
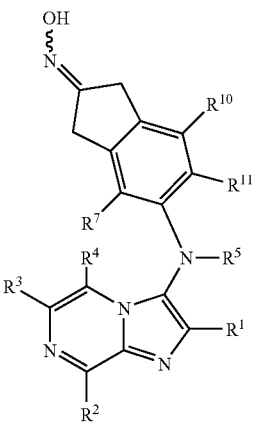
Iv
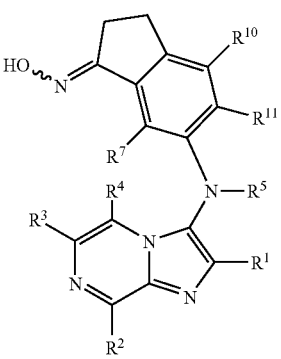
Iw
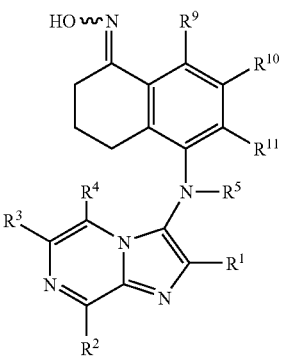
Ix
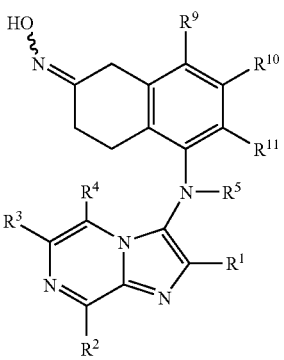
Iy -continued
Iz
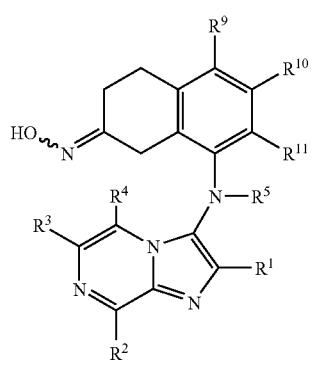
Iaa
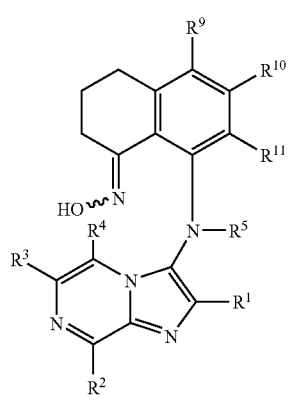
Ibb
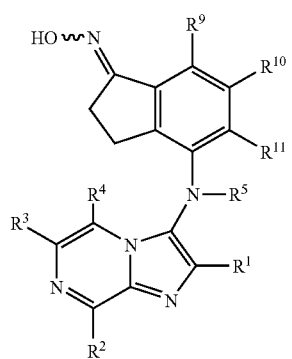
Icc
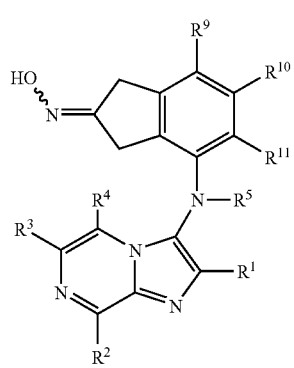
-continued
Idd
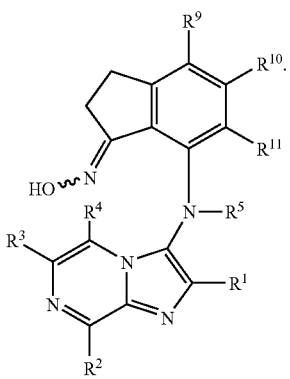
15. The compound of claim 1, selected from
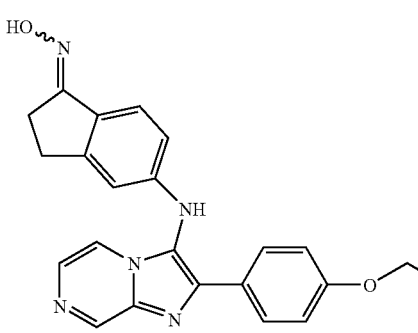
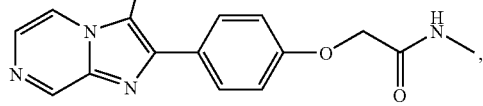
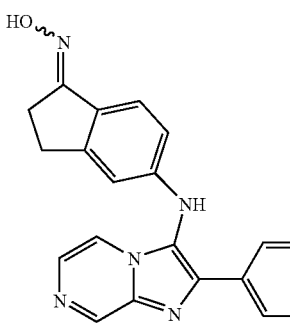
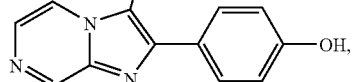
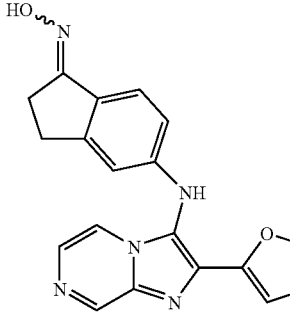
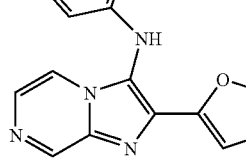

-continued
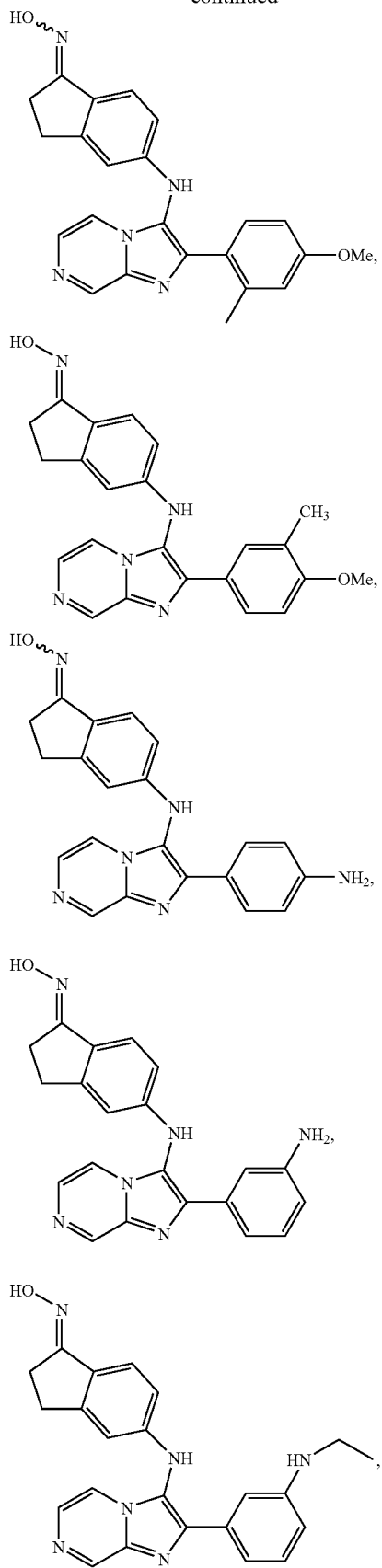
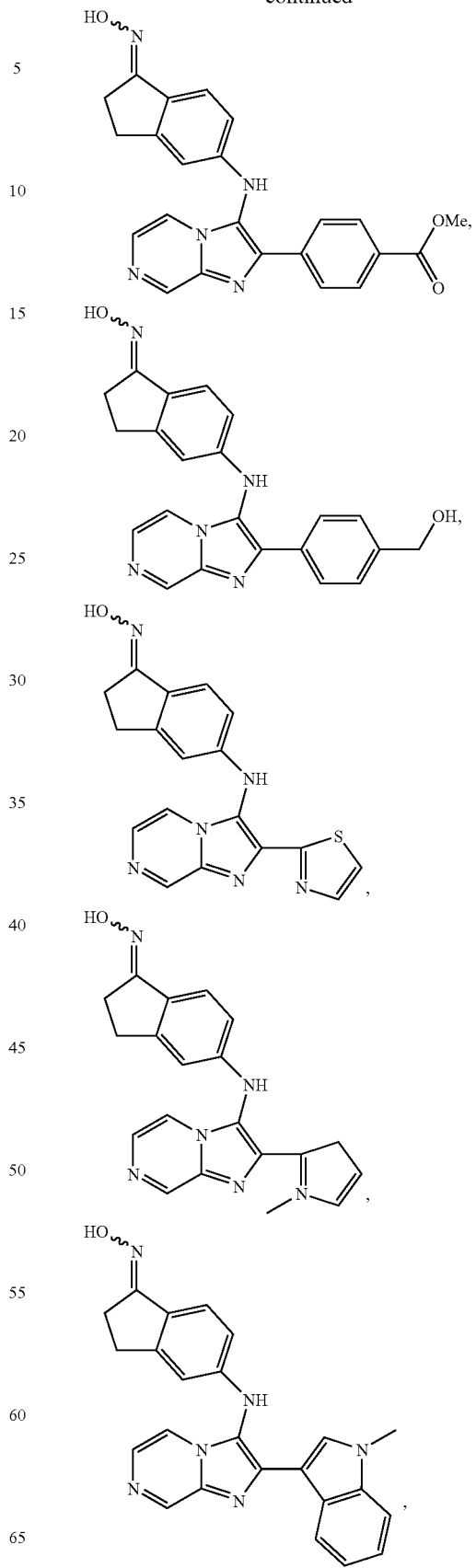

-continued

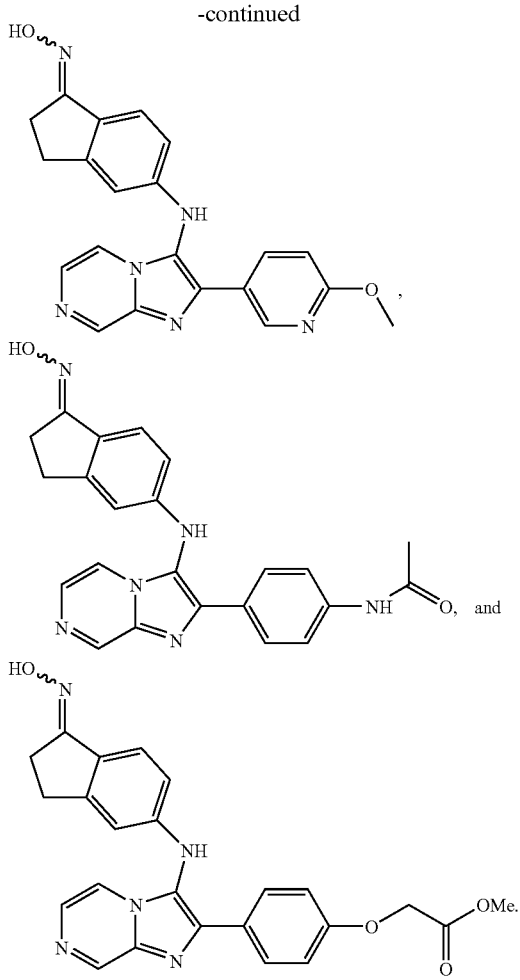

16. The compound of claim 1 wherein R¹ is aryl optionally substituted with one or more hydroxymethyl, methylaminocarbonylmethoxy, amino, 2-(dimethylamino)-ethylaminocarbonyl, methoxycarhonylmethoxy, ethylamino, acylamino, dimethylaminocarbonylmethoxy, carboxymethoxy, hydroxy, aminocarbonylmethoxy,methoxy, fluoro, methyl, methylaminocarbonyl, morpholinocarbonylmethoxy, N-(2-methoxyethyl)-N-methylaminocarbonylmethoxy, isopropylaminocarbonyl, methoxycarbonyl, carboxy, acylaminomethyl, nitro, methylsulfonylamino, morpholino, methylsulfonyl, dimethylamino, cyano, methylthio, tert-butoxycarbonylamino, N-(2-hydroxyethyl)methylamino, aminomethyl, morpholinocarbonyl, 2-methoxyethoxy, pyrazol-1-yl, N-(tert-butoxycarbonyl)ethylamino, 3,5-dimethylpyrazol-1-yl, or N,N-di(methylsulfonyl)amino.

17. The compound of claim 16 wherein R¹ is phenyl optionally substituted with one or more hydroxymethyl, methylaminocarbonylmethoxy, amino, 2-(dimethylamino)-ethylaminocarbonyl, methoxycarbonylmethoxy, ethylamino, acylamino, dimethylaminocarbonylmethoxy, carboxymethoxy, hydroxy, aminocarbonylmethoxy,methoxy, fluoro, methyl, methylaminocarbonyl, morpholinocarbonylmethoxy, N-(2-methoxyethyl)-N-methylaminocarbonylmethoxy, isopropylaminocarbonyl, methoxycarbonyl, carboxy, acylaminomethyl, nitro, methylsulfonylamino, morpholino, methylsulfonyl, dimethylamino, cyano, methylthio, tert-butoxycarbonylamino, N-(2-hydroxyethyl)methylamino, aminomethyl, morpholinocarbonyl, 2-methoxyethoxy, pyrazol-1-yl, N-(tert-butoxycarbonyl)ethylamino, 3,5-dimethylpyrazol-1-yl, or N,N-di(methylsulfonyl)amino.

18. The compound of claim 1 wherein R¹ is 1-methyl-1H-indol-3-yl, 2-furyl, 2-thienyl, 2-thiazoyl, 1-methylpyrazol-4-yl, 3-furyl, 6-aminopyrid-3-yl1-methylpyrol-2-yl, 1-ethyl-2-oxo-1,2-dihydropyrid-5-yl, 1-(pyrid-3-yl)pyrrol-2-yl, 3-thienyl, 5-thiazolyl, 5-cyano-6-methylthiopyrid-2-yl, 6-methoxypyrid-3-yl, 2-pyrrolyl, 6-(tert-butoxycarbonylamino)pyrid-3-yl, 1,2,3thiadiazole-4-yl, 2-quinolyl, 3-pyridyl, 5-methoxypyrid-2-yl, 2-hydroxypropyl, benzyl, 2-oxo-1,2-dihydropyrid-5-yl, 2-(methoxycarbonyl)ethyl, 1-(2-cyanoethyl)pyrrol-2-yl, 3-piperidinyl, 2-oxo-1,2-dihydropyrid-4-yl, 3-aminopropyl, methyl, 4-methoxybenzyl, 1-(2-thiazolyl)pyrrol-2-yl, 2-tetrahydrofuranyl, 1-(tertbutoxycarbonyl)piperidin-3-yl, 2-aminoethyl, 1-(4-methylpyrid-2-yl))pyrrol-2-yl, 1-(tertbutoxycarbonyl)piperidin-4-yl, or 4-piperidyl.

19. A compound selected from compounds:

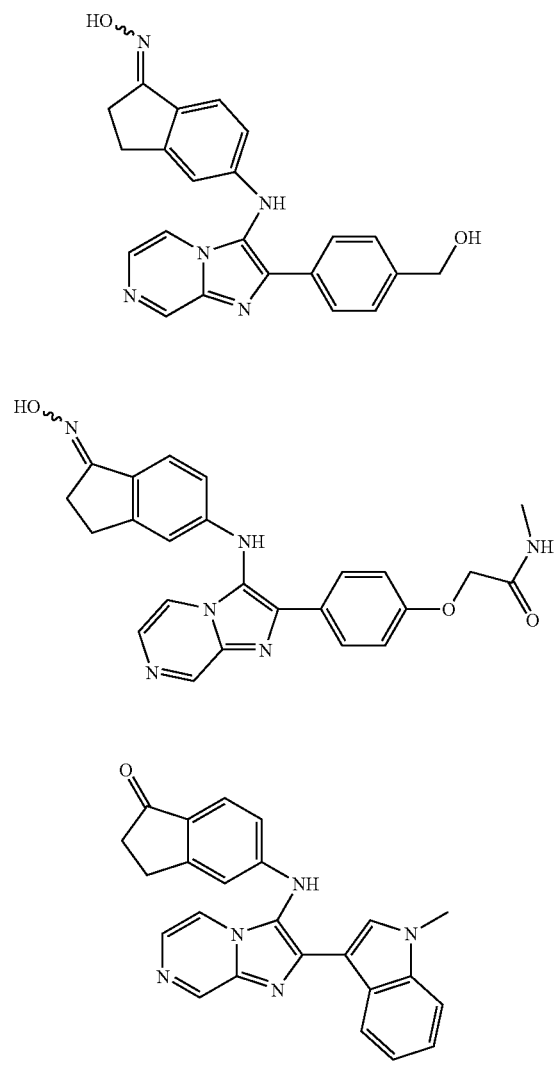

113
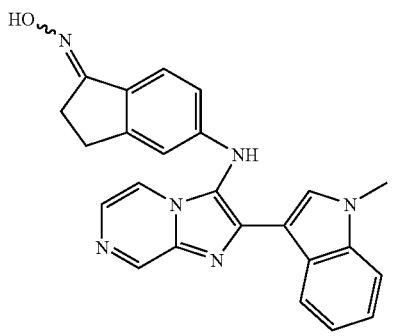
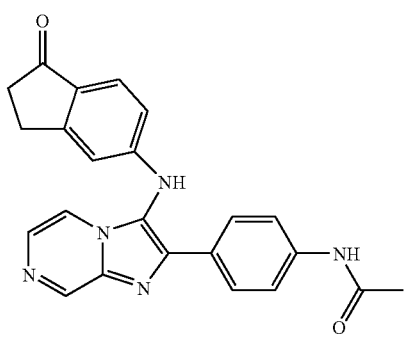
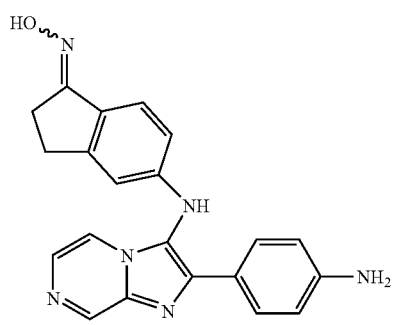
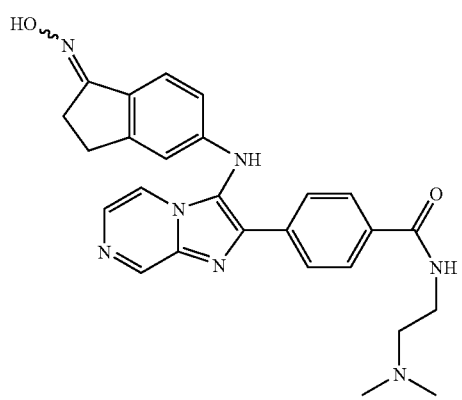
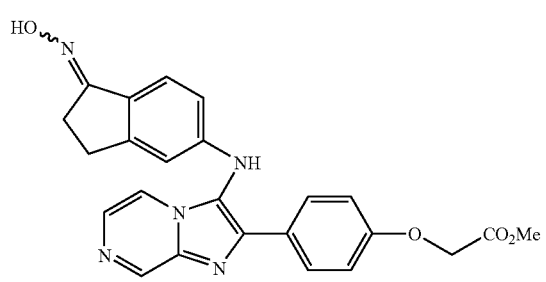
114
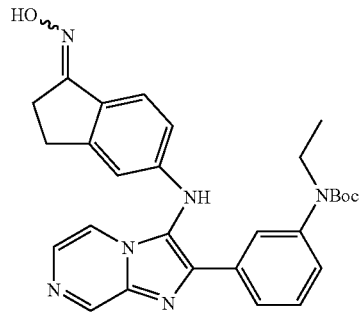
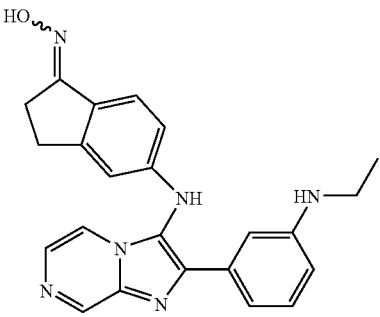
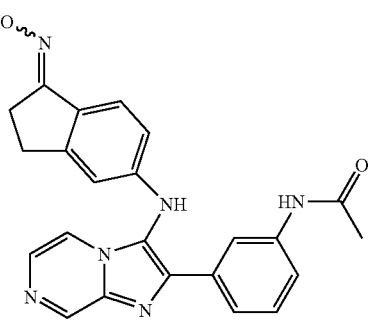
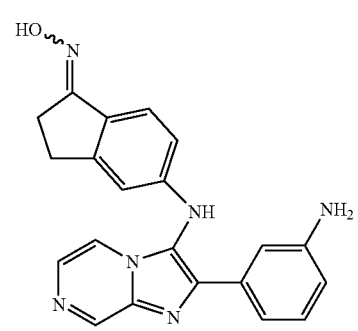
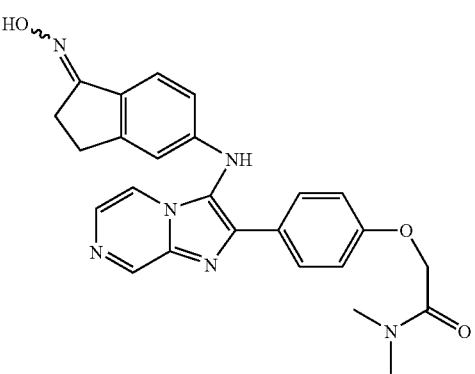

115
-continued
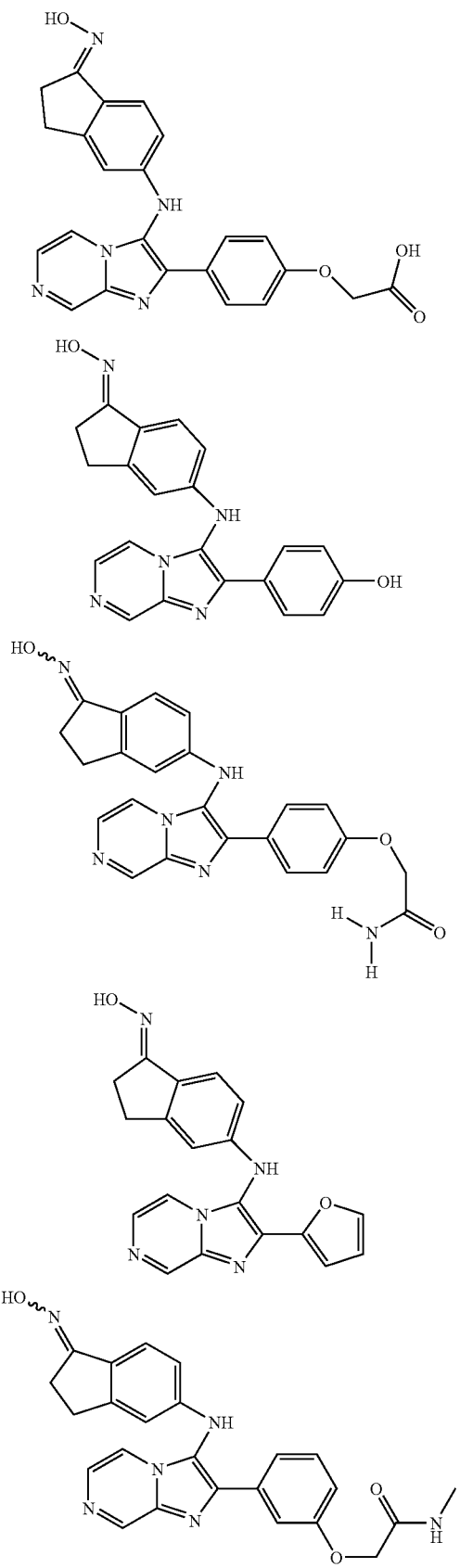
116
-continued
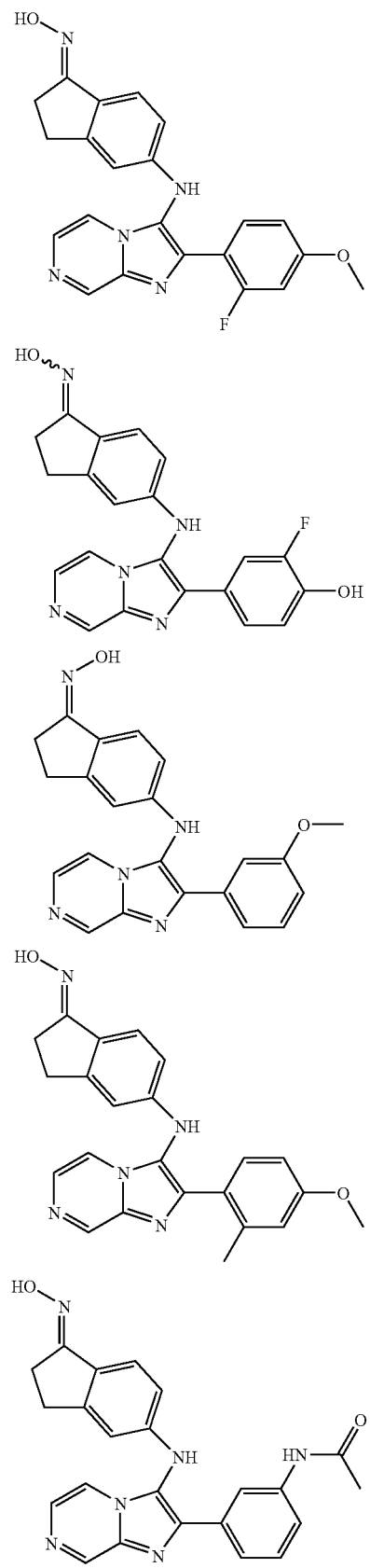

117                                             118
-continued                                      -continued
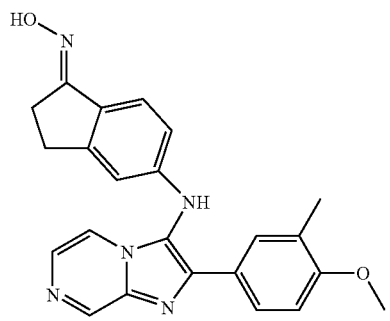
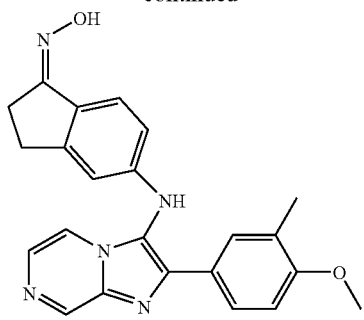
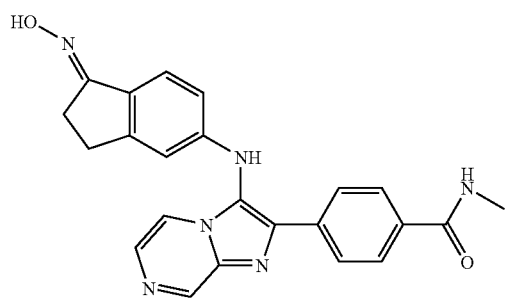
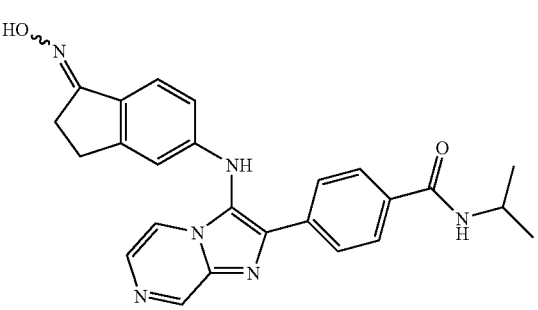
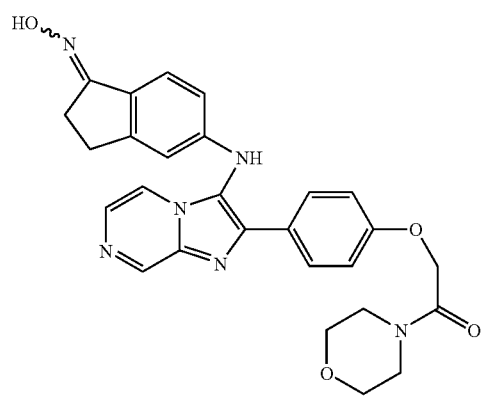
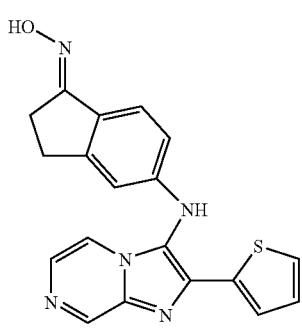
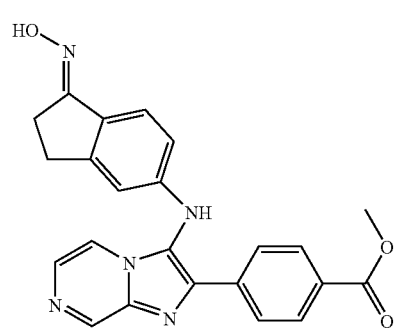
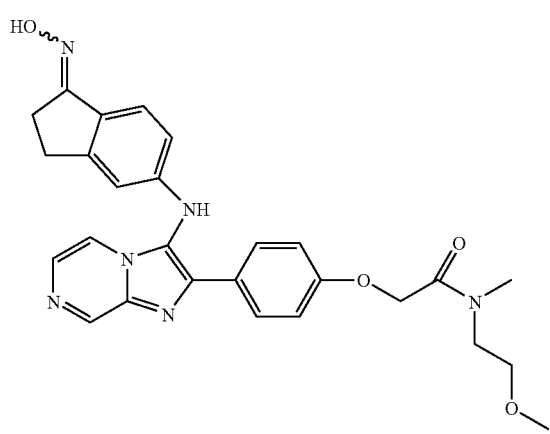
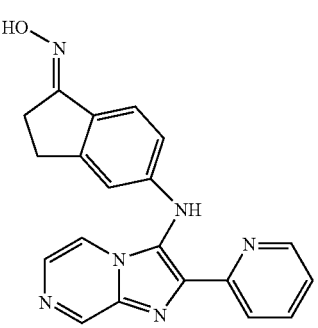

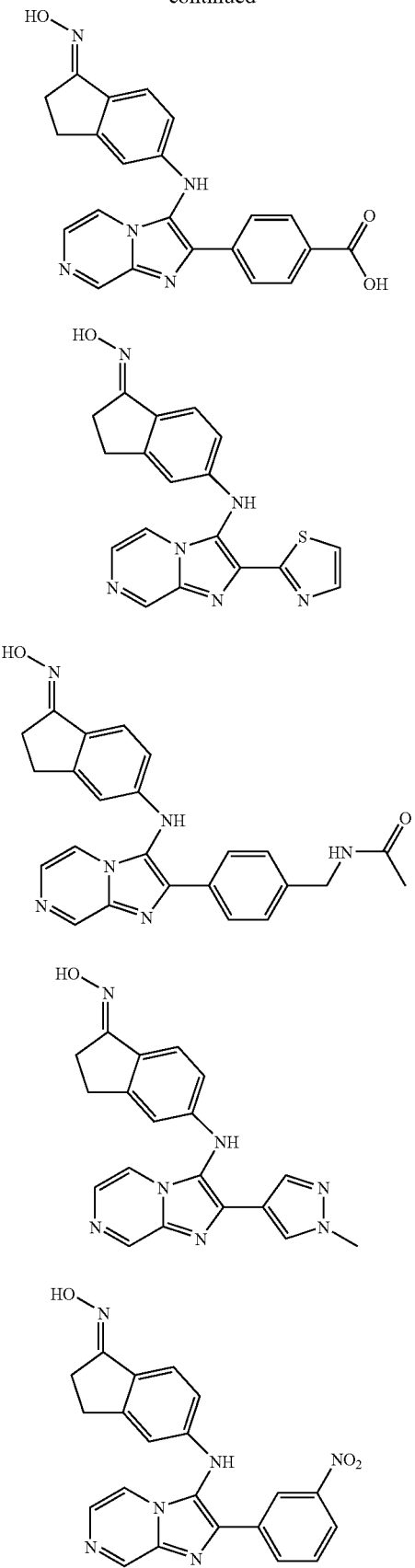
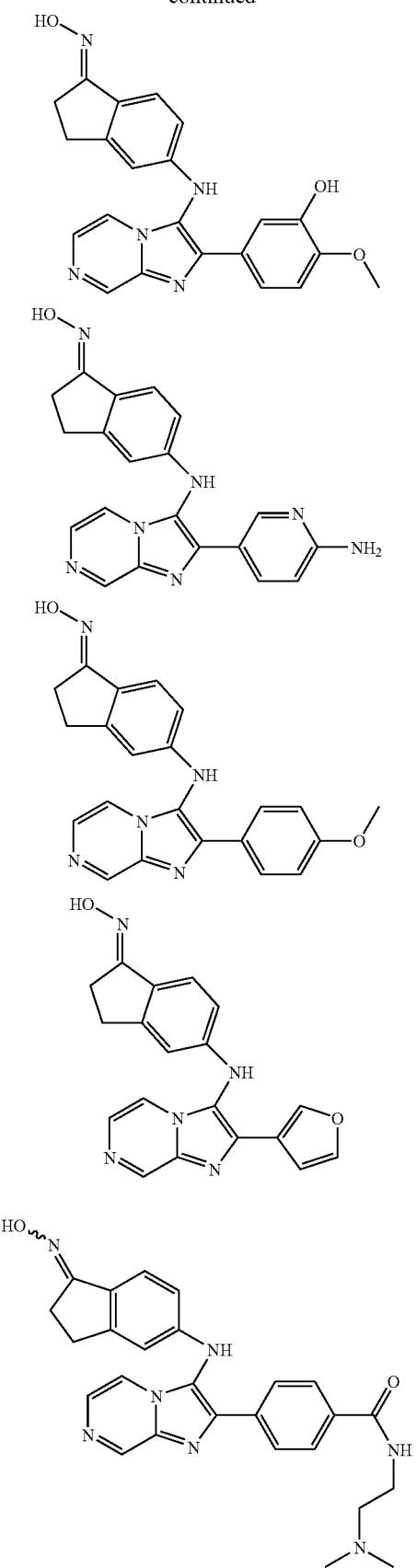

121
-continued
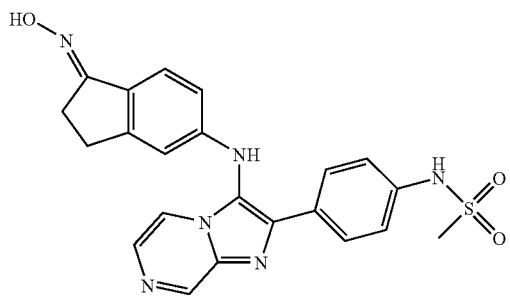
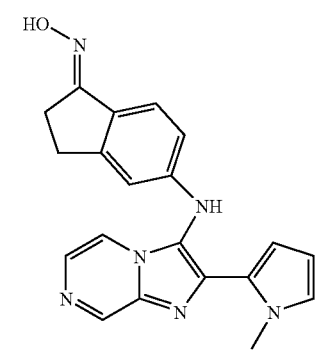
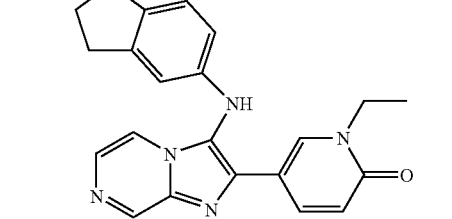
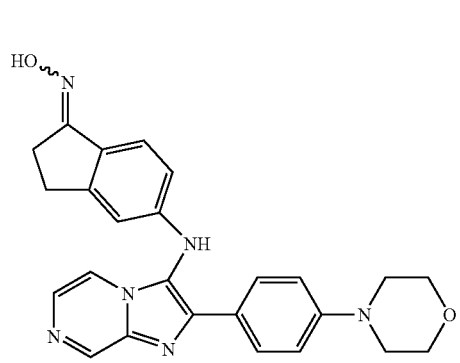
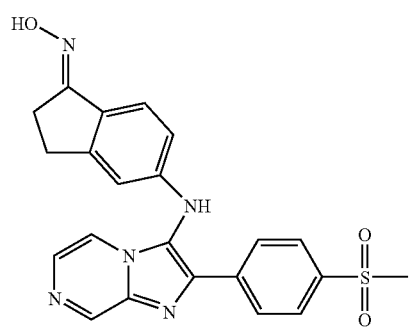
122
-continued
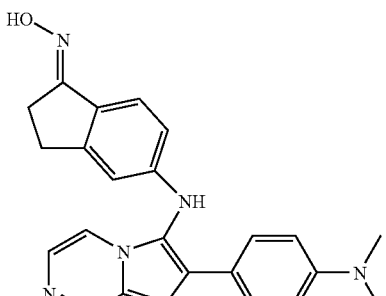
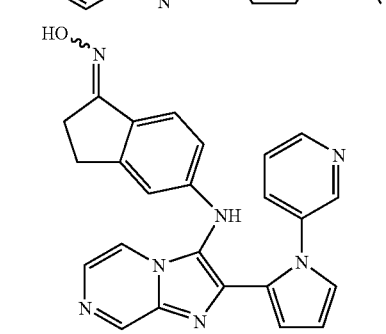
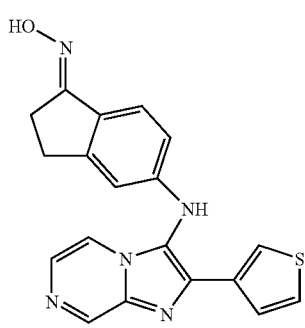
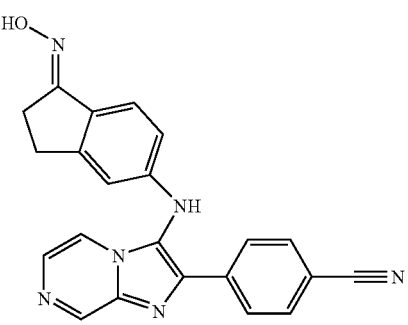
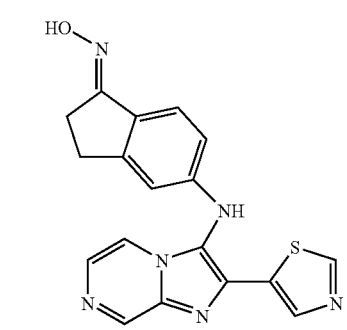

123
-continued
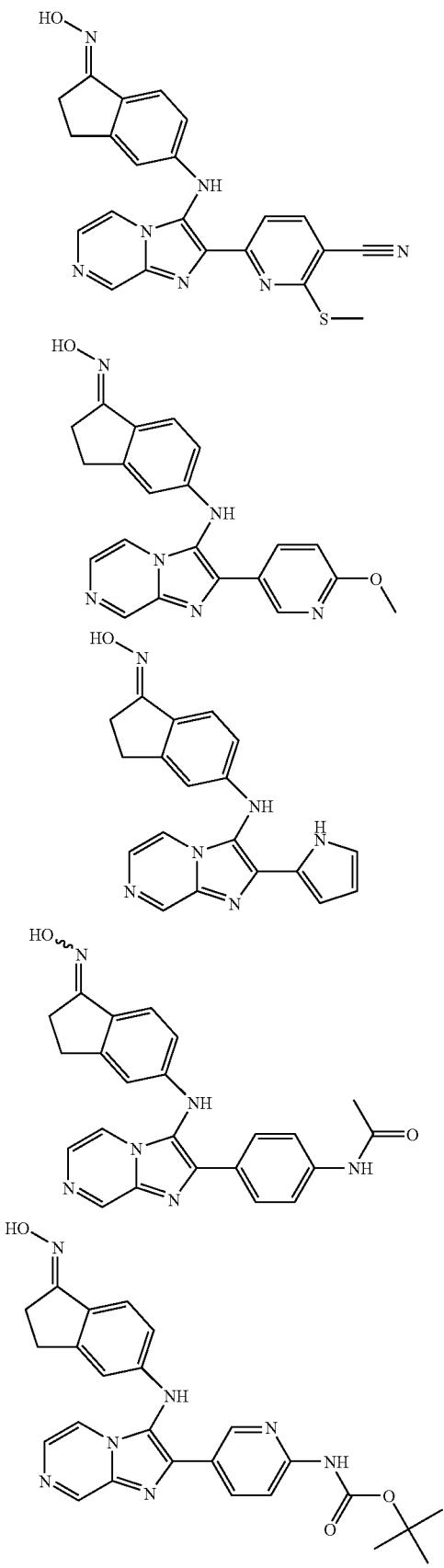
124
-continued
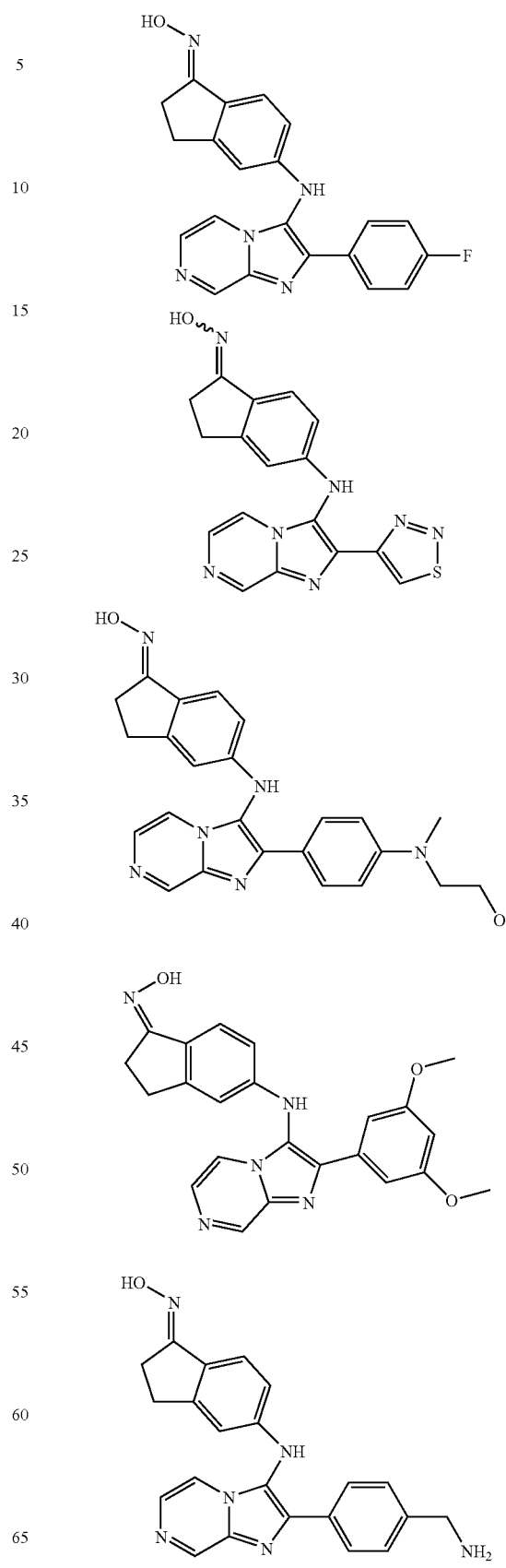

-continued
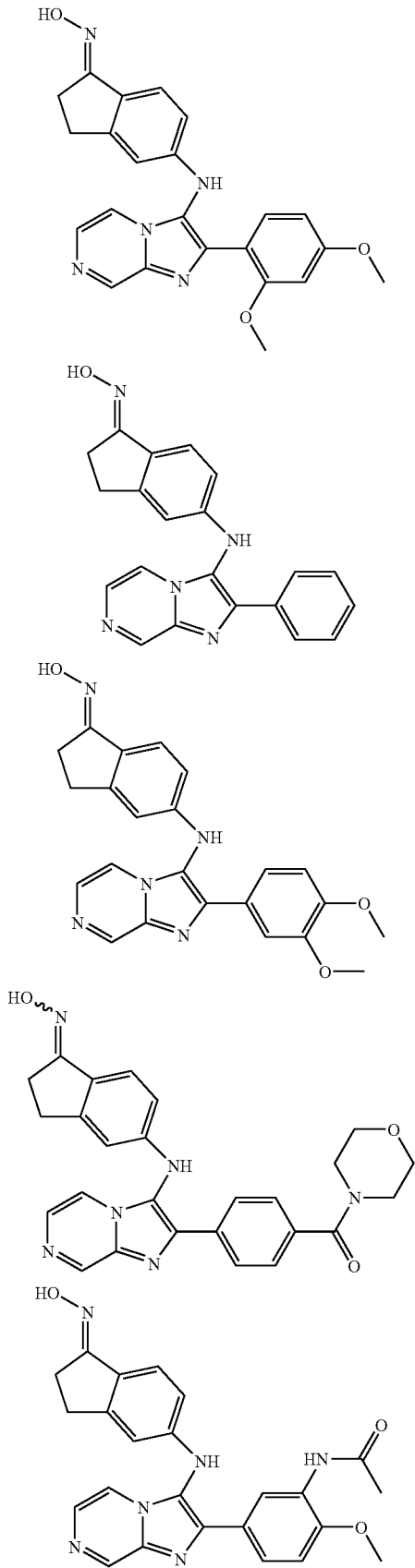
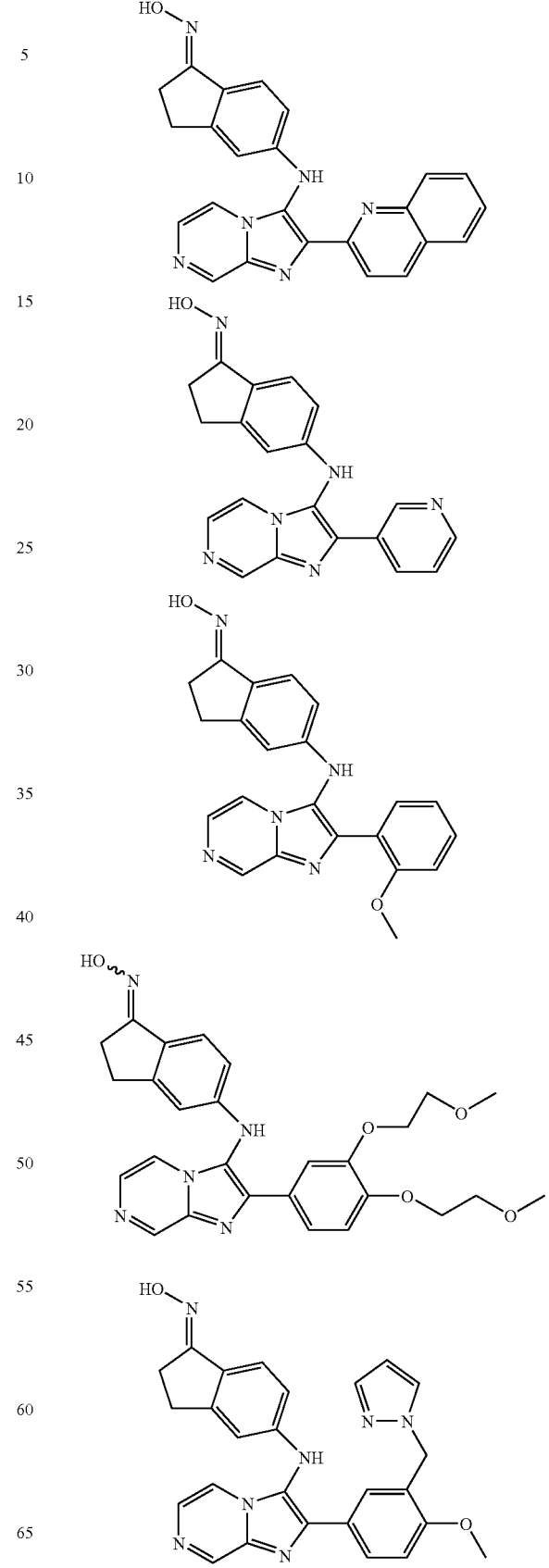

127
-continued
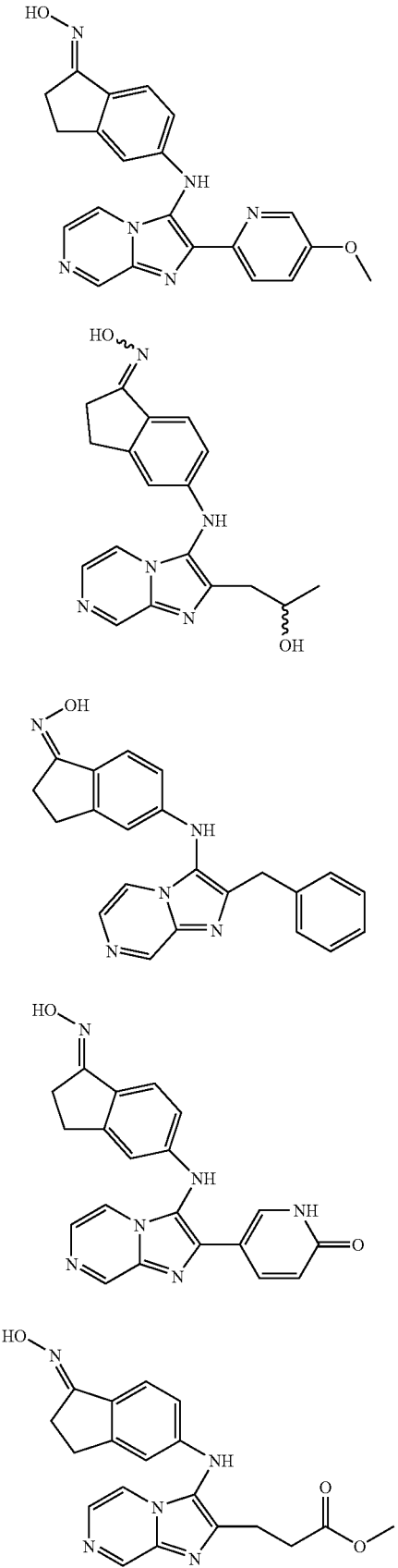
128
-continued
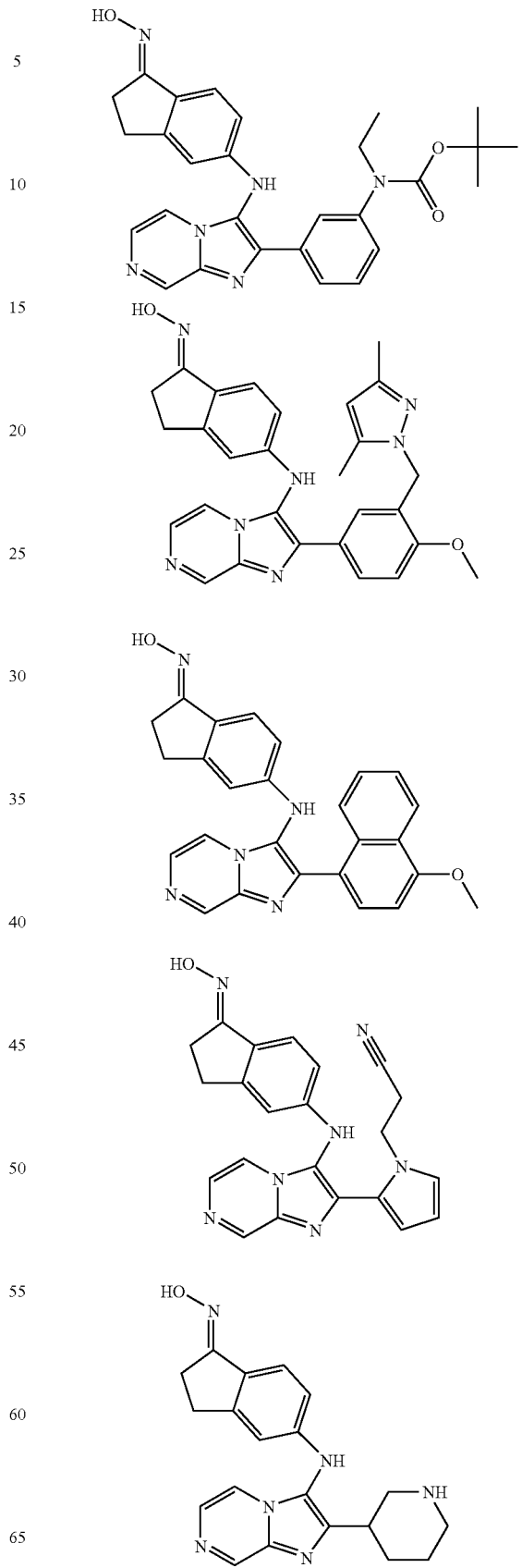

-continued
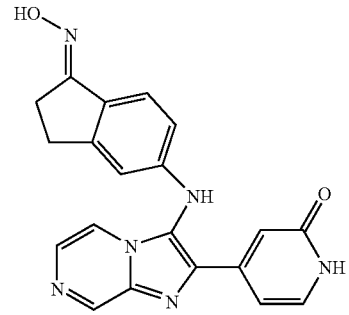
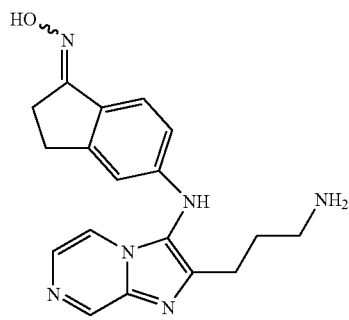
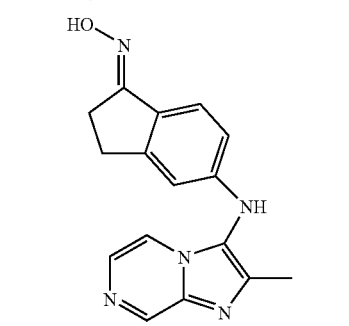
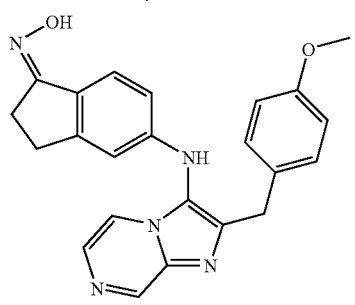
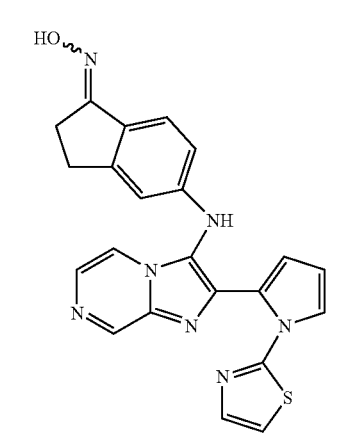
-continued
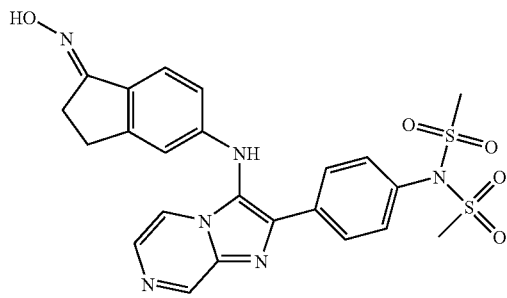
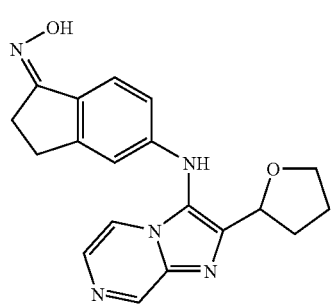
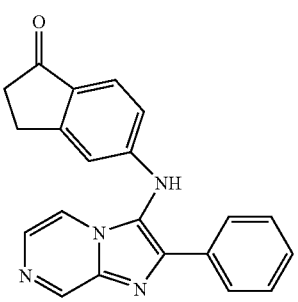
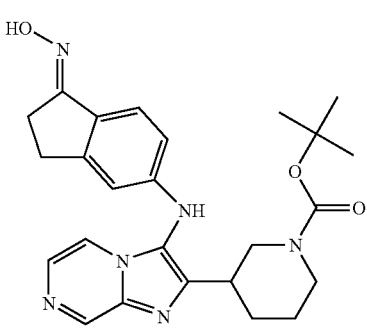
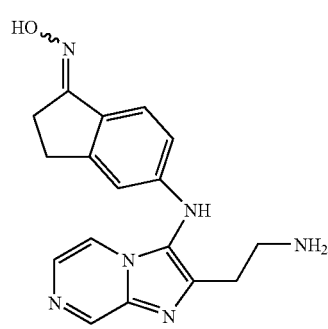

-continued

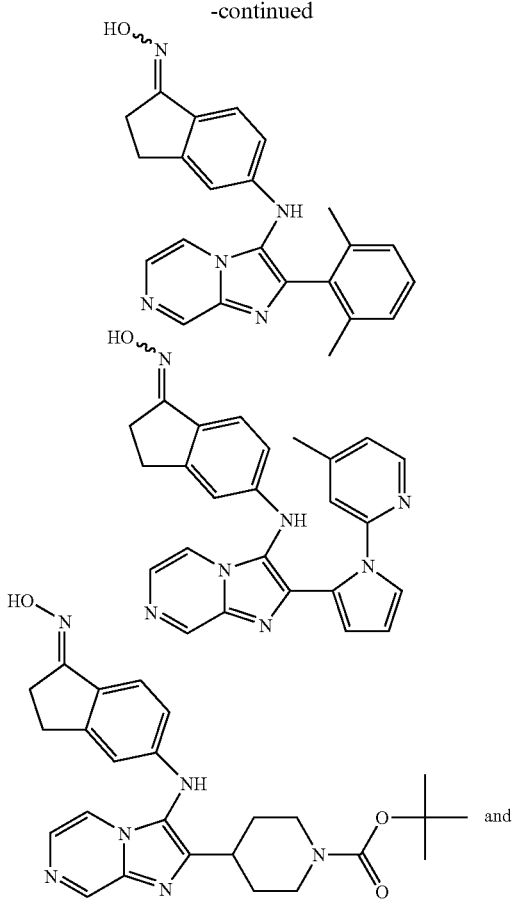

-continued

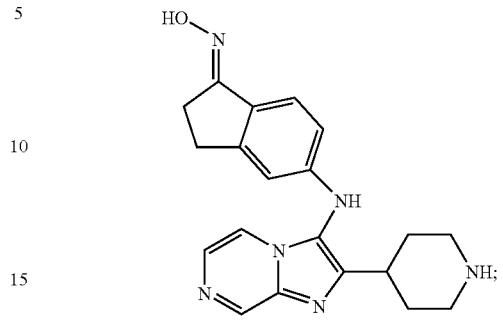

and stereoisomers, tautomers, and pharmaceutically acceptable salts thereof.

20. A pharmaceutical composition comprised of a compound of claim 1 and a pharmaceutically acceptable carrier.

21. The composition according to claim 20, further comprising an additional therapeutic agent selected from an anti-proliferative agent, an anti-inflammatory agent, an immunomodulatory agent, a neurotrophic factor, an agent for treating cardiovascular disease, an agent for treating liver disease, an anti-viral agent, an agent for treating blood disorders, an agent for treating diabetes, or an agent for treating immunodeficiency disorders.

* * * * *